(12) United States Patent
Brandl et al.

(10) Patent No.: US 7,691,868 B2
(45) Date of Patent: Apr. 6, 2010

(54) THIAZOLYL-DIHYDRO-QUINAZOLINE

(75) Inventors: Trixi Brandl, Basel (CH); Udo Maier, Senden (DE); Matthias Hoffmann, Mittelbiberach (DE); Stefan Scheuerer, Warthausen (DE); Anne T. Joergensen, Biberach (DE); Alexander Pautsch, Ulm (DE); Steffen Breitfelder, Assmannshardt (DE); Matthias Grauert, Biberach (DE); Christoph Hoenke, Ingelheim (DE); Klaus Erb, Mittelbiberach (DE); Michael Pieper, Biberach (DE); Ingo Pragst, Munich (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 11/690,362

(22) Filed: Mar. 23, 2007

(65) Prior Publication Data
US 2007/0244104 A1 Oct. 18, 2007

(30) Foreign Application Priority Data
Apr. 6, 2006 (EP) .................... 06112300

(51) Int. Cl.
| | | |
|---|---|---|
| A01N 43/54 | (2006.01) | |
| A61K 31/505 | (2006.01) | |
| C07D 239/00 | (2006.01) | |
| C07D 471/00 | (2006.01) | |
| C07D 487/00 | (2006.01) | |
| C07D 491/00 | (2006.01) | |

(52) U.S. Cl. ..................... 514/267; 544/250
(58) Field of Classification Search ............... 514/267; 544/250
See application file for complete search history.

(56) References Cited

U.S. PATENT DOCUMENTS

| 4,380,640 A | 4/1983 | Brunner et al. |
|---|---|---|
| 2002/0151544 A1 | 10/2002 | Hayakawa et al. |
| 2006/0100254 A1 | 5/2006 | Betzemeier et al. |
| 2006/0106013 A1* | 5/2006 | Breitfelder et al. ....... 514/232.5 |
| 2007/0238718 A1 | 10/2007 | Grauert et al. |
| 2007/0238730 A1 | 10/2007 | Breitfelder et al. |
| 2007/0238746 A1* | 10/2007 | Brandl et al. ............. 514/267 |
| 2007/0244104 A1 | 10/2007 | Brandl et al. |
| 2007/0259855 A1 | 11/2007 | Maier et al. |

FOREIGN PATENT DOCUMENTS

| WO | WO 01/57008 A1 | 8/2001 |
|---|---|---|
| WO | WO 03/072557 A1 | 9/2003 |
| WO | WO 2004/007491 A1 | 1/2004 |
| WO | WO 2004/029055 A1 | 4/2004 |
| WO | WO 2004/052373 A1 | 6/2004 |
| WO | WO 2004/056820 A1 | 7/2004 |
| WO | WO 2005/005438 A1 | 1/2005 |
| WO | WO 2005/016245 A2 | 2/2005 |
| WO | WO 2005/037843 * | 4/2005 |
| WO | WO 2005/037843 A1 | 4/2005 |
| WO | WO 2006/040279 A1 | 4/2006 |
| WO | WO 2006/040281 A1 | 4/2006 |

OTHER PUBLICATIONS

G. Y. Oudit, et al., "Phosphoinositide 3-Kinase γ-Deficient Mice are Protected from Isoproterenol-Induced Heart Failure", Circulation, 2003, vol. 108, No. 17, p. 2147-2152.

B. Vanhaesebroeck, et al., "Synthesis and Function of 3-Phosphorylated Inositol Lipids", Annual Review of Biochemistry, 2001, vol. 70, p. 535-602.

S. Ward, et al., "Isoform-specific phosphoinositide 3-kinase inhibitors as therapeutic agents", Current Opinion in Pharmacology, 2003, vol. 3, p. 426-434.

ISR for PCT/EP2007/052912 mailed Nov. 27, 2008.

Maier U. et al., "Roles of Non-Catalytic Subunits in Gβγ-Induced Activation of Class 1 Phosphoinositide 3-Kinase Isoforms β and γ", *The Journal of Biological Chemistry* 274(41):29311-29317 (1999).

* cited by examiner

*Primary Examiner*—James O Wilson
*Assistant Examiner*—Erich A Leeser
(74) *Attorney, Agent, or Firm*—Michael P. Morris; Mary-Ellen M. Devlin; Anthony P. Bottino

(57) ABSTRACT

Disclosed are thiazolyl-dihydro-quinazolines of general formula (I)

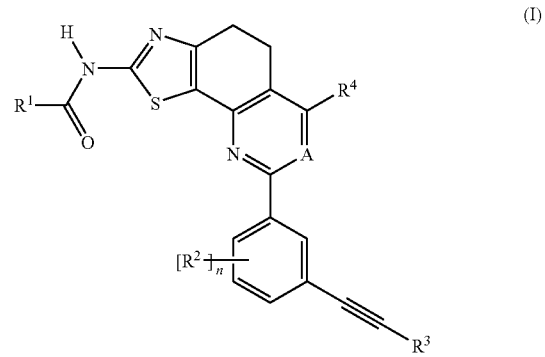

(I)

wherein the groups $R^1$ to $R^4$ have the meanings given in the claims and specification, the isomers thereof, and processes for preparing these compounds and their use as pharmaceutical compositions.

9 Claims, No Drawings

THIAZOLYL-DIHYDRO-QUINAZOLINE

APPLICATION DATA

This application claims benefit to EP 06112300 filed Apr. 6, 2006.

The present invention relates to new thiazolyl-dihydro-quinazolines of general formula (I)

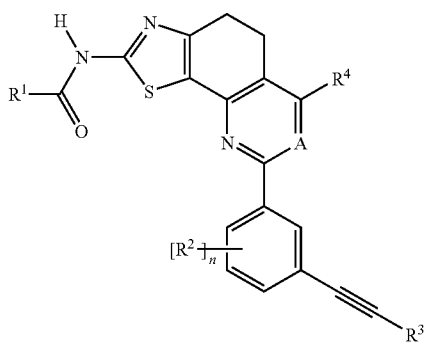

wherein X and the groups $R^1$ to $R^4$ have the meanings given in the claims and specification, the isomers thereof, and processes for preparing these thiazolyl-dihydro-quinazolines and their use as pharmaceutical compositions.

BACKGROUND TO THE INVENTION

Phosphatidylinositol-3-kinases (PI3-kinases) are a sub-family of the lipid kinases which catalyse the transfer of a phosphate group to the 3'-position of the inositol ring of phosphoinositides.

They have a role in numerous cell processes such as e.g. cell growth and differentiation processes, the control of cytoskeletal changes and the regulation of intra-cellular transport processes (Vanhaesebroeck et al., Annu Rev Biochem. 2001; 70:535-602).

PI3-kinases may play a part in numerous tumours, such as e.g. breast cancer, ovarian or pancreatic carcinoma, in tumour types such as carcinomas of the colon, breast or lungs, but particularly in autoimmune diseases such as Crohn's disease or rheumatoid arthritis, for example, or in the cardiovascular system, e.g. in the development of cardiac hypertrophy (Oudit et al., Circulation. 2003 Oct. 28; 108(17):2147-52). PI3-kinase modulators may represent a possible method of anti-inflammatory therapy with comparatively minor side effects (Ward and Finan, Curr Opin Pharmacol. 2003 August; 3(4): 426-34).

PI3-kinase inhibitors for treating inflammatory diseases are known in the literature. Thus, WO 03/072557 discloses 5-phenylthiazole derivatives, WO 04/029055 discloses annelated azolpyrimidines and WO 04/007491 discloses azolidinone-vinyl linked benzene derivatives. Moreover, the two specifications WO 04/052373 and WO 04/056820 disclose benzoxazine and benzoxazin-3-one derivatives.

The aim of the present invention is to provide new compounds which by virtue of their pharmaceutical activity as PI3-kinase modulators may be used therapeutically for the treatment of inflammatory or allergic diseases. Examples of these include inflammatory and allergic respiratory complaints, inflammatory and allergic skin complaints, inflammatory eye diseases, diseases of the nasal mucosa, inflammatory or allergic illnesses which involve autoimmune reactions or kidney inflammation.

DESCRIPTION OF THE INVENTION

Surprisingly it has been found that the aim outlined above is achieved by means of compounds of formula (I), wherein the groups $R^1$ to $R^4$ have the meanings given hereinafter.

It has particularly been found that compounds of formula (I) act as inhibitors of PI3-kinase, particularly as inhibitors of PI3-kinase gamma. Thus the compounds according to the invention may be used for example for the treatment of respiratory complaints.

The present invention therefore relates to compounds of general formula (I),

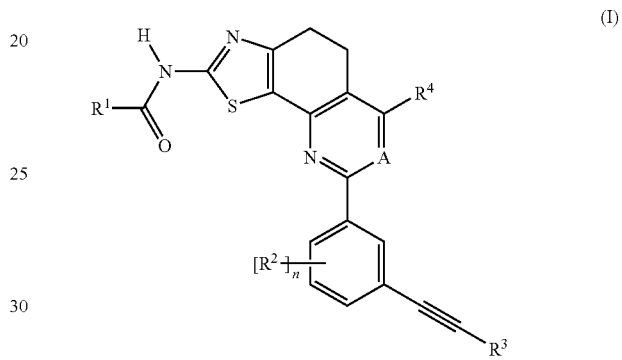

wherein n denotes 1, 2, 3, 4,

A denotes CH or N, $R^1$ denotes hydrogen or a group, optionally substituted, consisting of $C_{1-4}$-alkyl, $OR^{1.1}$ and $NR^{1.1}R^{1.2}$;

$R^{1.1}$, $R^{1.2}$ which may be identical or different, denote H or $C_{1-4}$-alkyl;

or $NR^{1.1}R^{1.2}$ denotes a 5- to 6-membered heterocycle, optionally containing a further N atom;

$R^2$ which may be identical or different, denote hydrogen or a group selected from among F, Cl, Br, I, CN, $CF_3$, $CF_2H$, $CFH_2$ and $NH_2$; or a group, optionally substituted, selected from among —O—$C_{1-4}$-alkyl, $C_{1-4}$-alkyl and $C_{2-6}$-alkenyl;

$R^4$ denotes hydrogen, OH, $NH_2$, or a group, optionally substituted, selected from among $C_{1-6}$-alkyl, $C_{2-6}$-alkenyl, $C_{3-6}$-cycloalkyl, —N($C_{1-4}$-alkyl)$_2$ and —NH($C_{1-4}$-alkyl);

$R^3$ a group selected from among:

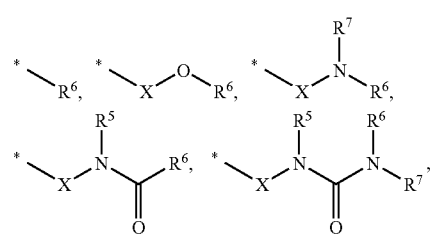

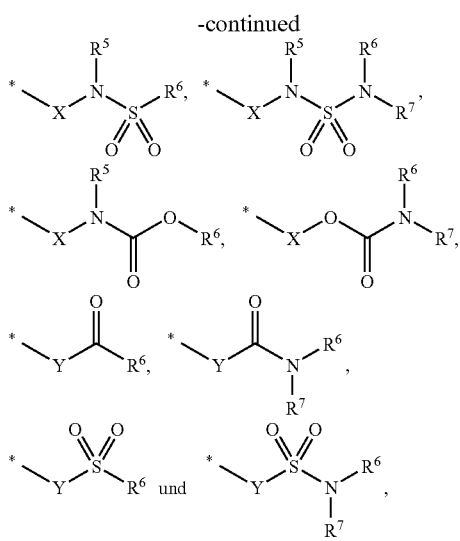

wherein

X denotes a group, optionally substituted, selected from among $C_{1-6}$-alkylene, $C_{2-5}$-alkenylene, $C_{1-5}$-alkynylene, $C_{3-7}$-cycloalkylene, $C_{5-7}$-cycloalkenylene and —$C_{1-4}$-alkylene-$C_{3-7}$-cycloalkylene;

Y denotes a bond or X;

$R^5, R^6, R^7$ which may be identical or different, denote hydrogen or a group, optionally substituted, selected from among $C_{1-6}$-alkyl, $C_{2-6}$-alkenyl, $C_{2-6}$-alkynyl, $C_{1-6}$-haloalkyl, $C_{3-8}$-cycloalkyl, $C_{3-8}$-cycloalkenyl, $C_{3-7}$-cycloalkyl-$C_{1-4}$-alkyl, aryl, heteroaryl, spiro, heterocycloalkyl, aryl-$C_{1-6}$-alkyl, heteroaryl-$C_{1-6}$-alkyl- and heterocycloalkyl-$C_{1-6}$-alkyl, or $NR^6R^7$ form a five-, six- or seven-membered ring consisting of carbon atoms and optionally a nitrogen, oxygen or sulphur atom as further heteroatoms or a ring selected from among:

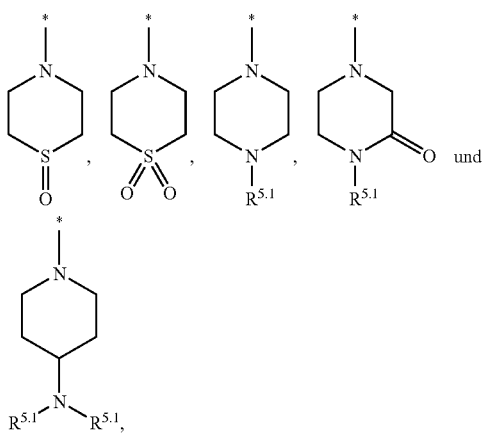

wherein, $R^{5.1}$ which may be identical or different, denote hydrogen or a group selected from among $C_{1-6}$-alkyl, $C_{3-8}$-cycloalkyl, —CO—$C_{1-3}$-alkyl and $CONH_2$;

or $R^5$ and $R^6$ together form a saturated or unsaturated alkylene bridge which is optionally substituted and may optionally contain a further nitrogen, oxygen or sulphur atom;

or $R^3$ is equal to

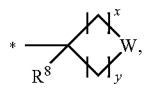

wherein x, y which may be identical or different denote 0, 1, 2, 3, 4 or 5;

W denotes O, $NR^9$ or $CR^9R^{10}$;

$R^8$ denotes H, $OR^{8.1}$, $NR^{8.1}R^{8.2}$ or optionally substituted $C_{1-6}$-alkyl;

$R^{8.1}, R^{8.2}$ which may be identical or different, denote hydrogen, $COR^{8.1.1}$, $CONR^{8.1.1}R^{8.1.2}$, $SO_2NR^{8.1.1}R^{8.1.2}$ or $SO_2R^{8.1.1}$ or a group, optionally substituted, selected from among $C_{1-6}$-alkyl, $C_{3-6}$-alkenyl, $C_{3-6}$-alkynyl, $C_{3-8}$-cycloalkyl and $C_{3-7}$-cycloalkyl-$C_{1-4}$-alkyl, or $NR^{8.1}R^{8.2}$ together form a five-, six- or seven-membered ring which may optionally contain a further heteroatom;

$R^{8.1.1}, R^{8.1.2}$ which may be identical or different, denote hydrogen or a group, optionally substituted, selected from among $C_{1-6}$-alkyl, $C_{3-8}$-cycloalkyl and $C_{3-7}$-cycloalkyl-$C_{1-4}$-alkyl, or $NR^{8.1.1}R^{8.1.2}$ together form a five- or six-membered ring, which may optionally contain a further heteroatom;

$R^9, R^{10}$ which may be identical or different, denote a group, optionally substituted by OMe, CN, F, Cl or Br, selected from among $C_{1-6}$-alkyl, $C_{2-6}$-alkenyl, $C_{2-6}$-alkynyl, $C_{3-8}$-cycloalkyl, $C_{3-8}$-cycloalkenyl, $C_{3-7}$-cycloalkyl-$C_{1-4}$-alkyl, aryl, heteroaryl, spiro, heterocycloalkyl, aryl-$C_{1-6}$-alkyl- and heteroaryl-$C_{1-6}$-alkyl-; or $R^9, R^{10}$ which may be identical or different, denote hydrogen, $COR^{9.1}$, $CONR^{9.1}R^{9.2}$, $SO_2R^{9.1}$ or $SO_2NR^{9.1}R^{9.2}$;

$R^{9.1}, R^{9.2}$ which may be identical or different, denote hydrogen or an optionally substituted group selected from among $C_{1-6}$-alkyl, $C_{2-6}$-alkenyl, $C_{2-6}$-alkynyl, $C_{1-6}$-haloalkyl, $C_{3-8}$-cycloalkyl, $C_{3-7}$-cycloalkyl-$C_{1-4}$-alkyl, aryl, heteroaryl, spiro, heterocycloalkyl, aryl-$C_{1-6}$-alkyl- and heteroaryl-$C_{1-6}$-alkyl-;

or $NR^{9.1}R^{9.2}$ together form a five- or six-membered ring, which may optionally contain a further heteroatom, optionally in the form of the tautomers, the racemates, the enantiomers, the diastereomers and the mixtures thereof, and optionally the pharmacologically acceptable acid addition salts, solvates and hydrates thereof.

Preferred are compounds of formula (IA) according to claim 1,

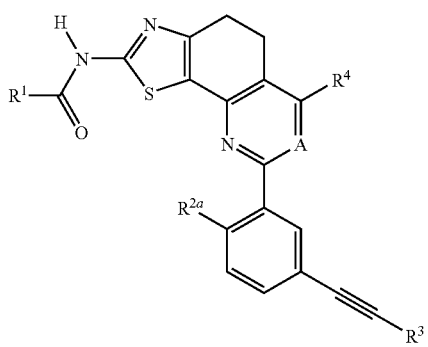

(IA)

wherein
A denotes CH, N
$R^1$, $R^3$, and $R^4$ may have the meanings stated and
$R^{2a}$ denotes a group selected from among F, Cl, Br, I, CN, $CF_3$, $CF_2H$, $CFH_2$ and $NH_2$;
or
a group, optionally substituted, selected from among —O—$C_{1-4}$-alkyl, $C_{1-4}$-alkyl and $C_{2-6}$-alkenyl.

Also preferred are compounds of formula (I) or (IA), wherein
$R^3$ may have the meanings stated and
n denotes 1 or 2,
$R^1$ denotes $C_{1-4}$-alkyl or $NR^{1.1}R^{1.2}$;
$R^{1.1}$, $R^{1.2}$ which may be identical or different, denote H or $C_{1-4}$-alkyl;
$R^2$ and/or $R^{2a}$, which may be identical or different, denote hydrogen, F or Cl; and
$R^4$ denotes hydrogen.

Also preferred are compounds of formula (I) or (IA), wherein
$R^1$, $R^2$, $R^{2a}$ and $R^4$ may have the meanings stated and
$R^3$ denotes a group selected from among:

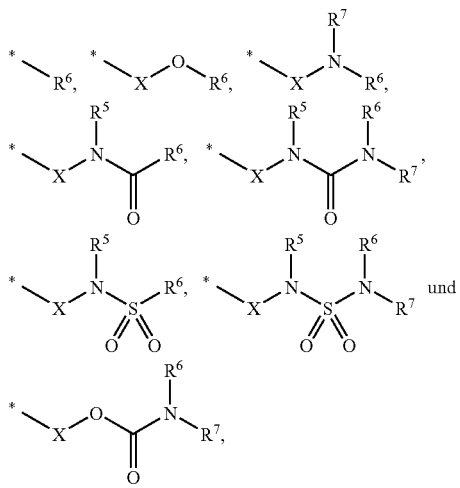

wherein
X denotes optionally substituted $C_{1-3}$-alkylene
$R^5$, $R^6$, $R^7$ which may be identical or different, denote hydrogen or a group, optionally substituted, selected from among $C_{1-6}$-alkyl, $C_{2-6}$-alkenyl, $C_{1-6}$-haloalkyl, $C_{3-8}$-cycloalkyl, $C_{3-7}$-cycloalkyl-$C_{1-4}$-alkyl, aryl, heteroaryl, heterocycloalkyl, aryl-$C_{1-5}$-alkyl, heteroaryl-$C_{1-5}$-alkyl, heterocycloalkyl-$C_{1-5}$-alkyl- and $N(C_{1-3}$-alkyl$)_2$-$C_{1-4}$-alkyl,
or
$NR^6R^7$ form a five- or six-membered ring consisting of carbon atoms and optionally a nitrogen or oxygen atom as a further heteroatom,
or
$NR^6R^7$ form a ring selected from among:

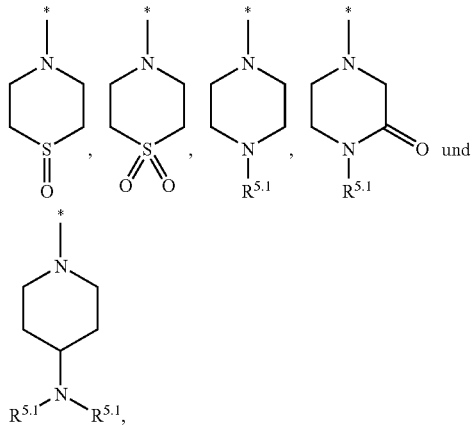

$R^{5.1}$ which may be identical or different, denote hydrogen or a group selected from among $C_{1-6}$-alkyl, $C_{3-8}$-cycloalkyl, —CO—$C_{1-3}$-alkyl and $CONH_2$.

Also preferred are compounds of formula (I), wherein
$R^1$, $R^2$, and $R^4$ may have the meanings stated and
$R^3$ denotes a group selected from among:

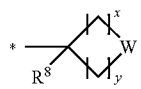

x, y which may be identical or different denote 0, 1, 2 or 3
W denotes $NR^9$ or $CR^9R^{10}$;
$R^8$ denotes H, $OR^{8.1}$ or $NR^{8.1}R^{8.2}$
$R^{8.1}$, $R^{8.2}$ which may be identical or different, denote hydrogen, $COR^{8.1.1}$, $CONR^{8.1.1}R^{8.1.2}$, or optionally substituted $C_{1-6}$-alkyl;
$NR^{8.1}R^{8.2}$ together form a five- or six-membered ring which may optionally contain a further heteroatom;
$R^{8.1.1}$, $R^{8.1.2}$ which may be identical or different, denote hydrogen or an optionally substituted $C_{1-6}$-alkyl,
$R^9$, $R^{10}$ which may be identical or different, denote a group, optionally substituted by OMe, CN, F, Cl or Br, selected from among $C_{1-6}$-alkyl, $C_{3-8}$-cycloalkyl, $C_{3-7}$-cycloalkyl-$C_{1-4}$-alkyl or
$R^9$, $R^{10}$ which may be identical or different, denote hydrogen, $COR^{9.1}$, $CONR^{9.1}R^{9.2}$, $SO_2R^{9.1}$ or $SO_2NR^{9.1}R^{9.2}$;
$R^{9.1}$, $R^{9.2}$ which may be identical or different, denote hydrogen or an optionally substituted group selected from among $C_{1-6}$-alkyl and $C_{3-8}$-cycloalkyl,
or
$NR^{9.1}R^{9.2}$ together form a five- or six-membered ring, which may optionally contain oxygen as a further heteroatom.

In another aspect the invention relates to compounds of formula (I) for use as pharmaceutical compositions.

The invention further relates to the use of the compounds of formula (I) for preparing a pharmaceutical composition for the treatment of diseases in whose pathology an activity of PI3-kinases is implicated, wherein therapeutically effective doses of the compounds of formula (I) may confer a therapeutic benefit.

The invention further relates to the use of the compounds of formula (I), for preparing a pharmaceutical composition for the treatment of inflammatory and allergic diseases of the airways.

The invention further relates to the use of the compounds of formula (I), for preparing a pharmaceutical composition for the treatment of a disease, which is selected from among chronic bronchitis, bronchitis caused by bacterial or viral infections or fungi or helminths, allergic bronchitis, toxic bronchitis, chronic obstructive bronchitis (COPD), asthma (intrinsic or allergic), paediatric asthma, bronchiectases, allergic alveolitis, allergic or non-allergic rhinitis, chronic sinusitis, cystic fibrosis or mucoviscidosis, alpha1-antitrypsin deficiency, coughing, pulmonary emphysema, interstitial lung diseases, alveolitis, hyperreactive airways, nasal polyps, pulmonary oedema, pneumonitis of various causes, such as radiation-induced or caused by aspiration or infection, collagenoses such as lupus erythematodes, systemic scleroderma, sarcoidosis and Boeck's disease.

The invention further relates to the use of the compounds of formula (I), for preparing a pharmaceutical composition for the treatment of inflammatory and allergic diseases of the skin.

The invention further relates to the use of the compounds of formula (I), for preparing a pharmaceutical composition for the treatment of a disease which is selected from among psoriasis, contact dermatitis, atopical dermatitis, alopecia areata (circular hair loss), erythema exsudativum multiforme (Stevens-Johnson Syndrome), dermatitis herpetiformis, sclerodermy, vitiligo, nettle rash (urticaria), lupus erythematodes, follicular and surface pyoderma, endogenous and exogenous acne, acne rosacea and other inflammatory and allergic or proliferative skin complaints.

The invention further relates to the use of the compounds of formula (I), for preparing a pharmaceutical composition for the treatment of inflammation of the eye.

The invention further relates to the use of the compounds of formula (I), for preparing a pharmaceutical composition for the treatment a disease which is selected from among conjunctivitis of various kinds, such as e.g. caused by fungal or bacterial infections, allergic conjunctivitis, irritable conjunctivitis, conjunctivitis caused by drugs, keratitis and uveitis.

The invention further relates to the use of the compounds of formula (I), for preparing a pharmaceutical composition for the treatment of diseases of the nasal mucosa.

The invention further relates to the use of the compounds of formula (I), for preparing a pharmaceutical composition for the treatment of a disease, which is selected from among allergic rhinitis, allergic sinusitis and nasal polyps.

The invention further relates to the use of the compounds of formula (I), for preparing a pharmaceutical composition for the treatment of inflammatory or allergic conditions involving autoimmune reactions.

The invention further relates to the use of the compounds of formula (I), for preparing a pharmaceutical composition for the treatment of a disease which is selected from among Crohn's disease, ulcerative colitis, systemic lupus erythematodes, chronic hepatitis, multiple sclerosis, rheumatoid arthritis, psoriatic arthritis, osteoarthritis, rheumatoid spondylitis.

The invention further relates to the use of the compounds of formula (I), for preparing a pharmaceutical composition for the treatment of kidney inflammation. The invention further relates to the use of the compounds of formula (I), for preparing a pharmaceutical composition for the treatment of a disease which is selected from among glomerulonephritis, interstitial nephritis and idiopathic nephrotic syndrome.

Of particular importance according to the invention is a pharmaceutical formulation containing a compound of formula (I). Preferred is an orally administered pharmaceutical formulation containing a compound of formula (I).

The invention further relates to a process for preparing compounds of general formula (I),

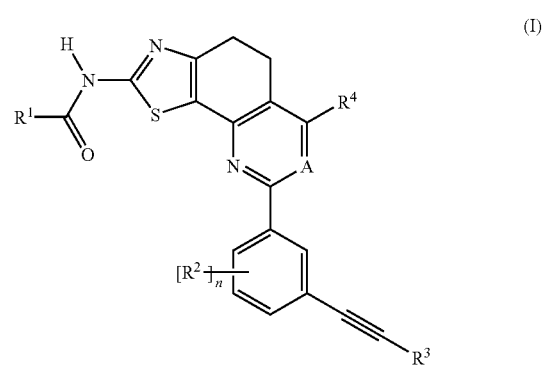

(I)

wherein

A, $R^1$ to $R^4$ may have the meanings stated, characterised in that (a) a compound of formula (II)

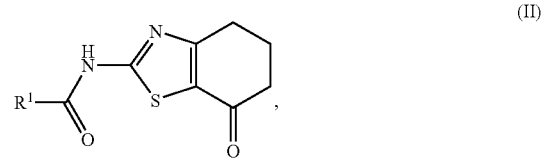

(II)

wherein $R^1$ has the meaning specified, is reacted with a compound of formula

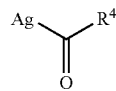

wherein $R^4$ has the meaning specified and Ag denotes a leaving group, and (b) the compound of general formula (III)

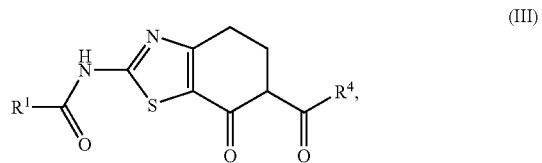

(III)

resulting from step (a), wherein $R^1$ and $R^4$ have the meanings specified, is reacted with a compound of general formula

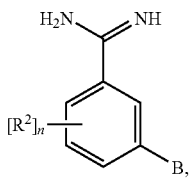

wherein R² and n have the meanings specified and B denotes a leaving group, and (c) the compound of general formula (IV)

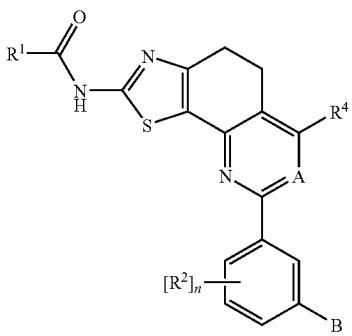

resulting from step (b), wherein R¹, R², R⁴ and n have the meanings specified and B denotes a leaving group, is reacted with a compound of general formula

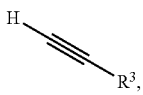

wherein R³ has the meaning specified.

In another aspect the invention relates to compounds according to general formula (II),

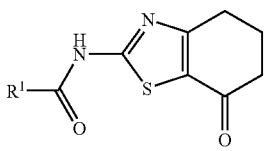

wherein
R¹ has the meanings specified, optionally in the form of the tautomers, the racemates, the enantiomers, the diastereomers and the mixtures thereof, and optionally the pharmacologically acceptable acid addition salts thereof.

In another aspect the invention relates to compounds according to general formula (III),

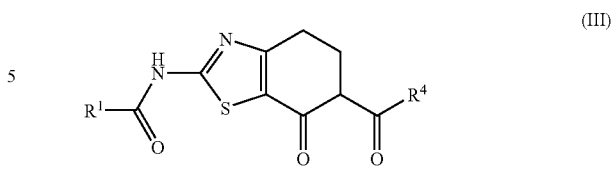

wherein
R¹ and R⁴ have the meanings specified, optionally in the form of the tautomers, the racemates, the enantiomers, the diastereomers and the mixtures thereof, and optionally the pharmacologically acceptable acid addition salts thereof.

In another aspect the invention relates to compounds according to general formula (IV),

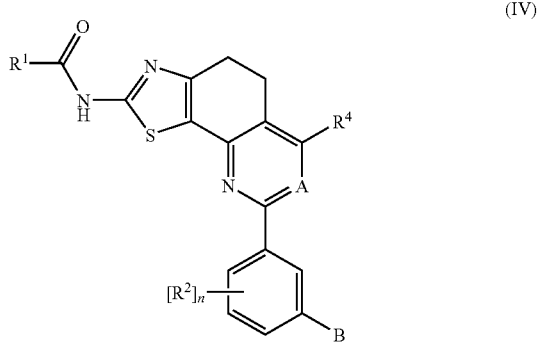

wherein
wherein R¹, R², R⁴ and n have the meanings specified and B denotes a leaving group, optionally in the form of the tautomers, the racemates, the enantiomers, the diastereomers and the mixtures thereof, and optionally the pharmacologically acceptable acid addition salts thereof.

TERMS AND DEFINITIONS USED

Unless otherwise stated, the above-mentioned terms propyl, butyl, pentyl, hexyl, heptyl, octyl, nonyl and decyl include all the possible isomeric forms. For example, the term propyl includes the two isomeric groups n-propyl and iso-propyl, the term butyl includes n-butyl, iso-butyl, sec. butyl and tert.-butyl, the term pentyl includes isopentyl, neopentyl etc.

In the above-mentioned alkyl groups one or more hydrogen atoms may optionally be substituted by other groups. For example these alkyl groups may be substituted by the halogen atoms fluorine, chlorine, bromine or iodine. The substituents fluorine and chlorine are preferred. Particularly preferred is the substituent chlorine. Optionally all the hydrogen atoms of the alkyl group may be replaced.

Unless otherwise stated, the alkyl bridge used may be a branched or unbranched alkyl group with 4 to 7 carbon atoms, for example, an n-butyl, iso-butyl, sec. butyl and tert.-butyl, pentyl, iso-pentyl, neopentyl, etc. bridge. Particularly preferred are n-butyl or n-pentyl bridges. In the above-mentioned alkyl bridges 1 to 2 C atoms may optionally be replaced by one or more heteroatoms selected from among oxygen or sulphur, preferably oxygen or sulphur.

By the term "$C_{1-6}$-alkylene" (including those which are part of other groups) are meant branched and unbranched alkylene groups with 1 to 6 carbon atoms and by the term "$C_{1-4}$-alkylene" are meant branched and unbranched alkylene groups with 1 to 4 carbon atoms. Preferred are alkylene groups with 1 to 4 carbon atoms. Examples include: methylene, ethylene, propylene, 1-methylethylene, butylene, 1-methylpropylene, 1,1-dimethylethylene, 1,2-dimethylethylene, pentylene, 1,1-dimethylpropylene, 2,2-dimethylpropylene, 1,2-dimethylpropylene, 1,3-dimethylpropylene or hexylene. Unless stated otherwise, the definitions propylene, butylene, pentylene and hexylene include all the possible isomeric forms of the groups in question with the same number of carbons. Thus, for example, propyl also includes 1-methylethylene and butylene includes 1-methylpropylene, 1,1-dimethylethylene, 1,2-dimethylethylene.

Examples of alkenyl groups (including those which are part of other groups) are branched and unbranched alkylene groups with 2 to 10 carbon atoms, preferably 2-6 carbon atoms, particularly preferably 2-3 carbon atoms, provided that they have at least one double bond. Examples include: ethenyl, propenyl, butenyl, pentenyl etc. Unless stated otherwise, the above-mentioned terms propenyl, butenyl etc. include all the possible isomeric forms. For example the term butylene includes n-butenyl, 1-methylpropenyl, 2-methylpropenyl, 1,1-dimethylethenyl, 1,2-dimethylethenyl etc.

In the above-mentioned alkenyl groups, unless otherwise stated, optionally one or more hydrogen atoms may optionally be replaced by other groups. For example these alkyl groups may be substituted by the halogen atoms fluorine, chlorine, bromine or iodine. The substituents fluorine and chlorine are preferred. Particularly preferred is the substituent chlorine. Optionally all the hydrogen atoms of the alkenyl group may be replaced.

By the term "$C_{2-6}$-alkenylene" (including those which are part of other groups) are meant branched and unbranched alkenylene groups with 2 to 6 carbon atoms and by the term "$C_{2-4}$-alkenylene" are meant branched and unbranched alkylene groups with 2 to 4 carbon atoms. Alkenylene groups with 2 to 4 carbon atoms are preferred. Examples include: ethenylene, propenylene, 1-methylethenylene, butenylene, 1-methylpropenylene, 1,1-dimethylethenylene, 1,2-dimethylethenylene, pentenylene, 1,1-dimethylpropenylene, 2,2-dimethylpropenylene, 1,2-dimethylpropenylene, 1,3-dimethylpropenylene or hexenylene. Unless stated otherwise, the definitions propenylene, butenylene, pentenylene and hexenylene include all the possible isomeric forms of the groups in question with the same number of carbons. Thus, for example, propenyl also includes 1-methylethenylene and butenylene includes 1-methylpropenylene, 1,1-dimethylethenylene, 1,2-dimethylethenylene.

Examples of alkynyl groups (including those which are part of other groups) are branched and unbranched alkynyl groups with 2 to 10 carbon atoms, provided that they have at least one triple bond, for example ethynyl, propargyl, butynyl, pentynyl, hexynyl etc., preferably ethynyl or propynyl.

Preferred are alkynyl groups with 2 to 4 carbon atoms. Examples include: ethynyl, propynyl, butynyl, pentynyl, or hexynyl. Unless stated otherwise, the definitions propynyl, butynyl, pentynyl and hexynyl include all the possible isomeric forms of the groups in question. Thus, for example propynyl includes 1-propynyl and 2-propynyl, butynyl includes 1-, 2- and 3-butynyl, 1-methyl-1-propynyl, 1-methyl-2-propynyl etc.

In the above-mentioned alkynyl groups one or more hydrogen atoms may optionally be substituted by other groups unless stated otherwise. For example these alkyl groups may be substituted by the halogen atoms fluorine, chlorine, bromine or iodine. The substituents fluorine and chlorine are preferred. Particularly preferred is the substituent chlorine. Optionally all the hydrogen atoms of the alkynyl group may be replaced.

By the term "$C_{2-6}$-alkynylene" (including those which are part of other groups) are meant branched and unbranched alkynylene groups with 2 to 6 carbon atoms and by the term "$C_{2-4}$-alkynylene" are meant branched and unbranched alkylene groups with 2 to 4 carbon atoms. Preferred are alkynylene groups with 2 to 4 carbon atoms. Examples include: ethynylene, propynylene, 1-methylethynylene, butynylene, 1-methylpropynylene, 1,1-dimethylethynylene, 1,2-dimethylethynylene, pentynylene, 1,1-di methylpropynylene, 2,2-dimethylpropynylene, 1,2-dimethylpropynylene, 1,3-dimethylpropynylene or hexynylene. Unless stated otherwise, the definitions propynylene, butynylene, pentynylene and hexynylene include all the possible isomeric forms of the groups in question with the same number of carbons. Thus, for example propynyl also includes 1-methylethynylene and butynylene includes 1-methylpropynylene, 1,1-dimethylethynylene, 1,2-dimethylethynylene.

By cycloalkyl groups (including those which are part of other groups) are meant saturated cycloalkyl groups with 3-8 carbon atoms, for example cyclopropyl, cyclobutyl, cyclopentyl, cyclohexyl, cycloheptyl or cyclooctyl, preferably cyclopropyl, cyclopentyl or cyclohexyl, while each of the above-mentioned cycloalkyl groups may optionally carry one or more substituents or be anellated to a benzene ring. Moreover the cycloalkyl groups may form, in addition to monocyclic groups, bicyclic, bridged or spirocyclic ring systems.

By cycloalkenyl (including those which are part of other groups) are meant cyclic alkyl groups with 5 to 8, preferably 5 or 6 carbon atoms, which contain one or two double bonds. Examples include: cyclopentenyl, cyclopentadienyl, cyclohexenyl, cyclohexadienyl, cycloheptenyl, cycloheptadienyl, cyclooctenyl or cyclooctadienyl. Moreover the cycloalkenyl groups may form, in addition to monocyclic groups, bicyclic, bridged or spirocyclic ring systems.

By haloalkyl (including those which are part of other groups) are meant branched and unbranched alkyl groups with 1 to 6 carbon atoms, wherein one or more hydrogen atoms are replaced by a halogen atom selected from among fluorine, chlorine or bromine, preferably fluorine and chlorine, particularly preferably fluorine. By the term "$C_{1-4}$-haloalkyl" are meant correspondingly branched and unbranched alkyl groups with 1 to 4 carbon atoms, wherein one or more hydrogen atoms are replaced as described above. $C_{1-4}$-haloalkyl is preferred. Examples include: $CH_2F$, $CHF_2$, $CF_3$.

The term aryl denotes an aromatic ring system with 6 to 14 carbon atoms, preferably 6 or 10 carbon atoms, preferably phenyl, which, unless otherwise stated, may carry one or more substituents, for example.

By heterocycloalkyl groups are meant, unless otherwise described in the definitions, 5-, 6- or 7-membered, saturated or unsaturated, bridged, mono- or bicyclic heterocycles which may contain as heteroatoms nitrogen, oxygen or sulphur, for example tetrahydrofuran, tetrahydrofuranone, γ-butyrolactone, α-pyran, γ-pyran, dioxolane, tetrahydropyran, dioxane, dihydrothiophene, thiolane, dithiolane, pyrroline, pyrrolidine, pyrazoline, pyrazolidine, imidazoline, imidazolidine, tetrazole, piperidine, pyridazine, pyrimidine, pyrazine, piperazine triazine, tetrazine, morpholine, thiomorpholine, diazepan, oxazine, tetrahydro-oxazinyl, isothiazole, pyrazolidine, preferably pyrazolyl, pyrrolidinyl, piperidinyl, piperazinyl or tetrahydrooxazinyl, while the heterocycle may optionally be substituted. The ring may be linked to the molecule through a carbon atom or if available through a nitrogen atom.

Unless otherwise mentioned, a heterocyclic ring may be provided with a keto group. Examples of these include.

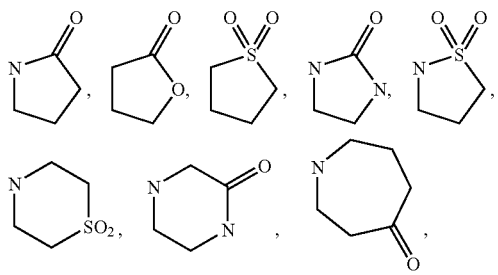

Examples of 5-10-membered bicyclic heterorings include pyrrolizine, indole, indolizine, isoindole, indazole, purine, quinoline, isoquinoline, benzimidazole, benzofuran, benzopyran, benzothiazole, benzothiazole, benzisothiazole, pyridopyrimidine, pteridine, pyrimidopyrimidine,

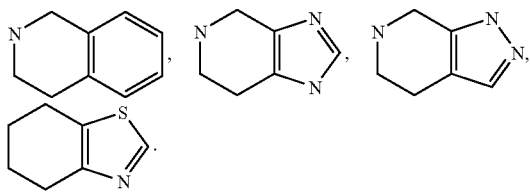

Examples of heteroaryl include 5-10-membered mono- or bicyclic heteroaryl rings in which up to three C atoms may be replaced by one or more heteroatoms selected from among oxygen, nitrogen or sulphur, while these may contain so many conjugated double bonds that an aromatic system is formed. Each of the above-mentioned heterocycles may optionally also be anellated to a benzene ring, preferably benzimidazole. The heteroaryl rings may, unless otherwise described, carry one or more substituents, for example.

The ring may be linked to the molecule through a carbon atom or if present through a nitrogen atom. The following are examples of five- or six-membered heterocyclic aromatic groups:

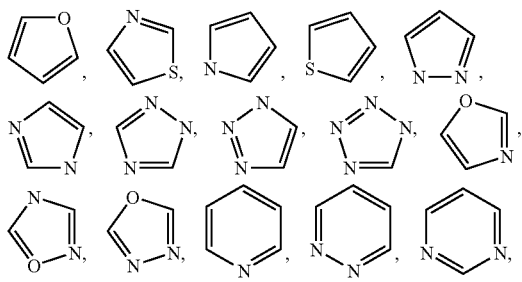

-continued

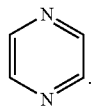

Examples of 5-10-membered bicyclic hetaryl rings include pyrrolizine, indole, indolizine, isoindole, indazole, purine, quinoline, isoquinoline, benzimidazole, benzofuran, benzopyran, benzothiazole, benzoisothiazole, pyridopyrimidine, pteridine, pyrimidopyrimidine.

By the term heterocyclic spiro rings ("spiro") are meant 5-10 membered, spirocyclic rings which may optionally contain one, two or three heteroatoms, selected from among oxygen, sulphur and nitrogen, while the ring may be connected to the molecule via a carbon atom or, if present, via a nitrogen atom. Unless otherwise stated, a spirocyclic ring may be provided with a keto group. Examples include:

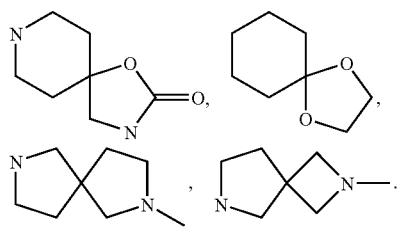

By the term "optionally substituted" is meant within the scope of the invention the above-mentioned group, optionally substituted by a lower-molecular group. Examples of lower-molecular groups regarded as chemically meaningful are groups consisting of 1-200 atoms. Preferably such groups have no negative effect on the pharmacological efficacy of the compounds.

For example the groups may comprise:

Straight-chain or branched carbon chains, optionally interrupted by heteroatoms, optionally substituted by rings, heteroatoms or other common functional groups.

Aromatic or non-aromatic ring systems consisting of carbon atoms and optionally heteroatoms, which may in turn be substituted by functional groups.

A number of aromatic or non-aromatic ring systems consisting of carbon atoms and optionally heteroatoms which may be linked by one or more carbon chains, optionally interrupted by heteroatoms, optionally substituted by heteroatoms or other common functional groups.

The term halogen generally denotes fluorine, chlorine, bromine or iodine.

The compounds according to the invention may occur in the form of the individual optical isomers, mixtures of the individual enantiomers, diastereomers or racemates, in the form of the tautomers as well as in the form of the free bases or the corresponding acid addition salts with pharmacologically acceptable acids—such as for example acid addition salts with hydrohalic acids, for example hydrochloric or hydrobromic acid, or organic acids, such as for example oxalic, fumaric, diglycolic or methanesulphonic acid.

A may represent N or CH, preferably N.

The substituent $R^1$ may represent a group selected from among hydrogen or a group, optionally substituted, consisting of $C_{1-4}$-alkyl, $OR^{1.1}$ and $NR^{1.1}R^{1.2}$; preferably $C_{1-4}$-alkyl and $NR^{1.1}R^{1.2}$. Particularly preferably the substituent $R^1$ denotes methyl or —NH—CH$_3$, particularly preferably methyl.

The substituents $R^{1.1}$, $R^{1.2}$ which may be identical or different, may denote H or $C_{1-4}$-alkyl, preferably H or methyl. $NR^{1.1}R^{1.2}$ may also denote a 5- to 6-membered heterocycle, optionally containing a further N atom.

The substituent $R^2$ which may be identical or different, may denote hydrogen or a group selected from among F, Cl, Br, I, CN, CF$_3$, CF$_2$H, CFH$_2$ and NH$_2$; preferably F, Cl and hydrogen, or a group, optionally substituted, selected from among —O—$C_{1-4}$-alkyl, $C_{1-4}$-alkyl and $C_{2-6}$-alkenyl.

The substituent $R^{2a}$ may represent a group selected from among F, Cl, Br, I, CN, CF$_3$, CF$_2$H, CFH$_2$ and NH$_2$, preferably hydrogen, F or Cl, or a group, optionally substituted, selected from among —O—$C_{1-4}$-alkyl, $C_{1-4}$-alkyl and $C_{2-6}$-alkenyl.

The substituent $R^{2b}$ may represent a group selected from among F, Cl, Br, I, CN, CF$_3$, CF$_2$H, CFH$_2$ and NH$_2$, preferably hydrogen, F or Cl, or a group, optionally substituted, selected from among —O—$C_{1-4}$-alkyl, $C_{1-4}$-alkyl and $C_{2-6}$-alkenyl.

The substituent $R^3$ may denote a group selected from among:

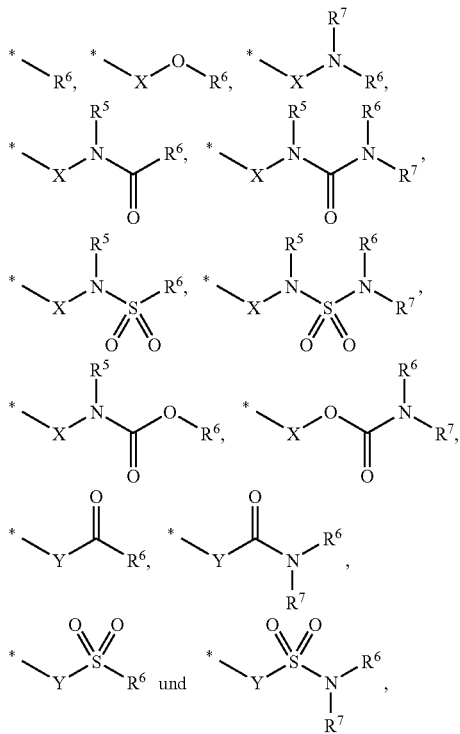

wherein

X denotes a group, optionally substituted, preferably unsubstituted, selected from among $C_{1-6}$-alkylene, $C_{2-5}$-alkenylene, $C_{1-5}$-alkynylene, $C_{3-7}$-cycloalkylene, $C_{5-7}$-cycloalkenylene and —$C_{1-4}$-alkylene-$C_{3-7}$-cycloalkylene, preferably $C_{1-3}$-alkylene, Y denotes a bond or X.

$R^3$ may preferably represent a group selected from among

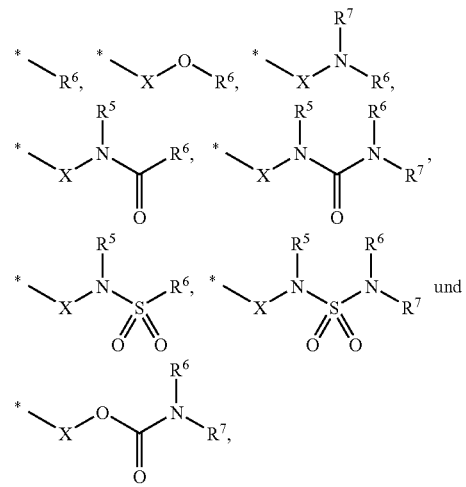

wherein

X denotes a group, optionally substituted, preferably unsubstituted, selected from among $C_{1-6}$-alkylene, $C_{2-5}$-alkenylene, $C_{1-5}$-alkynylene, $C_{3-7}$-cycloalkylene, $C_{5-7}$-cycloalkenylene and —$C_{1-4}$-alkylene-$C_{3-7}$-cycloalkylene, preferably $C_{1-3}$-alkylene.

The substituent $R^3$ is particularly preferably a group

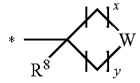

wherein x, y which may be identical or different denote 0, 1, 2, 3, 4 or 5; preferably x is 0, 1 or 2, particularly preferably 2, and y is 2 or 3, preferably 2.

W may represent O, $NR^9$ or $CR^9R^{10}$; preferably $NR^9$ or $CR^9R^{10}$.

The substituent $R^4$ may represent hydrogen, OH, NH$_2$, or a group, optionally substituted, selected from among $C_{1-6}$-alkyl, $C_{2-6}$-alkenyl, $C_{3-6}$-cycloalkyl, —N($C_{1-4}$-alkyl)$_2$ and —NH($C_{1-4}$-alkyl). Preferably the substituent $R^4$ denotes hydrogen.

The substituent $R^5$ may represent hydrogen or a group, optionally substituted, selected from among $C_{1-6}$-alkyl, $C_{2-6}$-alkenyl, $C_{2-6}$-alkynyl, $C_{1-6}$-haloalkyl, $C_{3-8}$-cycloalkyl, $C_{3-8}$-cycloalkenyl, $C_{3-7}$-cycloalkyl-$C_{1-4}$-alkyl, aryl, heteroaryl, spiro, heterocycloalkyl, aryl-$C_{1-6}$-alkyl, heteroaryl-$C_{1-6}$-alkyl- and heterocycloalkyl-$C_{1-6}$-alkyl, preferably $C_{1-4}$-alkyl and hydrogen, preferably methyl and hydrogen.

The substituent $R^6$ may represent hydrogen or a group, optionally substituted, selected from among $C_{1-6}$-alkyl, $C_{2-6}$-alkenyl, $C_{2-6}$-alkynyl, $C_{1-6}$-haloalkyl, $C_{3-8}$-cycloalkyl, $C_{3-8}$-cycloalkenyl, $C_{3-7}$-cycloalkyl-$C_{1-4}$-alkyl, aryl, heteroaryl, spiro, heterocycloalkyl, aryl-$C_{1-6}$-alkyl, heteroaryl-$C_{1-6}$-alkyl- and heterocycloalkyl-$C_{1-6}$-alkyl, preferably hydrogen or a group, optionally substituted, selected from among $C_{1-6}$-alkyl, $C_{1-6}$-haloalkyl, $C_{3-8}$-cycloalkyl, $C_{3-7}$-cycloalkyl-$C_{1-4}$-alkyl, aryl, heteroaryl, heterocycloalkyl- and aryl-$C_{1-6}$-alkyl.

The substituent $R^7$ may represent hydrogen or a group, optionally substituted, selected from among $C_{1-6}$-alkyl, $C_{2-6}$-alkenyl, $C_{2-6}$-alkynyl, $C_{1-6}$-haloalkyl, $C_{3-8}$-cycloalkyl, $C_{3-8}$-cycloalkenyl, $C_{3-7}$-cycloalkyl-$C_{1-4}$-alkyl, aryl, heteroaryl, spiro, heterocycloalkyl, aryl-$C_{1-6}$-alkyl, heteroaryl-$C_{1-6}$-alkyl- and heterocycloalkyl-$C_{1-6}$-alkyl, preferably hydrogen or a group, optionally substituted, selected from among $C_{1-6}$-alkyl, $C_{3-8}$-cycloalkyl, $C_{3-7}$-cycloalkyl-$C_{1-4}$-alkyl, heteroaryl, heteroaryl-$C_{1-6}$-alkyl- and heterocycloalkyl-$C_{1-6}$-alkyl.

$NR^6R^7$ may form a five-, six- or seven-membered ring, preferably a five- or six-membered ring, consisting of carbon atoms and optionally a nitrogen, oxygen or sulphur atom, preferably a nitrogen or oxygen atom, as further heteroatoms, or $NR^6R^7$ may form a ring selected from among:

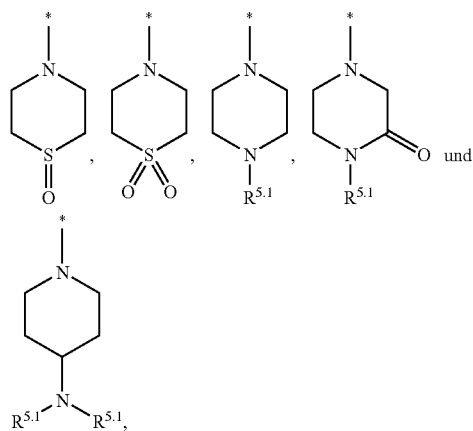

preferably from

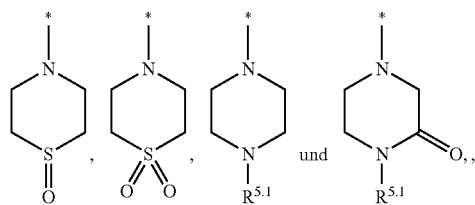

wherein $R^{5.1}$ which may be identical or different, denote hydrogen or a group selected from among $C_{1-6}$-alkyl, $C_{3-8}$-cycloalkyl, —CO—$C_{1-3}$-alkyl and $CONH_2$, preferably hydrogen or a group selected from among $C_{1-3}$-alkyl and $C_{3-6}$-cycloalkyl.

The substituent $R^8$ may represent H, $OR^{8.1}$, $NR^{8.1}R^{8.2}$ or optionally substituted $C_{1-6}$-alkyl; preferably H, $OR^{8.1}$ or $NR^{8.1}R^{8.2}$, particularly preferably $NR^{8.1}R^{8.2}$, wherein $R^{8.1}$, $R^{8.2}$ which may be identical or different, may represent hydrogen, $COR^{8.1.1}$, $CONR^{8.1.1}R^{8.1.2}$, $SO_2NR^{8.1.1}R^{8.1.2}$ or $SO_2R^{8.1.1}$, preferably hydrogen, or a group, optionally substituted, selected from among $C_{1-6}$-alkyl, $C_{3-6}$-alkenyl, $C_{3-6}$-alkynyl, $C_{3-8}$-cycloalkyl and $C_{3-7}$-cycloalkyl-$C_{1-4}$-alkyl, preferably hydrogen, $COR^{8.1.1}$, $CONR^{8.1.1}R^{8.1.2}$ or $C_{1-3}$-alkyl or $NR^{8.1}R^{8.2}$ together form a five-, six-or seven-membered ring, preferably a five- or six-membered ring, which may optionally contain a further heteroatom;

$R^{8.1.1}$, $R^{8.1.2}$ which may be identical or different, denote hydrogen or a group, optionally substituted, selected from among $C_{1-6}$-alkyl, $C_{3-8}$-cycloalkyl and $C_{3-7}$-cycloalkyl-$C_{1-4}$-alkyl, preferably hydrogen or $C_{1-3}$-alkyl or $NR^{8.1.1}R^{8.1.2}$ together form a five- or six-membered ring, which may optionally contain a further heteroatom;

The substituent $R^9$ may represent a group, optionally substituted by OMe, CN, F, Cl or Br, selected from among $C_{1-6}$-alkyl, $C_{2-6}$-alkenyl, $C_{2-6}$-alkynyl, $C_{3-8}$-cycloalkyl, $C_{3-8}$-cycloalkenyl, $C_{3-7}$-cycloalkyl-$C_{1-4}$-alkyl, aryl, heteroaryl, spiro, heterocycloalkyl, aryl-$C_{1-6}$-alkyl- and heteroaryl-$C_{1-6}$-alkyl-; preferably $C_{1-6}$-alkyl, $C_{3-6}$-cycloalkyl and $C_{3-6}$-cycloalkyl-$C_{1-4}$-alkyl, particularly preferably $C_{5-6}$-cycloalkyl or hydrogen, $COR^{9.1}$, $CONR^{9.1}R^{9.2}$, $SO_2R^{9.1}$ or $SO_2NR^{9.1}R^{9.2}$, wherein $R^{9.1}$, $R^{9.2}$ which may be identical or different, denote hydrogen or an optionally substituted group selected from among $C_{1-6}$-alkyl, $C_{2-6}$-alkenyl, $C_{2-6}$-alkynyl, $C_{1-6}$-haloalkyl, $C_{3-8}$-cycloalkyl, $C_{3-7}$-cycloalkyl-$C_{1-4}$-alkyl, aryl, heteroaryl, spiro, heterocycloalkyl, aryl-$C_{1-6}$-alkyl- and heteroaryl-$C_{1-6}$-alkyl-; preferably hydrogen or an optionally substituted group selected from among $C_{1-6}$-alkyl and $C_{3-6}$-cycloalkyl;

or $NR^{9.1}R^{9.2}$ together form a five- or six-membered ring, which may optionally contain a further heteroatom.

The substituent $R^{10}$ may represent a group, optionally substituted by OMe, CN, F, Cl or Br, selected from among $C_{1-6}$-alkyl, $C_{2-6}$-alkenyl, $C_{2-6}$-alkynyl, $C_{3-8}$-cycloalkyl, $C_{3-8}$-cycloalkenyl, $C_{3-7}$-cycloalkyl-$C_{1-4}$-alkyl, aryl, heteroaryl, spiro, heterocycloalkyl, aryl-$C_{1-6}$-alkyl- and heteroaryl-$C_{1-6}$-alkyl or hydrogen, $COR^{9.1}$, $CONR^{9.1}R^{9.2}$, $SO_2R^{9.1}$ or $SO_2NR^{9.1}R^{9.2}$, wherein $R^{9.1}$, $R^{9.2}$ which may be identical or different, denote hydrogen or an optionally substituted group selected from among $C_{1-6}$-alkyl, $C_{2-6}$-alkenyl, $C_{2-6}$-alkynyl, $C_{1-6}$-haloalkyl, $C_{3-8}$-cycloalkyl, $C_{3-7}$-cycloalkyl-$C_{1-4}$-alkyl, aryl, heteroaryl, spiro, heterocycloalkyl, aryl-$C_{1-6}$-alkyl- and heteroaryl-$C_{1-6}$-alkylor $NR^{9.1}R^{9.2}$ together form a five- or six-membered ring, which may optionally contain a further heteroatom Particularly preferably the group $R^{10}$ denotes hydrogen.

The leaving group A is a leaving group such as for example chlorine, O—$C_1$-$C_3$-alkyl, imidazolidine, preferably O—$C_1$-$C_3$-alkyl. The leaving group B is a leaving group such as for example chlorine, bromine, iodine, methanesulphonyl, trifluoromethanesulphonyl or p-toluenesulphonyl, preferably iodine.

Preparation Processes

The compounds of general formula (I) may be prepared according to the following synthesis plan (Diagram 1), wherein the substituents of general formula (I) have the meanings given above. These processes are to be understood as illustrating the invention without restricting it to their content.

Diagram 1:

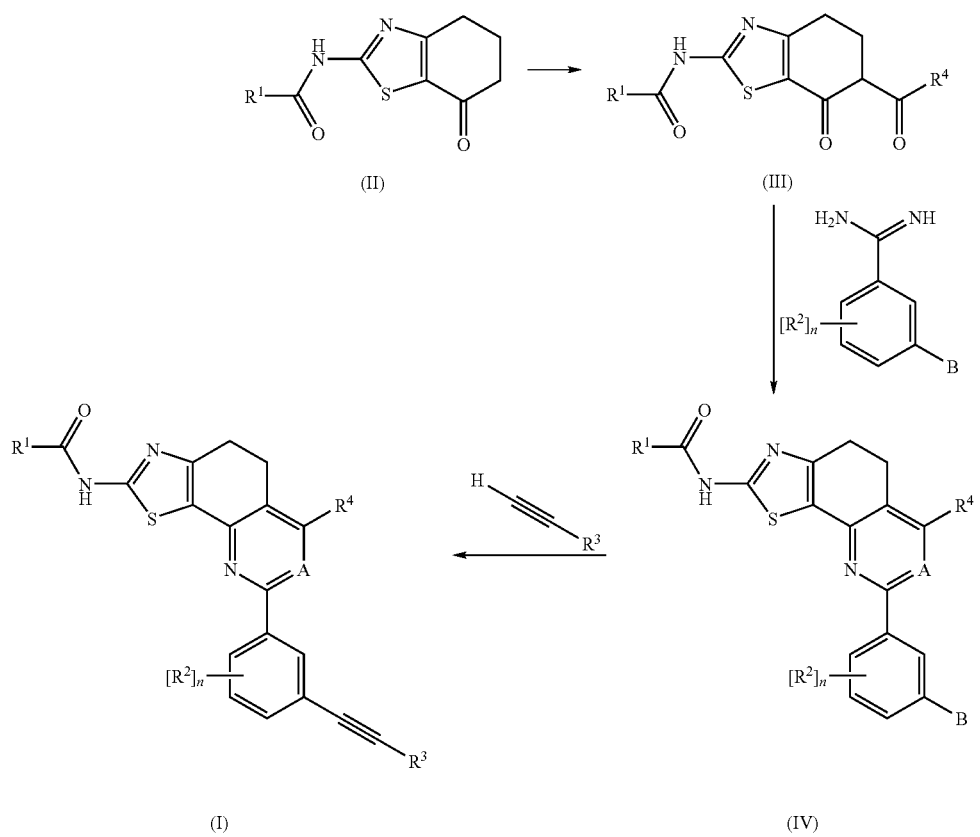

The new compounds of general formula (I) may be prepared analogously to the following Examples. The Examples described below are intended to illustrate the invention without restricting it.

Synthesis of the Reagents 1-cyclopentyl-4-ethynyl-piperidine

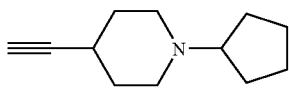

5.0 g (43.4 mmol) piperidin-4-yl-methanol are placed in 250 mL dichloromethane under an argon atmosphere and combined with 3.7 g (44.0 mmol) cyclopentanone. Then 3.6 g (44.0 mmol) sodium acetate and 14.0 g (66.0 mmol) sodium triacetoxyborohydride are added. The resulting suspension is stirred for 16 hours at ambient temperature. Then the reaction mixture is extracted with sodium hydrogen carbonate solution. The aqueous phase is saturated with sodium chloride and extracted with chloroform/methanol. The resulting organic phase is dried and evaporated to dryness. Yield: 6.0 g 1.1 mL (13.0 mmol) oxalyl chloride are placed in 200 mL dichloromethane under a nitrogen atmosphere and cooled to −78° C. 1.9 mL (27.3 mmol) dimethylsulphoxide dissolved in a little dichloromethane are added dropwise. The mixture is stirred for 0.3 hours, and then 2.0 g (10.9 mmol) of the intermediate described above in dichloromethane is added dropwise. The reaction mixture is stirred for 3 hours, then 7.9 mL (54.6 mmol) triethylamine are added dropwise. The cooling is removed and the reaction mixture is heated to ambient temperature. Then water is added and the phases are separated. The organic phase is washed with sodium hydrogen carbonate solution (50%) and water, dried and evaporated to dryness. Yield: 1.1 g 1.1 g (6.0 mmol) of the intermediate described above are dissolved in 50 mL methanol under an argon atmosphere and combined with 0.8 g (6.0 mmol) potassium carbonate. 1.2 g (6.2 mmol) dimethyl(1-diazo-2-oxo-propyl)-phosphate are dissolved in methanol and added to the mixture, then stirred for 4 hours at ambient temperature. Then the reaction mixture is poured onto 200 mL water and extracted with diethyl ether. The organic phase is dried and evaporated to dryness. Yield: 0.9 g 4-Ethynyl-1-isopropyl-piperidine and 1-cyclopentyl-methyl-4-ethynyl-piperidine are prepared analogously.

tert.butyl 4-ethynyl-piperidine-1-carboxylate

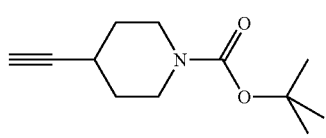

Can be prepared analogously to 1-cyclopentyl-4-ethynyl-piperidine starting from commercial 1-Boc-4-piperidinemethanol.

1-cyclopentyl-4-ethynyl-piperidin-4-ol

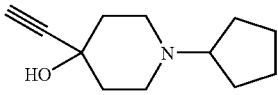

4.0 g (28.0 mmol) piperidone-4-ethyleneacetal are placed in 250 mL dichloromethane and combined with 2.4 g (28.5 mmol) cyclopentanone. Then 2.3 g (28.0 mmol) sodium acetate and 8.9 g (42 mmol) sodium triacetoxyborohydride are added. The resulting suspension is stirred for 16 hours at ambient temperature. Then the reaction mixture is extracted with sodium hydrogen carbonate solution and washed with water. The organic phase is dried and evaporated to dryness. Yield: 5.5 g 5.5 g (26.0 mmol) of the intermediate described above are placed in 10 mL acetone and combined with 110 mL 0.1 N aqueous hydrochloric acid. The reaction mixture is refluxed for 5 hours with stirring, then after cooling to ambient temperature made basic with 5 N sodium hydroxide solution and extracted with chloroform/dichloromethane. The organic phase is dried and evaporated to dryness. Yield: 4.1 g 3.1 mL (18.0 mmol) trimethylsilylacetylene are placed in 400 mL dry tetrahydrofuran under a nitrogen atmosphere at −70° C. and combined with 12.9 mL (22.4 mmol) n-butyllithium (2.5 M solution in hexane). After one hour 3.0 g (18.0 mmol) of the intermediate described above are dissolved in 100 mL tetrahydrofuran and slowly added dropwise to the mixture. This is stirred for 1 hour at −70° C. and for 16 hours at ambient temperature. Then the reaction mixture is combined with 300 mL saturated ammonium chloride solution, stirred for 0.1 hour, then poured onto 500 mL water. It is extracted with ethyl acetate, the combined organic phases are washed with water, dried and evaporated to dryness. Yield: 3:0 g 3.0 g (11.0 mmol) of the intermediate described above and 4.1 mL (14.0 mmol) tetrabutylammonium fluoride are stirred in dichloromethane for 1 hour at ambient temperature. Then the reaction mixture is washed with water, the organic phase is dried and evaporated to dryness. Yield: 0.9 g 4-Ethynyl-1-isopropyl-piperidin-4-ol may be prepared analogously.

(R)-2-ethynyl-pyrrolidine

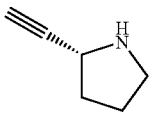

A mixture of 4.9 g (24.6 mmol) (R)-(+)-1-Boc-2-pyrrolidinecarbaldehyde and 4.0 g (29.0 mmol) potassium carbonate in 40 mL methanol is combined with 5.3 g (27.3 mmol) dimethyl(1-diazo-2-oxo-propyl)-phosphate and stirred for 4 hours at ambient temperature. Then the reaction mixture is poured onto water and extracted with diethyl ether. The organic phase is dried and gently evaporated down. The residue is combined with 3 mL ethereal hydrochloric acid (1 M), stirred overnight at ambient temperature and then evaporated down completely. Yield: 3.9 g (yellow oil)

(S)-2-ethynyl-pyrrolidine may be prepared analogously starting from (S)-(−)-1-Boc-2-pyrrolidinecarbaldehyde.

1-ethynyl-1-methoxy-cyclohexane

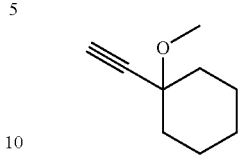

At ambient temperature 0.8 g (20 mmol) sodium hydride (60% in mineral oil) are added to a solution of 2 g (16 mmol) 1-ethynylcyclohexanol in 25 mL DMF. After 20 minutes 1.25 mL (20 mmol) methyliodide are added and stirring is continued for another hour. The reaction mixture is combined with ice and extracted with ether. The organic phase is dried and evaporated down. The residue remaining is purified by MPLC (dichloromethane/methanol 100:5). Yield: 0.6 g (clear oil)

4-Ethynyl-4-methoxy-1-methyl-piperidine and 1-cyclopentyl-4-ethynyl-4-methoxy-piperidine may be prepared analogously.

Ethyl-(1-ethynyl-cyclohexyl)-amine

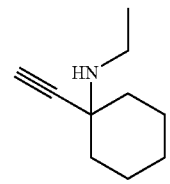

A solution consisting of 20 g (161 mmol) ethynylcyclohexanol and 25 mL (177 mmol) triethylamine and 200 mg (1.6 mmol) 4-dimethylaminopyridine in 200 mL dichloromethane is combined at 0° C. with 12.6 mL (177 mmol) acetyl chloride. After 5 hours at 0° C. the reaction mixture is combined with water and extracted with dichloromethane. The combined organic phases are evaporated down and the residue is purified by MPLC (cyclohexane/ethyl acetate 6:1). Yield: 3 g (yellow oil)

A mixture of 0.4 g (2.4 mmol) of the intermediate described above, 3.6 mL (7.2 mmol) ethylamine (2 M solution in THF) and 12 mg (0.12 mmol) copper(I)-chloride in 5 mL THF is refluxed for 3.5 hours. The reaction mixture is evaporated down, taken up in ethyl acetate and washed with ammonium chloride and sodium chloride solution. The organic phase is evaporated down. Yield: 0.15 g (brown oil)

The following amines may be prepared analogously: 1-(1-ethynyl-cyclohexyl)-pyrrolidine; (1-ethynyl-cyclohexyl)-dimethylamine; (1-ethynyl-cyclohexyl)-isopropylamine; 1-ethynyl-cyclohexyl)-methylamine; (1-ethynyl-cyclopentyl)-dimethylamine N-(1-ethynyl-cyclohexyl)-acetamide

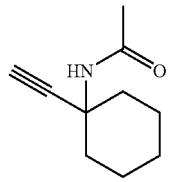

A solution of 4 g (32 mmol) 1-ethynylcyclohexylamine in 30 mL ether is combined at ambient temperature with 1.1 mL (15 mmol) acetyl chloride. The colourless suspension is stirred overnight at ambient temperature, the resulting solid is suction filtered and washed with diethyl ether/dichloromethane. The filtrate is evaporated down and yields the product as a colourless solid. Yield: 3 g N-but-3-ynyl-N-methyl-acetamide may be prepared analogously from but-3-ynyl-methyl-amine.

1-(1-ethynyl-cyclohexyl)-3-methylurea

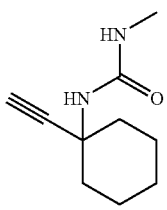

A solution of 1 g (8 mmol) 1-ethynylcyclohexylamine and 2 mL (15 mmol) triethylamine in 10 mL acetonitrile is combined at ambient temperature with 0.5 g (9 mmol) methylisocyanate. The colourless suspension is stirred overnight at ambient temperature and then evaporated down. The residue is taken up in dichloromethane and washed with aqueous potassium carbonate solution. The organic phase is dried and evaporated down. Yield: 1.4 g (colourless solid)

1-But-3-ynyl-1,3-dimethyl-urea may be prepared analogously from but-3-ynyl-methyl-amine.

1-prop-2-ynyl-1H-imidazole

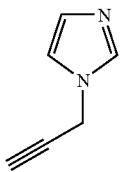

5 g (73 mmol) imidazole and 1.3 g (4 mmol) tetrabutylammonium iodide are placed in 200 mL toluene and 150 mL 50% sodium hydroxide solution and 15.7 mL (145 mmol) propargyl bromide are added. The mixture is stirred for 1 hour at ambient temperature, then diluted with toluene and water. The organic phase is dried and evaporated to dryness. The residue is purified by chromatography. Yield: 2.5 g 2-chloro-5-iodo-benzamidine

374.8 mL (374.8 mmol) lithium bis-trimethylsilylamide (1 M in hexane) are placed in 300 mL diethyl ether and combined with 50.0 g (189.8 mmol) 2-chloro-5-iodobenzonitrile. The reaction mixture is stirred for 1.5 hours at ambient temperature under an argon atmosphere and then cooled to 0° C. Then 5 molar hydrochloric acid is slowly added. The precipitate thus formed is suction filtered and dried. Yield: 56.0 g 3-Chloro-5-iodo-benzamidine, 2-fluoro-5-iodo-benzamidine as well as 3-iodo-benzamidine may be prepared analogously.

Synthesis of the Intermediate Compounds

N-(7-oxo-4,5,6,7-tetrahydro-benzothiazol-2-yl)-acetamide

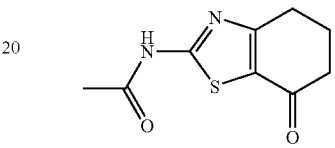

112 g (1.0 mol) 1,3-cyclohexanedione are suspended in 700 mL ice water and 51.6 mL (1.0 mol) bromine are added dropwise at 0° C. within 45 minutes. The suspension is stirred for 3.5 hours at max. 10° C. Then it is suction filtered and the solid is stirred in 800 mL water, suction filtered, washed with 3 L water and dried. The solid obtained is recrystallised from ethanol. Yield: 37 g (m.p.: 159-160° C.) 15.5 g (0.2 mol) thiourea are placed in 200 mL ethanol at ambient temperature. 37.1 g (0.2 mol) of the intermediate described above are added batchwise to this suspension, then it is rinsed with 60 mL ethanol. The solution that gradually forms is refluxed for 2 hours with stirring and then evaporated down. The residue is extracted with water and diethyl ether, the aqueous phase is made basic with sodium carbonate solution. The resulting solid is suction filtered, washed with water, then extracted with methanol and evaporated to dryness.

Yield: 22 g (m.p.: 265-268° C.)

230 mL (2.4 mol) acetic anhydride are placed at ambient temperature, 22 g (0.13 mol) of the intermediate described above are added and the mixture is refluxed for 3 hours with stirring. The suspension goes partly into solution. After cooling with ice/saline bath the solid is suction filtered, decocted 2× in 150 mL acetone, suction filtered and dried.

Yield: 25 g (m.p.: 268-272° C.)

N-(6-formyl-7-oxo-4,5,6,7-tetrahydro-benzothiazol-2-yl)-acetamide

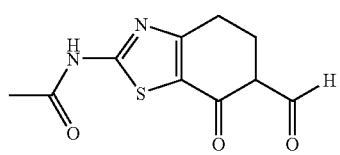

20 g (0.37 mol) sodium methoxide are suspended in 50 mL dimethylformamide, a suspension of 21 g (0.1 mol) N-(7-oxo-4,5,6,7-tetrahydro-benzothiazol-2-yl)-acetamide in 100 mL dimethylformamide is added dropwise. The mixture is stirred for 15 minutes, then cooled to 0° C. A mixture of 29.9 mL (0.37 mol) ethyl formate and 60 mL benzene is added dropwise and the reaction mixture is diluted with another 100 mL benzene. A precipitate gradually settles out and stirring is continued at 0° C. for 3.5 hours. The suspension is hydrolysed with 370 mL 1 molar hydrochloric acid, the solid precipitated is suction filtered. The two phases of the mother liquor are separated, the aqueous phase is extracted with dichloromethane. The resulting organic phase is dried and evaporated to dryness. The solid and the residue from the extraction are recrystallised from acetonitrile. Yield: 20 g N-[8-(2-chloro-5-iodo-phenyl)-4,5-dihydrothiazolo[4,5-h]quinazolin-2-yl]-acetamide

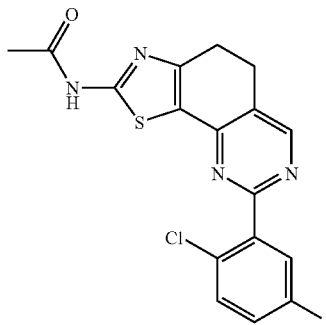

5.0 g (21.0 mmol) N-(6-formyl-7-oxo-4,5,6,7-tetrahydro-benzothiazol-2-yl)-acetamide and 7.3 g (23.0 mmol) 2-chloro-5-iodo-benzamidine are stirred in 50 mL pyridine for several hours at 160° C. After cooling to ambient temperature the precipitated solid is suction filtered, washed and dried. Yield: 4.7 g The following intermediates may be prepared analogously starting from 3-chloro-5-iodo-benzamidine, 2-fluoro-5-iodo-benzamidine and 3-iodo-benzamidine: N-[8-(3-chloro-5-iodo-phenyl)-4,5-dihydro-thiazolo[4,5-h]quinazolin-2-yl]-acetamide; N-[8-(2-fluoro-5-iodo-phenyl)-4,5-dihydro-thiazolo[4,5-h]quinazolin-2-yl]-acetamide; N-[8-(3-iodo-phenyl)-4,5-dihydro-thiazolo[4,5-h]quinazolin-2-yl]-acetamide Synthesis of Compounds of Formula (I)

The following HPLC-MS methods were used to characterise the compounds of formula (I):

HPLC-MS analysis

Method A
Waters ZMD, Alliance 2690/2695 HPLC, Waters 2700 Autosampler, Waters 996/2996 diode array detector
The following mobile phase was used:

| time in min | % A | % B | flow rate in ml/min |
| --- | --- | --- | --- |
| 0.0 | 95 | 5 | 1.00 |
| 0.1 | 95 | 5 | 1.00 |
| 3.1 | 2 | 98 | 1.00 |
| 4.5 | 2 | 98 | 1.00 |
| 5.0 | 95 | 5 | 1.00 |

A: water with 0.10% TFA
B: acetonitrile with 0.10% TFA

The stationary phase used was an XTerra® column, MS $C_{18}$ 2.5 µm, 4.6 mm×30 mm (column temperature: constant at 25° C.).

The diode array detection was carried out in the wavelength range 210-400 nm.

Method B
Waters ZMD, Alliance 2690/2695 HPLC, Waters 2700 Autosampler, Waters 996/2996 diode array detector
The following mobile phase was used:

| time in min | % A | % B | flow rate in ml/min |
| --- | --- | --- | --- |
| 0.00 | 95 | 5 | 2.00 |
| 0.10 | 95 | 5 | 2.00 |
| 2.10 | 2 | 98 | 2.00 |
| 3.00 | 2 | 98 | 2.00 |
| 3.25 | 95 | 5 | 2.00 |

A: water with 0.10% TFA
B: acetonitrile with 0.10% TFA

The stationary phase used was a Merck Chromolith™ column SpeedROD RP-18e, 4.6 mm×50 mm (column temperature: constant at 25° C.).

The diode array detection was carried out in the wavelength range 210-400 nm.

EXAMPLES

Example 1

N-{8-[2-chloro-5-(3-methylamino-prop-1-ynyl)-phenyl]-4,5-dihydro-thiazolo[4,5-h]quinazolin-2-yl}-acetamide

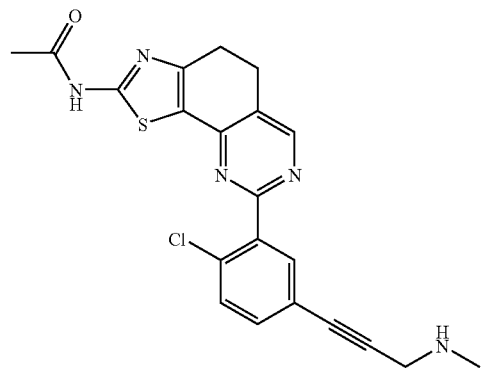

1.0 g (2.1 mmol) N-[8-(2-chloro-5-iod-phenyl)-4,5-dihydro-thiazolo[4,5-h]quinazolin-2-yl]-acetamide are placed in 50 mL tetrahydrofuran under an argon atmosphere and combined with 0.6 ml (9 mmol) N-methylpropargylamine and 1 mL (6 mmol) diisopropylethylamine. The mixture is kept free from oxygen and 29 mg (0.04 mmol) triphenylphosphine palladium(II)-chloride and 8 mg (0.04 mmol) copper(I)-iodide are added. The mixture is stirred for 5 hours at 80° C. After cooling to ambient temperature the reaction mixture is combined with water and 10% ammonia solution and extracted with dichloromethane. The organic phase is dried and evaporated to dryness. The residue is purified by chromatography, the product obtained is triturated with diethyl ether and suction filtered.
Yield: 0.27 g (MH+=424; RT=2.31; Method A)

The following compounds may be prepared analogously:

TABLE 1

| Example | R¹ | R²ᵃ | R²ᵇ | R⁴ | R³ | analysis HPLC-MS |
|---|---|---|---|---|---|---|
| 1 | H₃C—X₁ | Cl–X₂ | H | H | X₃–CH₂–NH–CH₃ | MH+ = 424<br>RT = 2.31<br>Method A |
| 2 | H₃C–N(CH₃)–X₁ | Cl–X₂ | H | H | X₃–(4-piperidinyl)-N-cyclopentyl | |
| 3 | H₃C—X₁ | F–X₂ | H | H | X₃–(4-piperidinyl)-N-cyclopentyl | MH+ = 516<br>RT = 2.51<br>Method A |
| 4 | H₃C–N(CH₃)–X₁ | Cl–X₂ | H | H | X₃–(4-OH-4-piperidinyl)-N-cyclopentyl | MH+ = 563<br>RT = 2.36<br>Method A |
| 5 | H₃C—X₁ | F–X₂ | H | H | X₃–(4-OH-4-piperidinyl)-N-cyclopentyl | MH+ = 532<br>RT = 2.42<br>Method A |
| 6 | H₃C–N(CH₃)–X₁ | Cl–X₂ | H | H | X₃–(4-OCH₃-4-piperidinyl)-N-cyclopentyl | |

TABLE 1-continued

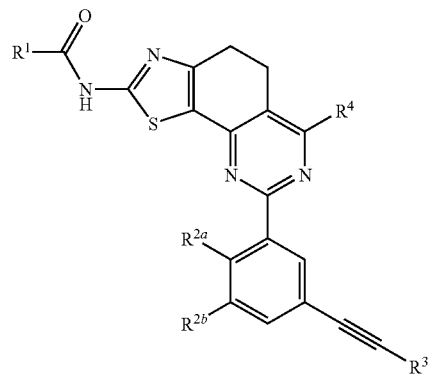

| Example | R¹ | R²ᵃ | R²ᵇ | R⁴ | R³ | analysis HPLC-MS |
|---|---|---|---|---|---|---|
| 7 | H₃C—X₁ | F—X₂ | H | H | 4-methoxy-4-(1-cyclopentylpiperidin-4-yl)-X₃ | MH+ = 546<br>RT = 2.58<br>Method A |
| 8 | H₃C—X₁ | Cl—X₂ | H | H | 4-hydroxy-1-cyclopentylpiperidin-4-yl-X₃ | MH+ = 548<br>RT = 2.48<br>Method A |
| 9 | H₃C—X₁ | Cl—X₂ | H | H | 1-cyclopentylpiperidin-4-yl-X₃ | MH+ = 532<br>RT = 2.58<br>Method A |
| 10 | H₃C—X₁ | Cl—X₂ | H | H | 4-methoxy-1-cyclopentylpiperidin-4-yl-X₃ | MH+ = 562<br>RT = 2.64<br>Method A |
| 11 | H₃C—X₁ | H | H | H | 4-hydroxy-1-cyclopentylpiperidin-4-yl-X₃ | MH+ = 514<br>RT = 2.50<br>Method A |
| 12 | H₃C—X₁ | F—X₂ | H | H | 4-methoxy-1-methylpiperidin-4-yl-X₃ | MH+ = 492<br>RT = 2.41<br>Method A |

TABLE 1-continued

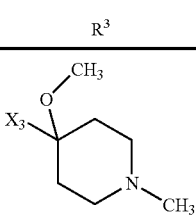

| Example | R¹ | R²ᵃ | R²ᵇ | R⁴ | R³ | analysis HPLC-MS |
|---|---|---|---|---|---|---|
| 13 | H₃C—X₁ | Cl—X₂ | H | H | 4-methoxy-1-methylpiperidin-4-yl (X₃) | MH+ = 508<br>RT = 2.50<br>Method A |
| 14 | H₃C—X₁ | Cl—X₂ | H | H | 4-hydroxy-1-isopropylpiperidin-4-yl (X₃) | MH+ = 522<br>RT = 2.34<br>Method A |
| 15 | H₃C—X₁ | Cl—X₂ | H | H | (S)-pyrrolidin-2-yl (X₃) | MH+ = 450<br>RT = 1.63<br>Method B |
| 16 | H₃C—X₁ | H | H | H | 1-cyclopentylpiperidin-4-yl (X₃) | MH+ = 498<br>RT = 2.26<br>Method A |
| 17 | H₃C—X₁ | F—X₂ | H | H | 4-hydroxy-1-isopropylpiperidin-4-yl (X₃) | MH+ = 506<br>RT = 2.27<br>Method A |
| 18 | H₃C—X₁ | Cl—X₂ | H | H | 1-isopropylpiperidin-4-yl (X₃) | MH+ = 506<br>RT = 2.55<br>Method A |
| 19 | H₃C—X₁ | Cl—X₂ | H | H | 1-(cyclopentylmethyl)piperidin-4-yl (X₃) | MH+ = 546<br>RT = 2.72<br>Method A |

TABLE 1-continued

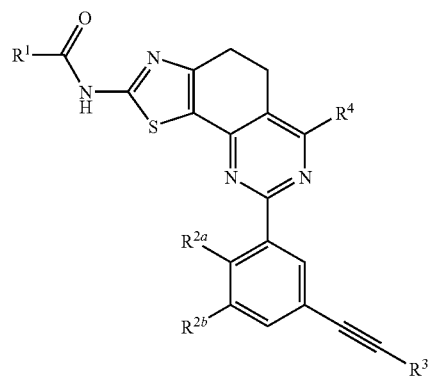

| Example | R¹ | R²ᵃ | R²ᵇ | R⁴ | R³ | analysis HPLC-MS |
|---|---|---|---|---|---|---|
| 20 | H₃C—X₁ | Cl—X₂ | H | H | X₃-(4-hydroxy-1-methylpiperidin-4-yl) | MH+ = 494<br>RT = 2.31<br>Method A |
| 21 | H₃C—X₁ | Cl—X₂ | H | H | X₃-(1-(methylamino)cyclohexyl) | MH+ = 492<br>RT = 2.52<br>Method A |
| 22 | H₃C—X₁ | Cl—X₂ | H | H | X₃-(1-aminocyclohexyl) | MH+ = 478<br>RT = 2.52<br>Method A |
| 23 | H₃C—X₁ | Cl—X₂ | H | H | X₃-(pyrrolidin-2-yl) | MH+ = 450<br>RT = 1.62<br>Method B |
| 24 | H₃C—X₁ | Cl—X₂ | H | H | X₃-CH₂-O-(quinuclidin-3-yl) | MH+ = 520<br>RT = 2.44<br>Method A |
| 25 | H₃C—X₁ | Cl—X₂ | H | H | X₃-CH₂-(pyrrolidin-1-yl) | MH+ = 466<br>RT = 2.34<br>Method A |
| 26 | H₃C—X₁ | Cl—X₂ | H | H | X₃-(1-(dimethylamino)cyclopentyl) | MH+ = 492<br>RT = 1.77<br>Method B |
| 27 | H₃C—X₁ | H | H | H | X₃-(1-methylpiperidin-4-yl) | MH+ = 444<br>RT = 2.48<br>Method A |

TABLE 1-continued

| Example | R¹ | R²ᵃ | R²ᵇ | R⁴ | R³ | analysis HPLC-MS |
|---|---|---|---|---|---|---|
| 28 | H₃C—X₁ | Cl—X₂ | H | H | X₃—CH₂—NH₂ | |
| 29 | H₃C—X₁ | Cl—X₂ | H | H | X₃—C(CH₃)₂—NH₂ | MH+ = 438 RT = 2.33 Method A |
| 30 | H₃C—X₁ | H | H | H | X₃—(4-hydroxy-1-isopropylpiperidinyl) | MH+ = 488 RT = 2.34 Method A |
| 31 | H₃C—X₁ | Cl—X₂ | H | H | X₃—CH₂—O—(1-acetylpiperidin-4-yl) | MH+ = 536 RT = 2.81 Method A |
| 32 | H₃C—X₁ | Cl—X₂ | H | H | X₃—(1-(ethylamino)cyclohexyl) | MH+ = 506 RT = 2.56 Method A |
| 33 | H₃C—X₁ | Cl—X₂ | H | H | X₃—(1-acetamidocyclohexyl) | MH+ = 520 RT = 3.03 Method A |
| 34 | H₃C—X₁ | Cl—X₂ | H | H | X₃—(1-pyrrolidin-1-yl-cyclohexyl) | MH+ = 532 RT = 2.63 Method A |

TABLE 1-continued
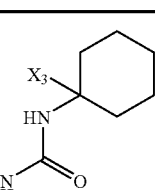
| Example | R¹ | R²ᵃ | R²ᵇ | R⁴ | R³ | analysis HPLC-MS |
|---|---|---|---|---|---|---|
| 35 | H₃C—X₁ | Cl—X₂ | H | H | 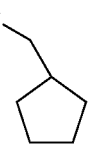 | MH+ = 535<br>RT = 2.98<br>Method A |
| 36 | H₃C—X₁ | H | H | H | 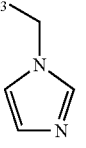 | MH+ = 512<br>RT = 2.75<br>Method A |
| 37 | H₃C—X₁ | Cl—X₂ | H | H | 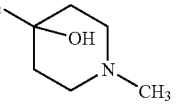 | MH+ = 461<br>RT = 2.39<br>Method A |
| 38 | H₃C—X₁ | H | H | H | 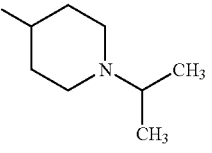 | MH+ = 460<br>RT = 2.30<br>Method A |
| 39 | H₃C—X₁ | H | H | H | 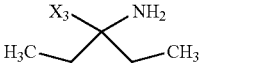 | MH+ = 472<br>RT = 2.55<br>Method A |
| 40 | H₃C—X₁ | Cl—X₂ | H | H | 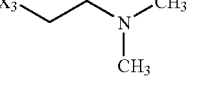 | MH+ = 466<br>RT = 2.44<br>Method A |
| 41 | H₃C—X₁ | Cl—X₂ | H | H | X₃—CH₂CH₂—N(CH₃)CH₃ | MH+ = 452<br>RT = 2.44<br>Method A |

TABLE 1-continued

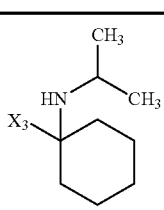

| Example | R¹ | R²ᵃ | R²ᵇ | R⁴ | R³ | analysis HPLC-MS |
|---|---|---|---|---|---|---|
| 42 | H₃C—X₁ | Cl—X₂ | H | H | (1-(1-methylethylamino)cyclohexyl)-X₃ | MH+ = 520<br>RT = 2.61<br>Method A |
| 43 | H₃C—X₁ | Cl—X₂ | H | H | X₃—CH=CH₂ | MH+ = 466<br>RT = 2.46<br>Method A |
| 44 | H₃C—X₁ | Cl—X₂ | H | H | (1-hydroxycyclohexyl)-X₃ | MH+ = 479<br>RT = 3.09<br>Method A |
| 45 | H₃C—X₁ | Cl—X₂ | H | H | (1-(dimethylamino)cyclohexyl)-X₃ | MH+ = 506<br>RT = 2.62<br>Method A |
| 46 | H₃C—X₁ | Cl—X₂ | H | H | X₃—CH₂CH₂OH | MH+ = 425<br>RT = 2.65<br>Method A |
| 47 | H₃C—X₁ | H | H | H | X₃—CH₂—N(CH₃)₂ | MH+ = 404<br>RT = 2.35<br>Method A |
| 48 | H₃C—X₁ | H | H | H | X₃—CH₂—NH—CH₃ | MH+ = 390<br>RT = 2.30<br>Method A |
| 49 | H₃C—X₁ | Cl—X₂ | H | H | (1-methyl-1H-imidazol-5-yl)-X₃ | MH+ = 461<br>RT = 2.38<br>Method A |
| 50 | H₃C—X₁ | Cl—X₂ | H | H | X₃—CH₂-cyclopentyl | MH+ = 463<br>RT = 3.90<br>Method A |

TABLE 1-continued

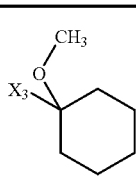

| Example | R¹ | R²ᵃ | R²ᵇ | R⁴ | R³ | analysis HPLC-MS |
|---|---|---|---|---|---|---|
| 51 | H₃C—X₁ | F—X₂ | H | H | 1-methoxycyclohexyl-X₃ | MH+ = 477<br>RT = 3.63<br>Method A |
| 52 | H₃C—X₁ | Cl—X₂ | H | H | 1-methoxycyclohexyl-X₃ | MH+ = 493<br>RT = 3.73<br>Method A |
| 53 | H₃C—X₁ | H | Cl—X₃ | H | 4-aminocyclohexyl-X₃ | MH+ = 478<br>RT = 2.84<br>Method A |
| 54 | H₃C—X₁ | H | Cl—X₃ | H | X₃-CH₂-N(CH₃)₂ | MH+ = 438<br>RT = 2.60<br>Method A |
| 55 | H₃C—X₁ | H | Cl—X₃ | H | X₃-(1-cyclopentylpiperidin-4-yl) | MH+ = 432<br>RT = 2.97<br>Method A |
| 56 | H₃C—X₁ | Cl—X₂ | H | H | X₃-cyclohexyl | MH+ = 462<br>RT = 3.95<br>Method A |
| 57 | H₃C—X₁ | Cl—X₂ | H | H | X₃-CH₂-O-CH₃ | MH+ = 424<br>RT = 3.06<br>Method A |

TABLE 1-continued

| Example | R¹ | R²ᵃ | R²ᵇ | R⁴ | R³ | analysis HPLC-MS |
|---|---|---|---|---|---|---|
| 58 | H₃C—X₁ | Cl–X₂ | H | H | X₃-(4-hydroxy-4-methylcyclohexyl with CH₃) | MH+ = 507, RT = 2.24, Method B |
| 59 | H₃C—X₁ | Cl–X₂ | H | H | X₃-(pyridin-3-yl) | MH+ = 458, RT = 1.79, Method B |
| 60 | H₃C—X₁ | Cl–X₂ | H | H | X₃-phenyl | MH+ = 457, RT = 2.39, Method B |
| 61 | H₃C—X₁ | Cl–X₂ | H | H | X₃-(pyridin-2-yl) | MH+ = 458, RT = 1.78, Method B |
| 62 | H₃C—X₁ | Cl–X₂ | H | H | X₃-CH₂CH₂-piperidin-1-yl | MH+ = 493, RT = 2.50, Method A |
| 63 | H₃C—X₁ | Cl–X₂ | H | H | X₃-CH₂CH₂-pyrrolidin-1-yl | MH+ = 478, RT = 2.42, Method A |
| 64 | H₃C—X₁ | Cl–X₂ | H | H | X₃-CH₂CH₂-NH-CH(CH₃)₂ | MH+ = 466, RT = 2.43, Method A |
| 65 | H₃C—X₁ | Cl–X₂ | H | H | X₃-CH₂CH₂-NH-CH₂-cyclopentyl | MH+ = 506, RT = 2.66, Method A |

TABLE 1-continued

| Example | R¹ | R²ᵃ | R²ᵇ | R⁴ | R³ | analysis HPLC-MS |
|---|---|---|---|---|---|---|
| 66 | H₃C—X₁ | Cl—X₂ | H | H | X₃—CH₂CH₂—N(morpholine) | MH+ = 495<br>RT = 2.39<br>Method A |
| 67 | H₃C—X₁ | Cl—X₂ | H | H | X₃—CH₂CH₂—N(N-methylpiperazine) | MH+ = 507<br>RT = 2.23<br>Method A |
| 68 | H₃C—X₁ | Cl—X₂ | H | H | X₃—CH₂CH₂—N(CH₃)(CH(CH₃)₂) | MH+ = 480<br>RT = 2.38<br>Method A |
| 69 | H₃C—X₁ | Cl—X₂ | H | H | X₃—CH₂CH₂—N(piperidine-4-N(CH₃)₂) | MH+ = 535<br>RT = 2.26<br>Method A |
| 70 | H₃C—X₁ | Cl—X₂ | H | H | X₃—CH₂CH₂—N(CH₃)C(O)NHCH₃ | MH+ = 495<br>RT = 1.80<br>Method B |
| 71 | H₃C—X₁ | Cl—X₂ | H | H | X₃—CH₂CH₂—N(CH₃)C(O)CH₃ | MH+ = 480<br>RT = 1.84<br>Method B |

Example 72

N-(8-{5-[3-(acetyl-methyl-amino)-prop-1-ynyl]-2-chloro-phenyl}-4,5-dihydro-thiazolo[4,5-h]quinazolin-2-yl)-acetamide

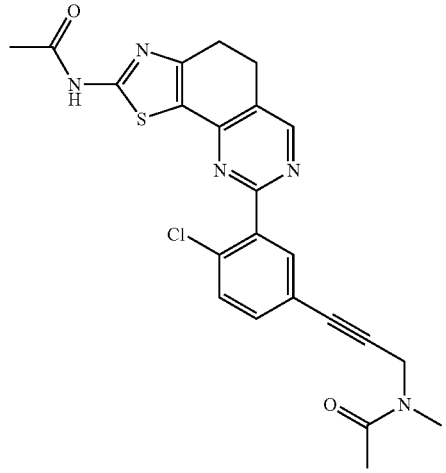

25 μl acetic acid and 80 mg (0.25 mmol) O-(1H-benzotriazol-1-yl)-N,N,N',N'-tetramethyluronium tetrafluoroborate (TBTU) are placed in 5 mL dichloromethane, combined with 65 μL diisopropylethylamine and stirred for 0.5 hours at ambient temperature. 65 mg (0.15 mmol) N-{8-[2-chloro-5-(3-methylamino-prop-1-ynyl)-phenyl]-4,5-dihydro-thiazolo[4,5-h]quinazolin-2-yl}-acetamide are added, then the mixture is stirred for 16 hours at ambient temperature. Then the reaction mixture is extracted with potassium carbonate solution and dichloromethane. The organic phase is dried and evaporated to dryness. The residue is purified by chromatography.

Yield: 12 mg (MH+=466; RT=2.70; Method A)

The following compounds may be prepared analogously, starting from N-{8-[2-chloro-5-(3-methylamino-prop-1-ynyl)-phenyl]-4,5-dihydro-thiazolo[4,5-h]quinazolin-2-yl}-acetamide (Example 1) or N-{8-[5-(3-amino-prop-1-ynyl)-2-chloro-phenyl]-4,5-dihydro-thiazolo[4,5-h]quinazolin-2-yl}-acetamide (Example 28).

TABLE 2

| Example | R¹ | R²ᵃ | R²ᵇ | R⁴ | R³ | analysis HPLC-MS |
|---------|----|----|----|----|----|------------------|
| 72 | H₃C—X₁ | Cl—X₂ | H | H | X₃—CH₂—C(O)—N(CH₃)—C(O)CH₃ | MH+ = 466 RT = 2.70 Method A |
| 73 | H₃C—X₁ | Cl—X₂ | H | H | X₃—CH₂—C(O)—NH—CH₂—C(CH₃)₂—CH₃ | MH+ = 508 RT = 3.01 Method A |

TABLE 2-continued

| Example | R¹ | R²ᵃ | R²ᵇ | R⁴ | R³ | analysis HPLC-MS |
|---|---|---|---|---|---|---|
| 74 | H₃C—X₁ | H | H | H | X₃–CH₂–NH–C(O)–cyclopentyl | MH+ = 472<br>RT = 2.99<br>Method A |
| 75 | H₃C—X₁ | Cl–X₂ | H | H | X₃–CH₂–N(CH₃)–C(O)–CH(CH₃)₂ | MH+ = 494<br>RT = 2.96<br>Method A |
| 76 | H₃C—X₁ | H | H | H | X₃–CH₂–NH–C(O)–CH₂–C(CH₃)₃ | MH+ = 474<br>RT = 3.10<br>Method A |
| 77 | H₃C—X₁ | Cl–X₂ | H | H | X₃–CH₂–NH–C(O)–CH₂–imidazol-1-yl | MH+ = 518<br>RT = 2.31<br>Method A |
| 78 | H₃C—X₁ | Cl–X₂ | H | H | X₃–CH₂–NH–C(O)–cyclohexyl | MH+ = 502<br>RT = 3.05<br>Method A |

TABLE 2-continued
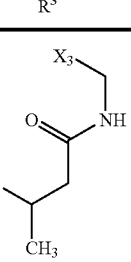
| Example | R¹ | R²ᵃ | R²ᵇ | R⁴ | R³ | analysis HPLC-MS |
|---|---|---|---|---|---|---|
| 79 | H₃C—X₁ | Cl—X₂ | H | H | 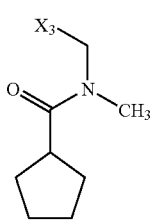 | MH+ = 494 RT = 2.88 Method A |
| 80 | H₃C—X₁ | Cl—X₂ | H | H | 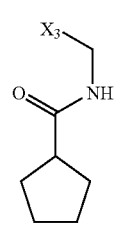 | MH+ = 520 RT = 3.17 Method A |
| 81 | H₃C—X₁ | Cl—X₂ | H | H | 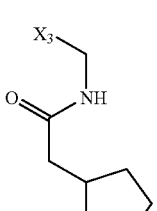 | MH+ = 506 RT = 2.97 Method A |
| 82 | H₃C—X₁ | Cl—X₂ | H | H | 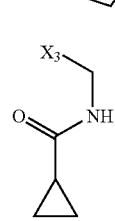 | MH+ = 520 RT = 3.08 Method A |
| 83 | H₃C—X₁ | Cl—X₂ | H | H | | MH+ = 478 RT = 2.80 Method A |

TABLE 2-continued
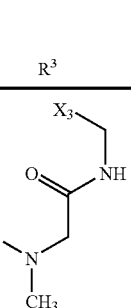
| Example | R¹ | R²ᵃ | R²ᵇ | R⁴ | R³ | analysis HPLC-MS |
|---|---|---|---|---|---|---|
| 84 | H₃C—X₁ | Cl—X₂ | H | H | 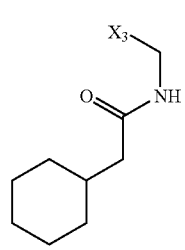 | MH+ = 495<br>RT = 2.29<br>Method A |
| 85 | H₃C—X₁ | Cl—X₂ | H | H | 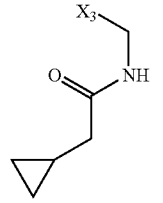 | MH+ = 534<br>RT = 3.17<br>Method A |
| 86 | H₃C—X₁ | Cl—X₂ | H | H | 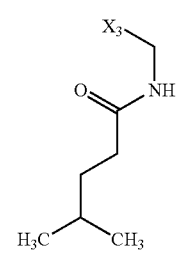 | MH+ = 492<br>RT = 2.79<br>Method A |
| 87 | H₃C—X₁ | Cl—X₂ | H | H | 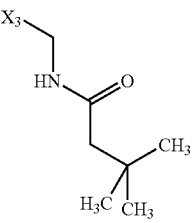 | MH+ = 508<br>RT = 3.04<br>Method A |
| 88 | H₃C—X₁ | H | Cl—X₃ | H | 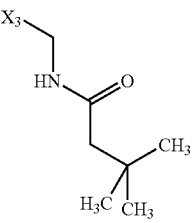 | MH+ = 508<br>RT = 3.57<br>Method A |

TABLE 2-continued
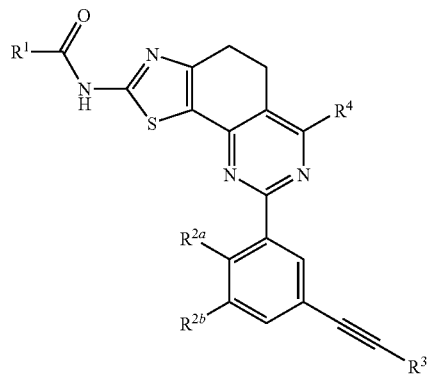
| Example | R¹ | R²ᵃ | R²ᵇ | R⁴ | R³ | analysis HPLC-MS |
|---|---|---|---|---|---|---|
| 89 | H₃C—X₁ | H | H | H | X₃–CH₂–NH–C(O)–CH₃ | MH+ = 418 RT = 2.60 Method A |
| 90 | H₃C—X₁ | Cl–X₂ | H | H | X₃–CH₂–NH–C(O)–CH(CH₃)₂ | MH+ = 480 RT = 2.82 Method A |
| 91 | H₃C—X₁ | Cl–X₂ | H | H | X₃–CH₂–NH–C(O)–CH₃ | MH+ = 452 RT = 2.58 Method A |
| 92 | H₃C—X₁ | H | H | H | X₃–CH₂–NH–C(O)–(1-methylpiperidin-4-yl) | MH+ = 501 RT = 2.36 Method A |
| 93 | H₃C—X₁ | Cl–X₂ | H | H | X₃–CH₂–NH–C(O)–CH₂–(1-methylpiperidin-4-yl) | MH+ = 549 RT = 2.32 Method A |

TABLE 2-continued

| Example | R¹ | R²ᵃ | R²ᵇ | R⁴ | R³ | analysis HPLC-MS |
|---|---|---|---|---|---|---|
| 94 | H₃C—X₁ | Cl—X₂ | H | H | X₃—CH₂—C(=O)—NH—CH₂CH₂—cyclopentyl | MH+ = 534 RT = 3.21 Method A |

Example 95

N-(8-{2-chloro-5-[3-(methanesulphonyl-methyl-amino)-prop-1-ynyl]-phenyl}-4,5-dihydro-thiazolo[4,5-h]quinazolin-2-yl)-acetamide

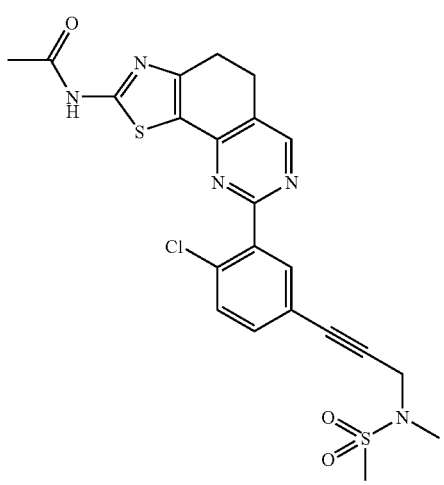

A mixture of 65 mg (0.15 mmol) N-{8-[2-chloro-5-(3-methylamino-prop-1-ynyl)-phenyl]-4,5-dihydro-thiazolo[4,5-h]quinazolin-2-yl}-acetamide, 100 μL triethylamine and 30 μL methanesulphonic acid chloride in 1 mL dichloromethane is stirred overnight at ambient temperature. The reaction mixture is washed with saturated aqueous sodium hydrogen carbonate solution and the organic phase is evaporated down. The residue remaining is stirred with ether. Yield: 55 mg yellow solid (MH+=502; RT=2.98; Method A)

The following compounds may be prepared analogously, starting from N-{8-[2-chloro-5-(3-methylamino-prop-1-ynyl)-phenyl]-4,5-dihydro-thiazolo[4,5-h]quinazolin-2-yl}-acetamide (Example 1) or N-{8-[5-(3-amino-prop-1-ynyl)-2-chloro-phenyl]-4,5-dihydro-thiazolo[4,5-h]quinazolin-2-yl}-acetamide (Example 28).

TABLE 3

| Example | R¹ | R²ᵃ | R²ᵇ | R⁴ | R³ | analysis HPLC-MS |
|---|---|---|---|---|---|---|
| 95 | H₃C—X₁ | Cl—X₂ | H | H | X₃—CH₂—N(CH₃)SO₂CH₃ | MH+ = 486, RT = 2.90, Method A |
| 96 | H₃C—X₁ | Cl—X₂ | H | H | X₃—CH₂—NH—SO₂—CH₂CH₃ | MH+ = 502, RT = 3.07, Method A |
| 97 | H₃C—X₁ | Cl—X₂ | H | H | X₃—CH₂—N(CH₃)SO₂-cyclopropyl | MH+ = 528, RT = 3.18, Method A |
| 98 | H₃C—X₁ | Cl—X₂ | H | H | X₃—CH₂—NH—SO₂-cyclopropyl | MH+ = 514, RT = 2.86, Method A |
| 99 | H₃C—X₁ | Cl—X₂ | H | H | X₃—CH₂—N(CH₃)SO₂—CH(CH₃)₂ | MH+ = 530, RT = 3.18, Method A |
| 100 | H₃C—X₁ | Cl—X₂ | H | H | X₃—CH₂—N(CH₃)SO₂—N(CH₃)₂ | MH+ = 531, RT = 3.15, Method A |

TABLE 3-continued

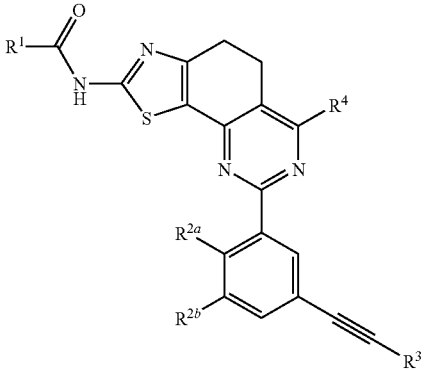

| Example | R¹ | R²ᵃ | R²ᵇ | R⁴ | R³ | analysis HPLC-MS |
|---|---|---|---|---|---|---|
| 101 | H₃C—X₁ | Cl–X₂ | H | H | (X₃-CH₂-NH-SO₂-CH(CH₃)₂) | MH+ = 516<br>RT = 2.88<br>Method A |
| 102 | H₃C—X₁ | Cl–X₂ | H | H | (X₃-CH₂-NH-SO₂-N(CH₃)₂) | MH+ = 517<br>RT = 2.91<br>Method A |
| 103 | H₃C—X₁ | Cl–X₂ | H | H | (X₃-CH₂-NH-SO₂-NH₂) | MH+ = 489<br>RT = 1.74<br>Method B |
| 104 | H₃C—X₁ | Cl–X₂ | H | H | (X₃-CH₂-NH-SO₂-CH₂-CF₃) | MH+ = 556<br>RT = 2.86<br>Method A |
| 105 | H₃C—X₁ | Cl–X₂ | H | H | (X₃-CH₂-NH-SO₂-CH₃) | MH+ = 488<br>RT = 2.73<br>Method A |
| 106 | H₃C—X₁ | Cl–X₂ | H | H | (X₃-CH₂-NH-SO₂-N(CH₃)(CH₂CH₃)) | MH+ = 530<br>RT = 1.99<br>Method B |

TABLE 3-continued
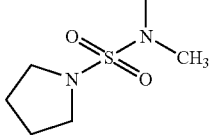
| Example | R¹ | R²ᵃ | R²ᵇ | R⁴ | R³ | analysis HPLC-MS |
|---|---|---|---|---|---|---|
| 107 | H₃C—X₁ | Cl—X₂ | H | H | 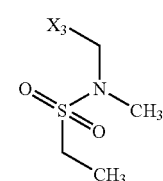 | MH+ = 557<br>RT = 3.25<br>Method A |
| 108 | H₃C—X₁ | Cl—X₂ | H | H | 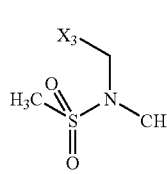 | MH+ = 516<br>RT = 3.08<br>Method A |
| 109 | H₃C—X₁ | H | Cl—X₃ | H | 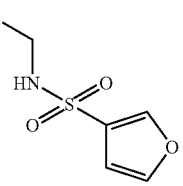 | MH+ = 502<br>RT = 3.47<br>Method A |
| 110 | H₃C—X₁ | Cl—X₂ | H | H | 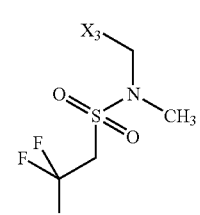 | MH+ = 540<br>RT = 1.96<br>Method B |
| 111 | H₃C—X₁ | Cl—X₂ | H | H | 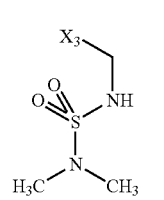 | MH+ = 570<br>RT = 3.25<br>Method A |
| 112 | H₃C—X₁ | H | H | H |  | MH+ = 483<br>RT = 2.98<br>Method A |

TABLE 3-continued

| Example | R¹ | R²ᵃ | R²ᵇ | R⁴ | R³ | analysis HPLC-MS |
|---|---|---|---|---|---|---|
| 113 | H₃C—X₁ | Cl–X₂ | H | H | X₃–CH₂–NH–SO₂–N(CH₂CH₃)₂ (diethylaminosulfonamide) | MH+ = 545<br>RT = 3.15<br>Method A |
| 114 | H₃C—X₁ | Cl–X₂ | H | H | X₃–CH₂–NH–SO₂–morpholine | MH+ = 558<br>RT = 1.88<br>Method B |
| 115 | H₃C—X₁ | Cl–X₂ | H | H | X₃–CH₂–NH–SO₂–pyrrolidine | MH+ = 543<br>RT = 3.02<br>Method A |
| 116 | H₃C—X₁ | Cl–X₂ | H | H | X₃–CH₂–NH–SO₂–phenyl | MH+ = 550<br>RT = 2.03<br>Method B |
| 117 | H₃C—X₁ | H | H | H | X₃–CH₂–NH–SO₂–cyclopropyl | MH+ = 480<br>RT = 2.95<br>Method A |
| 118 | H₃C—X₁ | H | Cl–X₃ | H | X₃–CH₂–NH–SO₂–CH₃ | MH+ = 488<br>RT = 3.21<br>Method A |

TABLE 3-continued

| Example | R¹ | R²ᵃ | R²ᵇ | R⁴ | R³ | analysis HPLC-MS |
|---|---|---|---|---|---|---|
| 119 | H₃C—X₁ | Cl—X₂ | H | H | X₃-CH₂-NH-SO₂-CH₂-phenyl | MH+ = 564<br>RT = 2.05<br>Method B |
| 120 | H₃C—X₁ | Cl—X₂ | H | H | X₃-CH₂-NH-SO₂-cyclohexyl | MH+ = 556<br>RT = 3.20<br>Method A |
| 121 | H₃C—X₁ | Cl—X₂ | H | H | X₃-CH₂-N(CH₃)-SO₂-morpholino | MH+ = 573<br>RT = 2.01<br>Method B |
| 122 | H₃C—X₁ | Cl—X₂ | H | H | X₃-CH₂-NH-SO₂-CF₃ | MH+ = 542<br>RT = 2.10<br>Method B |
| 123 | H₃C—X₁ | Cl—X₂ | H | H | X₃-CH₂-NH-SO₂-N(4-methoxypiperidinyl) | MH+ = 587<br>RT = 1.96<br>Method B |

Example 124

N-(8-{2-chloro-5-[3-(3-methyl-ureido)-prop-1-ynyl]-phenyl}-4,5-5 dihydro-thiazolo[4,5-h]quinazolin-2-yl)-acetamide

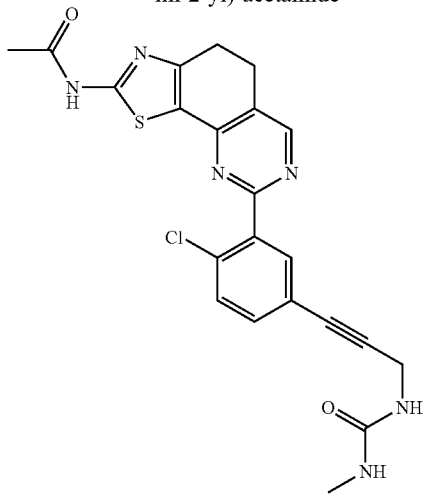

A mixture of 150 mg (0.37 mmol) N-{8-[5-(3-amino-prop-1-ynyl)-2-chloro-phenyl]-4,5-dihydro-thiazolo[4,5-h]quinazolin-2-yl}-acetamide, 0.1 mL (0.68 mmol) triethylamine and 40 mg (0.70 mmol) methylisocyanate in 4 mL acetonitrile is stirred overnight at ambient temperature. The precipitated solid is suction filtered and washed with ether.

Yield: 133 mg yellow solid (mp.: 133° C.).

The following compounds may be prepared analogously, starting from N-{8-[2-chloro-5-(3-methylamino-prop-1-ynyl)-phenyl]-4,5-dihydro-thiazolo[4,5-h]quinazolin-2-yl}-acetamide (Example 1).

TABLE 4

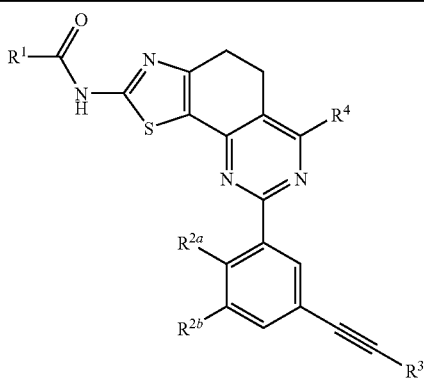

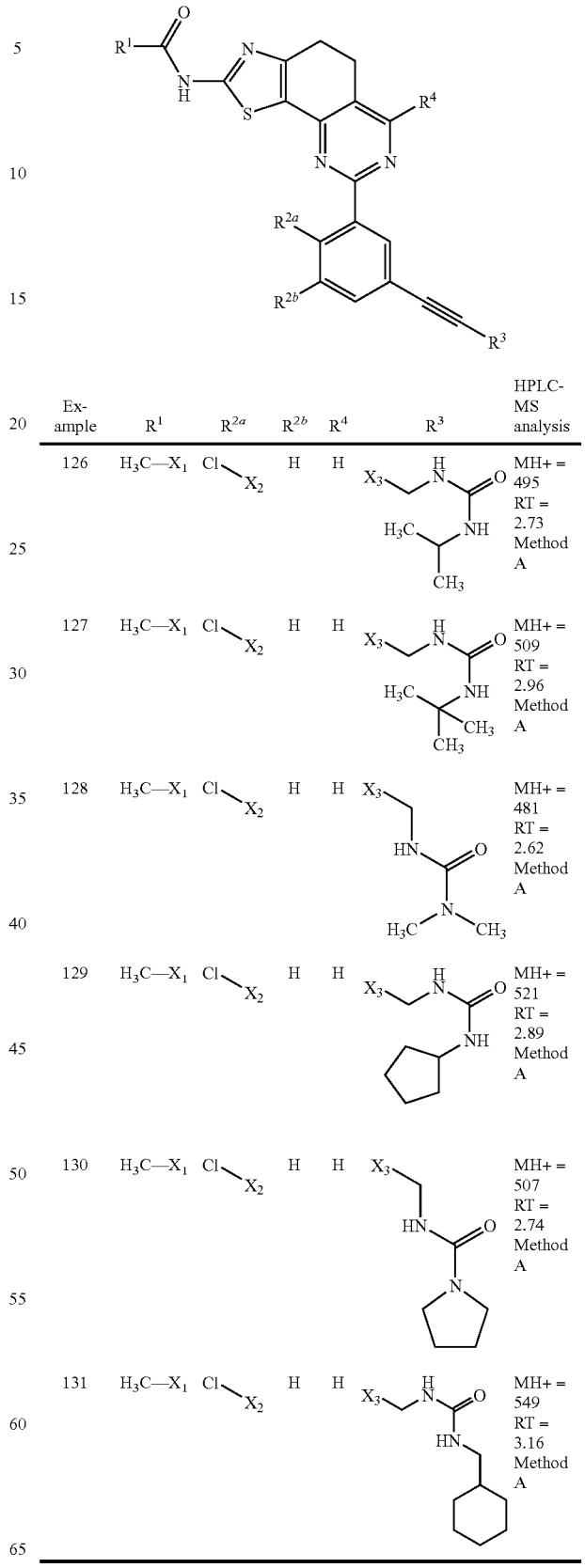

| Example | $R^1$ | $R^{2a}$ | $R^{2b}$ | $R^4$ | $R^3$ | HPLC-MS analysis |
|---|---|---|---|---|---|---|
| 124 | $H_3C-X_1$ | $Cl-X_2$ | H | H | $X_3$—CH$_2$—NH—C(O)—NH—CH$_3$ | MH+ = 467, RT = 2.53, Method A |
| 125 | $H_3C-X_1$ | $Cl-X_2$ | H | H | $X_3$—CH$_2$—NH—C(O)—NH—CH$_2$CH$_3$ | MH+ = 481, RT = 2.60, Method A |
| 126 | $H_3C-X_1$ | $Cl-X_2$ | H | H | $X_3$—CH$_2$—NH—C(O)—NH—CH(CH$_3$)$_2$ | MH+ = 495, RT = 2.73, Method A |
| 127 | $H_3C-X_1$ | $Cl-X_2$ | H | H | $X_3$—CH$_2$—NH—C(O)—NH—C(CH$_3$)$_3$ | MH+ = 509, RT = 2.96, Method A |
| 128 | $H_3C-X_1$ | $Cl-X_2$ | H | H | $X_3$—CH$_2$—NH—C(O)—N(CH$_3$)$_2$ | MH+ = 481, RT = 2.62, Method A |
| 129 | $H_3C-X_1$ | $Cl-X_2$ | H | H | $X_3$—CH$_2$—NH—C(O)—NH—cyclopentyl | MH+ = 521, RT = 2.89, Method A |
| 130 | $H_3C-X_1$ | $Cl-X_2$ | H | H | $X_3$—CH$_2$—NH—C(O)—pyrrolidin-1-yl | MH+ = 507, RT = 2.74, Method A |
| 131 | $H_3C-X_1$ | $Cl-X_2$ | H | H | $X_3$—CH$_2$—NH—C(O)—NH—CH$_2$-cyclohexyl | MH+ = 549, RT = 3.16, Method A |

Example 132

N-{8-[2-chloro-5-(3-cyclopentylamino-prop-1-ynyl)-phenyl]-4,5-dihydro-thiazolo[4,5-h]quinazolin-2-yl}-acetamide

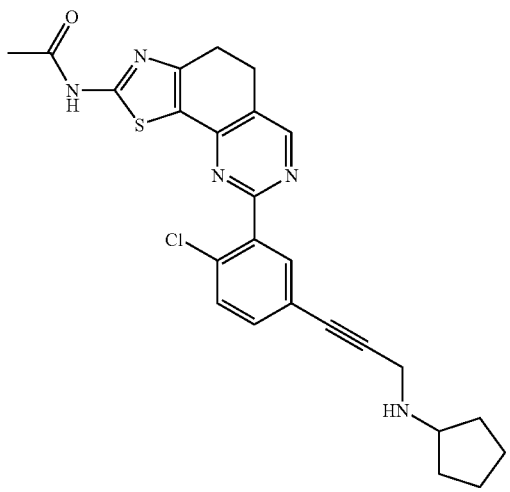

Under a protective gas atmosphere 2.0 g (4.1 mmol) N-[8-(2-chloro-5-iodo-phenyl)-4,5-dihydro-thiazolo[4,5-h] quinazolin-2-yl]-acetamide and 0.7 mL diisopropylethylamine are dissolved in 50 mL THF and combined with 0.7 ml (11.6 mmol) propargylalcohol, 290 mg (0.4 mmol) triphenylphosphine palladium (II)-chloride and 79 mg (0.4 mmol) copper(l)-iodide. The reaction mixture is heated to 80° C. for 1.5 hours and then evaporated down. The residue is stirred with dichloromethane and the solid obtained is suction filtered.

Yield: 1.7 g yellow solid.

200 mg (0.49 mmol) of the intermediate described above and 0.1 mL triethylamine are suspended in 20 mL dichloromethane and at 0° C. combined with 50 μL methanesulphonic acid chloride. After three hours the reaction mixture is combined with another 0.2 mL methanesulphonic acid chloride and a spatula tip of 4-dimethylaminopyridine and stirred for 30 minutes at ambient temperature. The mixture is concentrated by rotary evaporation and used directly in the next reaction. Yield: 120 mg viscous yellow oil.

60 mg (0.12 mmol) of the methanesulphonate intermediate described above are dissolved in 1 mL dimethylformamide and combined with 13 mg (0.15 mmol) cyclopentylamine. The reaction mixture is stirred overnight at 50° C. Then another 150 mg cyclopentylamine are added and the mixture is stirred for two hours at 70° C. The mixture is purified by RP-HPLC. Yield: 22 mg of light yellow solid.

The following compounds may be prepared analogously, starting from N-{8-[2-chloro-5-(3-methylamino-prop-1-ynyl)-phenyl]-4,5-dihydro-thiazolo[4,5-h]quinazolin-2-yl}-acetamide (Example 1).

TABLE 5

| Example | $R^1$ | $R^{2a}$ | $R^{2b}$ | $R^4$ | $R^3$ | HPLC-MS analysis |
|---|---|---|---|---|---|---|
| 132 | H₃C—X₁ | Cl—X₂ | H | H | X₃—CH₂—NH—cyclopentyl | MH+ = 478<br>RT = 2.46<br>Method A |
| 133 | H₃C—X₁ | Cl—X₂ | H | H | X₃—CH₂—NH—CH₂—cyclopentyl | MH+ = 493<br>RT = 2.57<br>Method A |
| 134 | H₃C—X₁ | Cl—X₂ | H | H | X₃—CH₂—(3-oxopiperazin-1-yl) | |

TABLE 5-continued

| Example | R¹ | R²ᵃ | R²ᵇ | R⁴ | R³ | HPLC-MS analysis |
|---|---|---|---|---|---|---|
| 135 | H₃C—X₁ | Cl—X₂ | H | H | X₃—NH—CH(CH₃)₂ | MH+ = 452<br>RT = 2.40<br>Method A |
| 136 | H₃C—X₁ | Cl—X₂ | H | H | X₃—NH—CH₂—CH(CH₃)₂ | MH+ = 467<br>RT = 2.44<br>Method A |
| 137 | H₃C—X₁ | Cl—X₂ | H | H | X₃—N(piperazine)—cyclopentyl | MH+ = 547<br>RT = 2.46<br>Method A |
| 138 | H₃C—X₁ | Cl—X₂ | H | H | X₃—N(CH₃)₂ | MH+ = 438<br>RT = 2.30<br>Method A |
| 139 | H₃C—X₁ | Cl—X₂ | H | H | X₃—CH₂—thiomorpholine-1,1-dioxide | MH+ = 528<br>RT = 2.54<br>Method A |
| 140 | H₃C—X₁ | Cl—X₂ | H | H | X₃—NH—(1-methylpiperidin-4-yl) | MH+ = 507<br>RT = 2.19<br>Method A |
| 141 | H₃C—X₁ | Cl—X₂ | H | H | X₃—N(piperazinone)—N-CH₃ | MH+ = 507<br>RT = 2.28<br>Method A |
| 142 | H₃C—X₁ | Cl—X₂ | H | H | X₃—N(piperazine)—CH(CH₃)₂ | MH+ = 521<br>RT = 2.35<br>Method A |

TABLE 5-continued

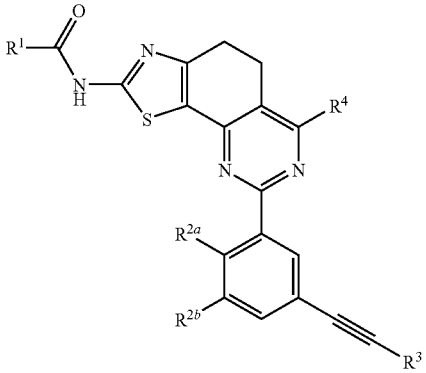

| Example | R¹ | R²ᵃ | R²ᵇ | R⁴ | R³ | HPLC-MS analysis |
|---|---|---|---|---|---|---|
| 143 | H₃C—X₁ | Cl–X₂ | H | H | piperidine-4-carboxamide with X₃–CH₂– on N | |
| 144 | H₃C—X₁ | Cl–X₂ | H | H | 4-acetylpiperazine with X₃–CH₂– on N | |
| 145 | H₃C—X₁ | Cl–X₂ | H | H | X₃–CH₂–N(CH₃)–CH(CH₃)₂ | MH+ = 466 RT = 2.38 Method A |
| 146 | H₃C—X₁ | Cl–X₂ | H | H | X₃–CH₂–NH–CH₂CH₂–(pyrrolidin-1-yl) | MH+ = 507 RT = 1.79 Method A |
| 147 | H₃C—X₁ | Cl–X₂ | H | H | 4-(dimethylamino)piperidine with X₃–CH₂– on N | |
| 148 | H₃C—X₁ | Cl–X₂ | H | H | X₃–CH₂–NH–CH₂–(pyridin-2-yl) | MH+ = 501 RT = 1.65 Method B |
| 149 | H₃C—X₁ | Cl–X₂ | H | H | X₃–CH₂–NH–CH₂–(3-methylpyridin-2-yl) | MH+ = 515 RT = 1.72 Method B |
| 150 | H₃C—X₁ | Cl–X₂ | H | H | 4-methylpiperazine with X₃–CH₂– on N | MH+ = 493 RT = 2.28 Method A |

TABLE 5-continued

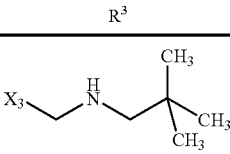

| Ex-ample | R¹ | R²ᵃ | R²ᵇ | R⁴ | R³ | HPLC-MS analysis |
|---|---|---|---|---|---|---|
| 151 | H₃C—X₁ | Cl—X₂ | H | H | X₃—CH₂—NH—C(CH₃)₂—CH₃ | MH+ = 480<br>RT = 2.54<br>Method A |
| 152 | H₃C—X₁ | Cl—X₂ | H | H | X₃—CH₂—N(thiomorpholine S-oxide) | |
| 153 | H₃C—X₁ | Cl—X₂ | H | H | X₃—CH₂—N(CH₃)—CH₂—CH(CH₃)₂ | MH+ = 480<br>RT = 1.71<br>Method B |
| 154 | H₃C—X₁ | Cl—X₂ | H | H | X₃—CH₂—NH—CH₂—cyclopropyl | MH+ = 464<br>RT = 1.68<br>Method B |

Example 155

N-[8-(2-chloro-5-piperidin-4-ylethynyl-phenyl)-4,5-dihydro-thiazolo[4,5-h]quinazolin-2-yl]-acetamide

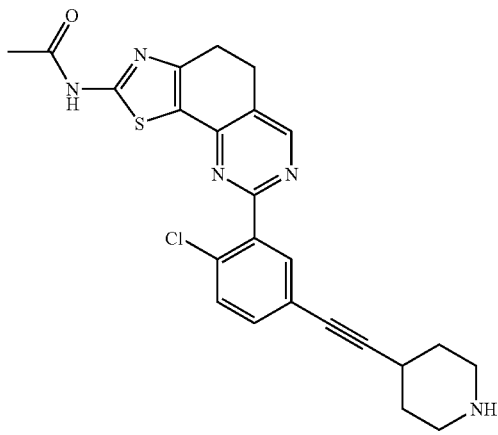

2.0 g (4.0 mmol) N-[8-(2-chloro-5-iod-phenyl)-4,5-dihydro-thiazolo[4,5-h]quinazolin-2-yl]-acetamide are placed in 50 mL tetrahydrofuran under an argon atmosphere and combined with 1.5 g (7 mmol) tert-butyl 4-ethynyl-piperidine-1-carboxylate and 0.5 ml (3 mmol) diisopropylethylamine. The mixture is kept free from oxygen and 78 mg (0.1 mmol) triphenylphosphine palladium(II)-chloride and 21 mg (0.1 mmol) copper(I)-iodide are added. The mixture is stirred for 5 hours at 80° C. After cooling to ambient temperature the reaction mixture is combined with dichloromethane and washed with dilute ammonia solution. The organic phase is dried and evaporated to dryness. The residue is purified by chromatography, corresponding fractions are combined and freeze-dried. The intermediate product obtained is stirred for 2 hours in ethereal hydrochloric acid, suction filtered and dried. Yield: 65 mg (m.p.: 162° C.; MH+=430; RT=3.72; Method A)

Example 156

N-{8-[5-(1-acetyl-piperidin-4-ylethynyl)-2-chloro-phenyl]-4,5-dihydro-thiazolo[4,5-h]quinazolin-2-yl}-acetamide

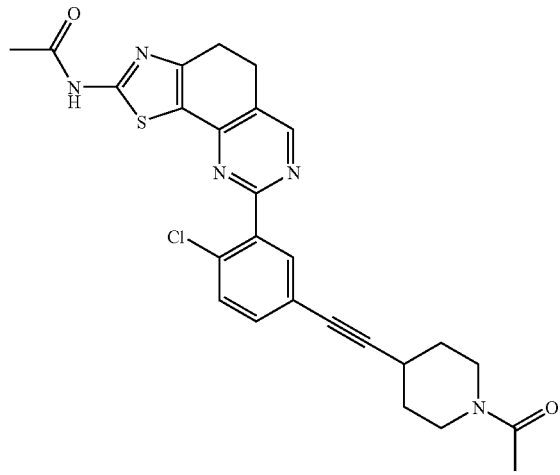

7 μl acetic acid and 50 mg (0.16 mmol) O-(1H-benzotriazol-1-yl)-N,N,N',N'-tetramethyluronium tetrafluoroborate (TBTU) are placed in 5 mL dichloromethane, combined with 32 μl diisopropylethylamine and stirred for 0.5 hours at ambient temperature. 60 mg (0.13 mmol) N-[8-(2-chloro-5-piperidin-4-ylethynyl-phenyl)-4,5-dihydro-thiazolo[4,5-h]quinazolin-2-yl]-acetamide (Example 155) are added, then the mixture is stirred for 16 hours at ambient temperature. Then the reaction mixture is extracted with potassium carbonate solution and dichloromethane. The organic phase is dried and evaporated to dryness. The residue is purified by chromatography.

Yield: 15 mg (MH+=506; RT=2.87; Method A)

The following Examples may be prepared analogously:

TABLE 6

| Example | $R^1$ | $R^{2a}$ | $R^{2b}$ | $R^4$ | $R^3$ | HPLC-MS analysis |
|---------|-------|----------|----------|-------|-------|------------------|
| 156 | $H_3C$—$X_1$ | $Cl\diagdown_{X_2}$ | H | H | $X_3$—piperidine-N-C(O)CH$_3$ | MH+ = 506<br>RT = 2.87<br>Method A |
| 157 | $H_3C$—$X_1$ | $Cl\diagdown_{X_2}$ | H | H | $X_3$—piperidine-N-C(O)CH(CH$_3$)$_2$ | MH+ = 534<br>RT = 3.19<br>Method A |
| 158 | $H_3C$—$X_1$ | $Cl\diagdown_{X_2}$ | H | H | $X_3$—piperidine-N-C(O)CH$_2$CH(CH$_3$)$_2$ | MH+ = 548<br>RT = 3.29<br>Method A |

TABLE 6-continued

| Example | R¹ | R²ᵃ | R²ᵇ | R⁴ | R³ | HPLC-MS analysis |
|---|---|---|---|---|---|---|
| 159 | H₃C—X₁ | Cl—X₂ | H | H | X₃-(4-piperidinyl)-C(O)-cyclopentyl | MH+ = 560 RT = 3.45 Method A |
| 160 | H₃C—X₁ | Cl—X₂ | H | H | X₃-(4-piperidinyl)-C(O)-CH₂-cyclopentyl | MH+ = 574 RT = 3.45 Method A |

Example 161

N-{8-[2-chloro-5-(1-methanesulphonyl-piperidin-4-ylethynyl)-phenyl]-4,5-dihydro-thiazolo[4,5-h]quinazolin-2-yl}-acetamide

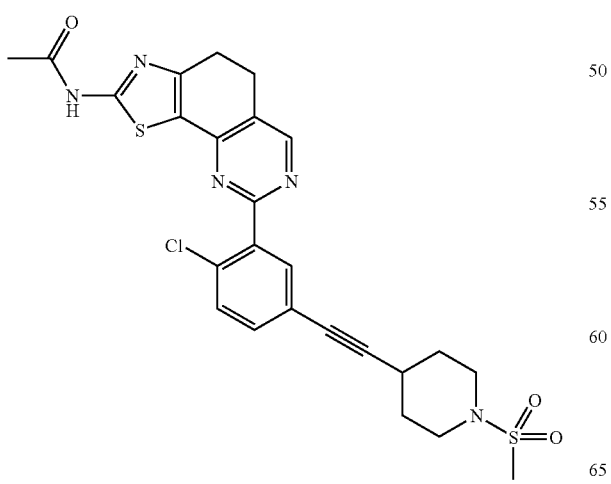

A mixture of 50 mg (0.11 mmol) N-[8-(2-chloro-5-piperidin-4-ylethynyl-phenyl)-4,5-dihydro-thiazolo[4,5-h]quinazolin-2-yl]-acetamide, 65 μL triethylamine and 15 μL methanesulphonic acid chloride in 1 mL dichloromethane is stirred for three hours at ambient temperature. The reaction mixture is washed with saturated aqueous sodium hydrogen carbonate solution and the organic phase is evaporated down. The residue remaining is purified by RP-HPLC. Yield: 23 mg yellow solid (MH+=542; RT=3.07; Method A)

The following Examples may be prepared analogously:
TABLE 7
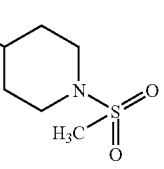
| Example | R¹ | R²ᵃ | R²ᵇ | R⁴ | R³ | HPLC-MS analysis |
|---|---|---|---|---|---|---|
| 161 | H₃C—X₁ | Cl—X₂ | H | H | X₃— 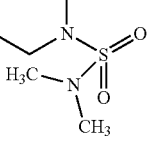 | MH+ = 542<br>RT = 3.07<br>Method A |
| 162 | H₃C—X₁ | Cl—X₂ | H | H | X₃— | MH+ = 571<br>RT = 3.23<br>Method A |
| 163 | H₃C—X₁ | Cl—X₂ | H | H | X₃— 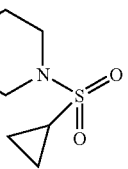 | MH+ = 568<br>RT = 3.21<br>Method A |
| 164 | H₃C—X₁ | Cl—X₂ | H | H | X₃— 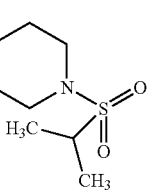 | MH+ = 570<br>RT = 3.23<br>Method A |

Example 165

4-[3-(2-acetylamino-4,5-dihydro-thiazolo[4,5-h]quinazolin-8-yl)-4-chloro-phenylethynyl]-piperidine-1-carboxylic acid isopropylamide

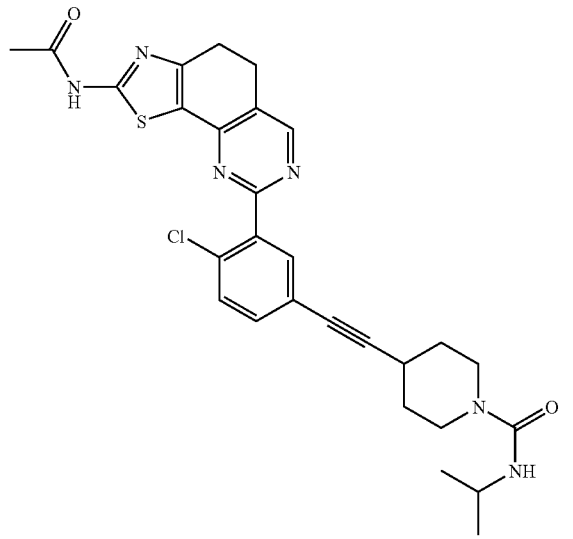

50 mg (0.11 mmol) N-[8-(2-chloro-5-piperidin-4-ylethynyl-phenyl)-4,5-dihydro-thiazolo[4,5-h]quinazolin-2-yl]-acetamide are suspended in 1 mL acetonitrile and combined successively with 17 μL triethylamine and 22 μM isopropyl isocyanate. The yellow suspension is stirred for three hours at ambient temperature and then washed with aqueous potassium carbonate solution. The organic phase is evaporated down and the residue is purified by RP-HPLC. Yield: 30 mg yellow solid.

The following Examples may be prepared analogously by using the corresponding isocyanates or carbamoyl chlorides:

TABLE 8

| Example | $R^1$ | $R^{2a}$ | $R^{2b}$ | $R^4$ | $R^3$ | HPLC-MS analysis |
|---|---|---|---|---|---|---|
| 165 | $H_3C-X_1$ | $Cl-X_2$ | H | H | (X₃-piperidine-N-C(O)-NH-CH(CH₃)-CH₃) | MH+ = 549<br>RT = 3.09<br>Method A |
| 166 | $H_3C-X_1$ | $Cl-X_2$ | H | H | (X₃-piperidine-N-C(O)-NH-CH₂-CH₃) | MH+ = 535<br>RT = 2.89<br>Method A |

TABLE 8-continued

| Example | R¹ | R²ᵃ | R²ᵇ | R⁴ | R³ | HPLC-MS analysis |
|---|---|---|---|---|---|---|
| 167 | H₃C—X₁ | Cl—X₂ | H | H | X₃–(piperidine-N-C(O)NH-CH₃) | MH+ = 521<br>RT = 2.84<br>Method A |
| 168 | H₃C—X₁ | Cl—X₂ | H | H | X₃–(piperidine-N-C(O)NH-C(CH₃)₃) | MH+ = 563<br>RT = 3.28<br>Method A |
| 169 | H₃C—X₁ | Cl—X₂ | H | H | X₃–(piperidine-N-C(O)N(CH₃)₂) | MH+ = 535<br>RT = 3.08<br>Method A |
| 170 | H₃C—X₁ | Cl—X₂ | H | H | X₃–(piperidine-N-C(O)NH-CH₂-cyclohexyl) | MH+ = 603<br>RT = 3.44<br>Method A |
| 171 | H₃C—X₁ | Cl—X₂ | H | H | X₃–(piperidine-N-C(O)NH-cyclopentyl) | MH+ = 575<br>RT = 3.19<br>Method A |

TABLE 8-continued

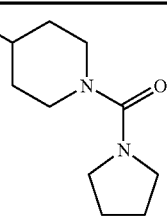

| Example | R¹ | R²ᵃ | R²ᵇ | R⁴ | R³ | HPLC-MS analysis |
|---|---|---|---|---|---|---|
| 172 | H₃C—X₁ | Cl—X₂ | H | H | X₃—[piperidine-N-C(O)-pyrrolidine] | MH+ = 561<br>RT = 3.18<br>Method A |
| 173 | H₃C—X₁ | Cl—X₂ | H | H | X₃—[piperidine-N-C(O)-morpholine] | MH+ = 577<br>RT = 2.99<br>Method A |

Example 174

N-{8-[2-chloro-5-(5-morpholin-4-yl-pent-1-ynyl)-phenyl]-4,5-dihydro-thiazolo[4,5-h]quinazolin-2-yl}-acetamide

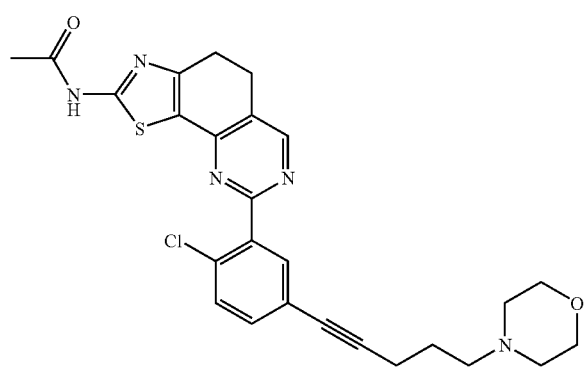

5.0 g (10.4 mmol) N-[8-(2-chloro-5-iodo-phenyl)-4,5-dihydro-thiazolo[4,5-h]quinazolin-2-yl]-acetamide are placed in 100 mL tetrahydrofuran under an argon atmosphere and combined with 3.5 g (41.4 mmol) 4-pentyn-1-ol and 6.7 ml (41.4 mmol) diisopropylethylamine. The mixture is kept free from oxygen and 727 mg (1.0 mmol) triphenylphosphine palladium(II)-chloride and 197 mg (1.0 mmol) copper(I)-iodide are added. The mixture is stirred for 2.5 hours at ambient temperature. After cooling to ambient temperature the reaction mixture is evaporated down and stirred with dichloromethane. The orange precipitate is suction filtered and dried. Yield: 5.2 g 5.2 g (10.3 mmol) of the intermediate described above, 3.9 mL (28.1 mmol) triethylamine and 40 mg 4-dimethylaminopyridine in 40 mL THF is combined at 0° C. with 1.8 mL (23.4 mmol) methanesulphonyl chloride and stirred overnight at ambient temperature. The reaction mixture is evaporated down and taken up in aqueous ammonia and dichloromethane. The organic phase is filtered through activated charcoal, dried and evaporated down. The residue is purified by MPLC (dichloromethane/methanol 100:5).

Yield: 2.2 g colourless oil.

80 mg (0.16 mmol) of the intermediate described above and 40 mg (0.46 mmol) morpholine in 1 mL DMF are stirred overnight at ambient temperature and the heated to 70° C. for six hours. The reaction mixture is purified by RP-HPLC without any further working up. Yield: 58 mg yellow solid (MH+=508; RT=2.46; Method A)

TABLE 9

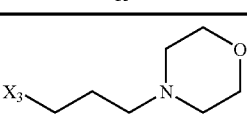

| Example | R¹ | R²ᵃ | R²ᵇ | R⁴ | R³ | HPLC-MS analysis |
|---|---|---|---|---|---|---|
| 174 | H₃C—X₁ | Cl—X₂ | H | H |  | MH+ = 508<br>RT = 2.46<br>Method A |
| 175 | H₃C—X₁ | Cl—X₂ | H | H | 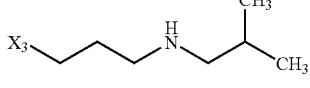 | MH+ = 506<br>RT = 2.62<br>Method A |
| 176 | H₃C—X₁ | Cl—X₂ | H | H | 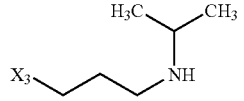 | MH+ = 494<br>RT = 2.61<br>Method A |
| 177 | H₃C—X₁ | Cl—X₂ | H | H | 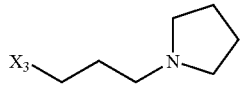 | MH+ = 480<br>RT = 2.51<br>Method A |
| 178 | H₃C—X₁ | Cl—X₂ | H | H | 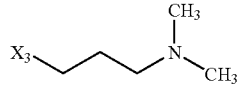 | MH+ = 492<br>RT = 2.52<br>Method A |
| 179 | H₃C—X₁ | Cl—X₂ | H | H | 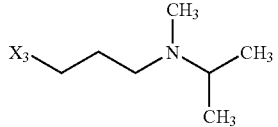 | MH+ = 466<br>RT = 2.45<br>Method A |
| 180 | H₃C—X₁ | Cl—X₂ | H | H | 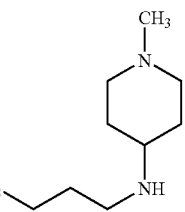 | MH+ = 494<br>RT = 2.53<br>Method A |
| 181 | H₃C—X₁ | Cl—X₂ | H | H | 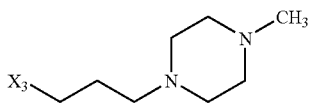 | MH+ = 535<br>RT = 2.29<br>Method A |
| 182 | H₃C—X₁ | Cl—X₂ | H | H | | MH+ = 521<br>RT = 2.29<br>Method A |

TABLE 9-continued

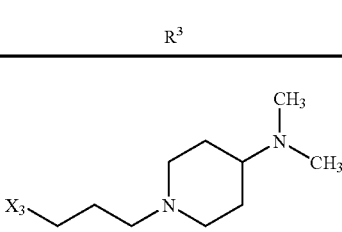

| Example | $R^1$ | $R^{2a}$ | $R^{2b}$ | $R^4$ | $R^3$ | HPLC-MS analysis |
|---|---|---|---|---|---|---|
| 183 | $H_3C-X_1$ | $Cl\diagdown_{X_2}$ | H | H | $X_3\diagdown\diagdown\diagdown N\diagdown\diagup\diagdown N(CH_3)_2$ (with CH₃ groups) | MH+ = 549 RT = 2.31 Method A |

Biological Test

The compounds of formula (I) mentioned by way of example are characterised by an affinity for PI3-kinase, i.e. in the test by an $IC_{50}$ value of below 600 nmol/litre.

In order to determine the inhibitory activity of the compounds on PI3Kγ, the in-vitro kinase assay described below was used. The expression and purification of $G\beta_1\gamma_2$-His and p101-GST/p110γ from Sf9-cells (*Spodoptera frugiperda* 9) has already been described (Maier et al., J. Biol. Chem. 1999 (274) 29311-29317).

10 μl of the compound to be tested were placed on 96 well PVDF filter plates (0.45 μM) and incubated for 20 min with 30 μl lipid vesicles ($PIP_2$ (0.7 μg/well), phosphatidylethanolamine (7.5 μg/well), phosphatidylserine (7.5 μg/well), sphingomyelin (0.7 μg/well) and phosphatidylcholine (3.2 μg/well)) which contained 1-3 ng PI3K☐ and 20-60 ng G☐₁☐₂-His. The reaction was started by the addition of 10 μl reaction buffer (40 mM Hepes, pH 7.5, 100 mM NaCl, 1 mM EGTA, 1 mM ☐-glycerophosphate, 1 mM DTT, 7 mM $MgCl_2$ and 0.1% BSA; 1 μM ATP and 0.2 μCi [☐-$^{33}$P]-ATP) and incubated for 120 min at ambient temperature. The reaction solution was sucked through the filters by the application of a vacuum and washed with 200 μl PBS. After the plates had been dried at 50° C. the radioactivity remaining in the plates was determined after the addition of 50 μl scintillation liquid using a Top-Count measuring device.

Ranges of Indications

It has been found that the compounds of formula (I) are characterised by a variety of possible applications in the therapeutic field. Particular mention should be made of those applications for which the compounds of formula (I) according to the invention are preferably used by virtue of their pharmaceutical activity as PI3-kinase modulators.

Generally speaking, these are diseases in whose pathology PI3-kinases are implicated, particularly inflammatory and allergic diseases. Particular mention should be made of inflammatory and allergic respiratory complaints, inflammatory diseases of the gastrointestinal tract, inflammatory diseases of the motor apparatus, inflammatory and allergic skin diseases, inflammatory eye diseases, diseases of the nasal mucosa, inflammatory or allergic ailments which involve autoimmune reactions or inflammation of the kidneys. The treatment may be symptomatic, adaptive, curative or preventative.

Respiratory complaints deserving special mention would be chronic and/or obstructive respiratory complaints. The compounds of formula 1 according to the invention may, by virtue of their pharmacological properties, bring about a reduction in Tissue damage
Inflammation of the airways
bronchial hyperreactivity
the process of reconstruction of the lung as a result of inflammation
worsening of the disease (progression).

The compounds according to the invention are particularly preferred for preparing a medicament for the treatment of chronic bronchitis, acute bronchitis, bronchitis caused by bacterial or viral infection or fungi or helminths, allergic bronchitis, toxic bronchitis, chronic obstructive bronchitis (COPD), asthma (intrinsic or allergic), paediatric asthma, bronchiectasis, allergic alveolitis, allergic or non-allergic rhinitis, chronic sinusitis, cystic fibrosis or mucoviscidosis, alpha-1-antitrypsin deficiency, cough, pulmonary emphysema, interstitial lung diseases such as e.g. pulmonary fibrosis, asbestosis and silicosis and alveolitis; hyperreactive airways, nasal polyps, pulmonary oedema such as e.g. toxic pulmonary oedema and ARDS/IRDS, pneumonitis of different origins, e.g. radiation-induced or caused by aspiration or infectious pneumonitis, collagenoses such as lupus erythematodes, systemic sclerodermy, sarcoidosis or Boeck's disease.

The compounds of formula (I) are also suitable for the treatment of diseases of the skin, such as e.g. psoriasis, contact dermatitis, atopic dermatitis, alopecia areata (circular hair loss), erythema exsudativum multiforme (Stevens-Johnson Syndrome), dermatitis herpetiformis, sclerodermy, vitiligo, nettle rash (urticaria), lupus erythematodes, follicular and surface pyodermy, endogenous and exogenous acne, acne rosacea and other inflammatory or allergic or proliferative skin diseases.

Moreover, the compounds of formula (I) are suitable for therapeutic use in cases of inflammatory or allergic complaints which involve autoimmune reactions, such as e.g. inflammatory bowel diseases, e.g. Crohn's disease or ulcerative colitis; diseases of the arthritis type, such as e.g. rheumatoid or psoriatic arthritis, osteoarthritis, rheumatoid spondylitis and other arthritic conditions or multiple sclerosis.

The following general inflammatory or allergic diseases may also be mentioned, which can be treated with medicaments containing compounds of formula (I):

- inflammation of the eye, such as e.g. conjunctivitis of various kinds, e.g. caused by infections with fungi or bacteria, allergic conjunctivitis, irritable conjunctivitis, drug-induced conjunctivitis, keratitis, uveitis
- diseases of the nasal mucosa, such as e.g. allergic rhinitis/sinusitis or nasal polyps
- inflammatory or allergic conditions, such as e.g. systemic lupus erythematodes, chronic hepatitis, kidney inflammations such as glomerulonephritis, interstitial nephritis or idiopathic nephrotic syndrome.

Other diseases which may be treated with a drug containing compounds of formula (I) on the basis of their pharmacological activity include toxic or septic shock syndrome, atherosclerosis, middle ear infections (otitis media), hypertrophy of the heart, cardiac insufficiency, stroke, ischaemic reperfusion injury or neurodegenerative diseases such as Parkinson's disease or Alzheimer's.

Combinations

The compounds of formula (I) may be used on their own or in combination with other active substances of formula (I). If desired the compounds of formula (I) may also be used in combination with W, where W denotes a pharmacologically active substance and (for example) is selected from among the betamimetics, anticholinergics, corticosteroids, PDE4-inhibitors, LTD4-antagonists, EGFR-inhibitors, dopamine agonists, H1-antihistamines, PAF-antagonists and PI3-kinase inhibitors, preferably PI3-☐Kinase inhibitors. Moreover, double or triple combinations of W may be combined with the compounds of formula (I). Combinations of W might be, for example:

- W denotes a betamimetic, combined with an active substance selected from among the anticholinergics, corticosteroids, PDE4-inhibitors, EGFR-inhibitors and LTD4-antagonists,
- W denotes an anticholinergic, combined with an active substance selected from among the betamimetics, corticosteroids, PDE4-inhibitors EGFR-inhibitors and LTD4-antagonists,
- W denotes a corticosteroid, combined with an active substance selected from among the PDE4-inhibitors, EGFR-inhibitors and LTD4-antagonists
- W denotes a PDE4-inhibitor, combined with an active substance selected from among the EGFR-inhibitors and LTD4-antagonists
- W denotes an EGFR-inhibitor, combined with an LTD4-antagonist.

The compounds used as betamimetics are preferably compounds selected from among albuterol, arformoterol, bambuterol, bitolterol, broxaterol, carbuterol, clenbuterol, fenoterol, formoterol, hexoprenaline, ibuterol, isoetharine, isoprenaline, levosalbutamol, mabuterol, meluadrine, metaproterenol, orciprenaline, pirbuterol, procaterol, reproterol, rimiterol, ritodrine, salmefamol, salmeterol, soterenol, sulphonterol, terbutaline, tiaramide, tolubuterol, zinterol, CHF-1035, HOKU-81, KUL-1248 and 3-(4-{6-[2-hydroxy-2-(4-hydroxy-3-hydroxymethyl-phenyl)-ethylamino]-hexyloxy}-butyl)-benzyl-sulphonamide
5-[2-(5.6-diethyl-indan-2-ylamino)-1-hydroxy-ethyl]-8-hydroxy-1H-quinoline-2-one
4-hydroxy-7-[2-{[2-{[3-(2-phenylethoxy)propyl] sulphonyl}ethyl]-amino}ethyl]-2(3H)-benzothiazolone
1-(2-fluoro-4-hydroxyphenyl)-2-[4-(1-benzimidazolyl)-2-methyl-2-butylamino]ethanol
1-[3-(4-methoxybenzyl-amino)-4-hydroxyphenyl]-2-[4-(1-benzimidazolyl)-2-methyl-2-butylamino]ethanol
1-[2H-5-hydroxy-3-oxo-4H-1,4-benzoxazin-8-yl]-2-[3-(4-N,N-dimethylaminophenyl)-2-methyl-2-propylamino] ethanol
1-[2H-5-hydroxy-3-oxo-4H-1,4-benzoxazin-8-yl]-2-[3-(4-methoxyphenyl)-2-methyl-2-propylamino]ethanol
1-[2H-5-hydroxy-3-oxo-4H-1,4-benzoxazin-8-yl]-2-[3-(4-n-butyloxyphenyl)-2-methyl-2-propylamino]ethanol
1-[2H-5-hydroxy-3-oxo-4H-1,4-benzoxazin-8-yl]-2-{4-[3-(4-methoxyphenyl)-1,2,4-triazole-3-yl]-2-methyl-2-butylamino}ethanol
5-hydroxy-8-(1-hydroxy-2-isopropylaminobutyl)-2H-1,4-benzoxazin-3-(4H)-on
1-(4-amino-3-chloro-5-trifluoromethylphenyl)-2-tert.-butylamino)ethanol
6-hydroxy-8-{1-hydroxy-2-[2-(4-methoxy-phenyl)-1,1-dimethyl-ethylamino]-ethyl}-4H-benzo[1,4]oxazin-3-one
6-hydroxy-8-{1-hydroxy-2-[2-(ethyl 4-phenoxy-acetate)-1,1-dimethyl-ethylamino]-ethyl}-4H-benzo[1,4]oxazin-3-one
6-hydroxy-8-{1-hydroxy-2-[2-(4-phenoxy-acetic acid)-1,1-dimethyl-ethylamino]-ethyl}-4H-benzo[1,4]oxazin-3-one
8-{2-[1,1-dimethyl-2-(2.4.6-trimethylphenyl)-ethylamino]-1-hydroxy-ethyl}-6-hydroxy-4H-benzo[1,4]oxazin-3-one
6-hydroxy-8-{1-hydroxy-2-[2-(4-hydroxy-phenyl)-1,1-dimethyl-ethylamino]-ethyl}-4H-benzo[1,4]oxazin-3-one
6-hydroxy-8-{1-hydroxy-2-[2-(4-isopropyl-phenyl)-1.1dimethyl-ethylamino]-ethyl}-4H-benzo[1,4]oxazin-3-one
8-{2-[2-(4-ethyl-phenyl)-1,1-dimethyl-ethylamino]-1-hydroxy-ethyl}-6-hydroxy-4H-benzo[1,4]oxazin-3-one
8-{2-[2-(4-ethoxy-phenyl)-1,1-dimethyl-ethylamino]-1-hydroxy-ethyl}-6-hydroxy-4H-benzo[1,4]oxazin-3-one
4-(4-{2-[2-hydroxy-2-(6-hydroxy-3-oxo-3,4-dihydro-2H-benzo[1,4]oxazin-8-yl)-ethylamino]-2-methyl-propyl}-phenoxy)-butyric acid
8-{2-[2-(3,4-difluoro-phenyl)-1,1-dimethyl-ethylamino]-1-hydroxy-ethyl}-6-hydroxy-4H-benzo[1,4]oxazin-3-one
1-(4-ethoxy-carbonylamino-3-cyano-5-fluorophenyl)-2-(tert-butylamino)ethanol optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The anticholinergics used are preferably compounds selected from among the tiotropium salts, preferably the bromide salt, oxitropium salts, preferably the bromide salt, flutropium salts, preferably the bromide salt, ipratropium salts, preferably the bromide salt, glycopyrronium salts, preferably the bromide salt, trospium salts, preferably the chloride salt, tolterodine. In the above-mentioned salts the cations are the pharmacologically active constituents. As anions the above-mentioned salts may preferably contain the chloride, bromide, iodide, sulphate, phosphate, methanesulphonate, nitrate, maleate, acetate, citrate, fumarate, tartrate, oxalate, succinate, benzoate or p-toluenesulphonate, while chloride, bromide, iodide, sulphate, methanesulphonate or p-toluenesulphonate are preferred as counter-ions.

Of all the salts the chlorides, bromides, iodides and methanesulphonates are particularly preferred.

Other specified compounds are:
tropenol 2,2-diphenylpropionate methobromide
scopine 2,2-diphenylpropionate methobromide
scopine 2-fluoro-2,2-diphenylacetate methobromide
tropenol 2-fluoro-2,2-diphenylacetate methobromide
tropenol 3,3',4,4'-tetrafluorobenzilate methobromide
scopine 3,3',4,4'-tetrafluorobenzilate methobromide
tropenol 4,4'-difluorobenzilate methobromide
scopine 4,4'-difluorobenzilate methobromide
tropenol 3,3'-difluorobenzilate methobromide
scopine 3,3'-difluorobenzilate methobromide
tropenol 9-hydroxy-fluorene-9-carboxylate methobromide
tropenol 9-fluoro-fluorene-9-carboxylate methobromide
scopine 9-hydroxy-fluorene-9-carboxylate methobromide
scopine 9-fluoro-fluorene-9-carboxylate methobromide
tropenol 9-methyl-fluorene-9-carboxylate methobromide
scopine 9-methyl-fluorene-9-carboxylate methobromide
cyclopropyltropine benzilate methobromide
cyclopropyltropine 2,2-diphenylpropionate methobromide
cyclopropyltropine 9-hydroxy-xanthene-9-carboxylate methobromide
cyclopropyltropine 9-methyl-fluorene-9-carboxylate methobromide
cyclopropyltropine 9-methyl-xanthene-9-carboxylate methobromide
cyclopropyltropine 9-hydroxy-fluorene-9-carboxylate methobromide
cyclopropyltropine methyl 4,4'-difluorobenzilate methobromide
tropenol 9-hydroxy-xanthene-9-carboxylate methobromide
scopine 9-hydroxy-xanthene-9-carboxylate methobromide
tropenol 9-methyl-xanthene-9-carboxylate-methobromide
scopine 9-methyl-xanthene-9-carboxylate-methobromide
tropenol 9-ethyl-xanthene-9-carboxylate methobromide
tropenol 9-difluoromethyl-xanthene-9-carboxylate methobromide
scopine 9-hydroxymethyl-xanthene-9-carboxylate methobromide As corticosteroids it is preferable to use compounds selected from among prednisolone, prednisone, butixocort propionate, flunisolide, beclomethasone, triamcinolone, budesonide, fluticasone, mometasone, ciclesonide, rofleponide, dexamethasone, betamethasone, deflazacort, RPR-106541, NS-126, ST-26 and (S)-fluoromethyl 6,9-difluoro-17-[(2-furanylcarbonyl)oxy]-11-hydroxy-16-methyl-3-oxo-androsta-1,4-diene-17-carbothionate
(S)-(2-oxo-tetrahydro-furan-3S-yl)6,9-difluoro-11-hydroxy-16-methyl-3-oxo-17-propionyloxy-androsta-1,4-diene-17-carbothionate,
etiprednol-dichloroacetate optionally in the form of the racemates, enantiomers or diastereomers thereof and optionally in the form of the salts and derivatives thereof, the solvates and/or hydrates thereof. Any reference to steroids includes a reference to any salts or derivatives, hydrates or solvates thereof which may exist. Examples of possible salts and derivatives of the steroids may be: alkali metal salts, such as for example sodium or potassium salts, sulphobenzoates, phosphates, isonicotinates, acetates, propionates, dihydrogen phosphates, palmitates, pivalates or furoates.

PDE4-inhibitors which may be used are preferably compounds selected from among enprofyllin, theophyllin, roflumilast, ariflo (cilomilast), tofimilast, pumafentrin, lirimilast, arofyllin, atizoram, D-4418, Bay-198004, BY343, CP-325.366, D-4396 (Sch-351591), AWD-12-281 (GW-842470), NCS-613, CDP-840, D-4418, PD-168787, T-440, T-2585, V-1 1294A, CI-1018, CDC-801, CDC-3052, D-22888, YM-58997, Z-15370 and
N-(3,5-dichloro-1-oxo-pyridin-4-yl)-4-difluoromethoxy-3-cyclopropylmethoxybenzamide
(−)p-[(4aR*,10bS*)-9-ethoxy-1,2,3,4,4a,10b-hexahydro-8-methoxy-2-methylbenzo[s][1,6]naphthyridin-6-yl]-N,N-diisopropylbenzamide
(R)-(+)-1-(4-bromobenzyl)-4-[(3-cyclopentyloxy)-4-methoxyphenyl]-2-pyrrolidone
3-(cyclopentyloxy-4-methoxyphenyl)-1-(4-N'-[N-2-cyano-S-methyl-isothioureido]benzyl)-2-pyrrolidone
cis[4-cyano-4-(3-cyclopentyloxy-4-methoxyphenyl)cyclohexane-1-carboxylic acid]
2-carbomethoxy-4-cyano-4-(3-cyclopropylmethoxy-4-difluoromethoxy-phenyl)cyclohexan-1-one
cis[4-cyano-4-(3-cyclopropylmethoxy-4-difluoromethoxyphenyl)cyclohexan-1-ol]
(R)-(+)-ethyl[4-(3-cyclopentyloxy-4-methoxyphenyl)pyrrolidin-2-ylidene]acetate
(S)-(−)-ethyl[4-(3-cyclopentyloxy-4-methoxyphenyl)pyrrolidin-2-ylidene]acetate
9-cyclopentyl-5,6-dihydro-7-ethyl-3-(2-thienyl)-9H-pyrazolo[3,4-c]-1,2,4-triazolo[4.3-a]pyridine
9-cyclopentyl-5,6-dihydro-7-ethyl-3-(tert-butyl)-9H-pyrazolo [3,4-c]-1,2,4-triazolo[4.3-a]pyridine optionally in the form of the racemates, enantiomers or diastereomers thereof and optionally in the form of the pharmacologically acceptable acid addition salts thereof, the solvates and/or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The LTD4-antagonists used are preferably compounds selected from among montelukast, pranlukast, zafirlukast, MCC-847 (ZD-3523), MN-001, MEN-91507 (LM-1507), VUF-5078, VUF-K-8707, L-733321 and
1-(((R)-(3-(2-(6,7-difluoro-2-quinolinyl)ethenyl)phenyl)-3-(2-(2-hydroxy-2-propyl)phenyl)thio)methylcyclopropane-acetic acid, 1-(((1(R)-3(3-(2-(2,3-dichlorothieno[3,2-b]pyridin-5-yl)-(E)-ethenyl)phenyl)-3-(2-(1-hydroxy-1-methylethyl)phenyl)propyl)thio)methyl)cyclopropaneacetic acid

[2-[[2-(4-tert-butyl-2-thiazolyl)-5-benzofuranyl]oxymethyl]phenyl]acetic acid optionally in the form of the racemates, enantiomers or diastereomers thereof and optionally in the form of the pharmacologically acceptable acid addition salts, solvates and/or hydrates thereof. According to the invention the acid addition salts of the betamimetics are preferably selected from among the hydrochloride, hydrobromide, hydroiodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate. By salts or derivatives which the LTD4-antagonists may optionally be capable of forming are meant, for example: alkali metal salts, such as for example sodium or potassium salts, alkaline earth metal salts, sulphobenzoates, phosphates, isonicotinates, acetates, propionates, dihydrogen phosphates, palmitates, pivalates or furoates.

EGFR-inhibitors which may be used are preferably compounds selected from among cetuximab, trastuzumab, ABX-EGF, Mab ICR-62 and 4-[(3-chloro-4-fluorophenyl)amino]-6-{[4-(morpholin-4-yl)-1-oxo-2-buten-1-yl]-amino}-7-cyclopropylmethoxy-quinazoline 4-[(3-chloro-4-fluorophenyl)amino]-6-{[4-(N,N-diethylamino)-1-oxo-2-buten-1-yl]amino}-7-cyclopropyl-methoxy-quinazoline 4-[(3-chloro-4-fluorophenyl)amino]-6-{[4-(N,N-dimethylamino)-1-oxo-2-buten-1-yl]amino}-7-cyclopropyl-methoxy-quinazoline 4-[(R)-(1-phenyl-ethyl)amino]-6-{[4-(morpholin-4-yl)-1-oxo-2-buten-1-yl]amino}-7-cyclopentyloxy-quinazoline 4-[(3-chloro-4-fluoro-phenyl)amino]-6-{[4-((R)-6-methyl-2-oxo-morpholin-4-yl)-1-oxo-2-buten-1-yl]amino}-7-cyclopropylmethoxy-quinazoline 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline 4-[(3-chloro-4-fluoro-phenyl)amino]-6-{[4-((R)-2-methoxymethyl-6-oxo-morpholin-4-yl)-1-oxo-2-buten-1-yl]amino}-7-cyclopropylmethoxy-quinazoline 4-[(3-chloro-4-fluoro-phenyl)amino]-6-[2-((S)-6-methyl-2-oxo-morpholin-4-yl)-ethoxy]-7-methoxy-quinazoline 4-[(3-chloro-4-fluorophenyl)amino]-6-({4-[N-(2-methoxy-ethyl)-N-methyl-amino]-1-oxo-2-buten-1-yl}amino)-7-cyclopropylmethoxy-quinazoline 4-[(3-chloro-4-fluorophenyl)amino]-6-{[4-(N,N-dimethylamino)-1-oxo-2-buten-1-yl]amino}-7-cyclopentyloxy-quinazoline 4-[(R)-(1-phenyl-ethyl)amino]-6-{[4-(N,N-bis-(2-methoxy-ethyl)-amino)-1-oxo-2-buten-1-yl]amino}-7-cyclopropylmethoxy-quinazoline 4-[(R)-(1-phenyl-ethyl)amino]-6-({4-[N-(2-methoxy-ethyl)-N-ethyl-amino]-1-oxo-2-buten-1-yl}amino)-7-cyclopropylmethoxy-quinazoline 4-[(R)-(1-phenyl-ethyl)amino]-6-({4-[N-(2-methoxy-ethyl)-N-methyl-amino]-1-oxo-2-buten-1-yl}amino)-7-cyclopropylmethoxy-quinazoline 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline 4-[(3-chloro-4-fluorophenyl)amino]-6-{[4-(N,N-dimethylamino)-1-oxo-2-buten-1-yl]amino}-7-((R)-tetrahydrofuran-3-yloxy)-quinazoline 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline 4-[(3-chloro-4-fluorophenyl)amino]-6-({4-[N-(2-methoxy-ethyl)-N-methyl-amino]-1-oxo-2-buten-1-yl}amino)-7-cyclopentyloxy-quinazoline 4-[(3-chloro-4-fluorophenyl)amino]-6-{[4-(N-cyclopropyl-N-methyl-amino)-1-oxo-2-buten-1-yl]amino}-7-cyclopentyloxy-quinazoline 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline 4-[(3-chloro-4-fluorophenyl)amino]-6-{[4-(N,N-dimethylamino)-1-oxo-2-buten-1-yl]amino}-7-[(S)-(tetrahydrofuran-2-yl)methoxy]-quinazoline 4-[(3-ethynyl-phenyl)amino]-6.7-bis-(2-methoxy-ethoxy)-quinazoline 4-[(3-chloro-4-fluorophenyl)amino]-7-[3-(morpholin-4-yl)-propyloxy]-6-[(vinyl-carbonyl)amino]-quinazoline 4-[(R)-(1-phenyl-ethyl)amino]-6-(4-hydroxy-phenyl)-7H-pyrrolo[2,3-d]pyrimidine 3-cyano-4-[(3-chloro-4-fluorophenyl)amino]-6-{[4-(N,N-dimethylamino)- -oxo-2-buten-1-yl]amino}-7-ethoxy-quinoline 4-{[3-chloro-4-(3-fluoro-benzyloxy)-phenyl]amino}-6-(5-[(2-methanesulphonyl-ethyl)amino]methyl}-furan-2-yl) quinazoline 4-[(R)-(1-phenyl-ethyl)amino]-6-{[4-((R)-6-methyl-2-oxo-morpholin-4-yl)-1-oxo-2-buten-1-yl]amino}-7-methoxy-quinazoline 4-[(3-chloro-4-fluorophenyl)amino]-6-{[4-(morpholin-4-yl)-1-oxo-2-buten-1-yl]-amino}-7-[(tetrahydrofuran-2-yl)methoxy]-quinazoline 4-[(3-chloro-4-fluorophenyl)amino]-6-({4-[N,N-bis-(2-methoxy-ethyl)-amino]-1-oxo-2-buten-1-yl}amino)-7-[(tetrahydrofuran-2-yl)methoxy]-quinazoline 4-[(3-ethynyl-phenyl)amino]-6-{[4-(5.5-dimethyl-2-oxo-morpholin-4-yl)-1-oxo-2-buten-1-yl]amino}-quinazoline 4-[(3-chloro-4-fluoro-phenyl)amino]-6-[2-(2.2-dimethyl-6-oxo-morpholin-4-yl)-ethoxy]-7-methoxy-quinazoline 4-[(3-chloro-4-fluoro-phenyl)amino]-6-[2-(2.2-dimethyl-6-oxo-morpholin-4-yl)-ethoxy]-7-[(R)-(tetrahydrofuran-2-yl)methoxy]-quinazoline 4-[(3-chloro-4-fluoro-phenyl)amino]-7-[2-(2.2-dimethyl-6-oxo-morpholin-4-yl)-ethoxy]-6-[(S)-(tetrahydrofuran-2-yl)methoxy]-quinazoline 4-[(3-chloro-4-fluoro-phenyl)amino]-6-{2-[4-(2-oxo-morpholin-4-yl)-piperidin-1-yl]-ethoxy}-7-methoxy-quinazoline 4-[(3-chloro-4-fluoro-phenyl)amino]-6-[1-(tert.-butyloxycarbonyl)-piperidin-4-yloxy]-7-methoxy-quinazoline 4-[(3-chloro-4-fluoro-phenyl)amino]-6-(trans-4-amino-cyclohexan-1-yloxy)-7-methoxy-quinazoline 4-[(3-chloro-4-fluoro-phenyl)amino]-6-(trans-4-methanesulphonylamino-cyclohexan-1-yloxy)-7-methoxy-quinazoline 4-[(3-chloro-4-fluoro-phenyl)amino]-6-(tetrahydropyran-3-yloxy)-7-methoxy-quinazoline 4-[(3-chloro-4-fluoro-phenyl)amino]-6-(1-methyl-piperidin-4-yloxy)-7-methoxy-quinazoline 4-[(3-chloro-4-fluoro-phenyl)amino]-6-{1-[(morpholin-4-yl)carbonyl]-piperidin-4-yloxy}-7-methoxy-quinazoline 4-[(3-chloro-4-fluoro-phenyl)amino]-6-{1-[(methoxymethyl)carbonyl]-piperidin-4-yloxy}-7-methoxy-quinazoline 4-[(3-chloro-4-fluoro-phenyl)amino]-6-(piperidin-3-yloxy)-7-methoxy-quinazoline 4-[(3-chloro-4-fluoro-phenyl)amino]-6-[1-(2-acetylamino-ethyl)-piperidin-4-yloxy]-7-methoxy-quinazoline 4-[(3-chloro-4-fluoro-phenyl)amino]-6-(tetrahydropyran-4-yloxy)-7-ethoxy-quinazoline 4-[(3-chloro-4-fluoro-phenyl)amino]-6-((S)-tetrahydrofuran-3-yloxy)-7-hydroxy-quinazoline 4-[(3-chloro-4-fluoro-phenyl)amino]-6-(tetrahydropyran-4-yloxy)-7-(2-methoxy-ethoxy)-quinazoline 4-[(3-chloro-4-fluoro-phenyl)amino]-6-{trans-4-[(dimethylamino)sulphonylamino]-cyclohexan-1-yloxy}-7-methoxy-quinazoline 4-[(3-chloro-4-fluoro-phenyl)amino]-6-{trans-4-[(morpholin-4-yl)carbonylamino]-cyclohexan-1-yloxy}-7-methoxy-quinazoline 4-[(3-chloro-4-fluoro-phenyl)amino]-6-{trans-4-[(morpholin-4-yl)sulphonylamino]-cyclohexan-1-yloxy}-7-methoxy-quinazoline 4-[(3-chloro-4-fluoro-phenyl)amino]-6-(tetrahydropyran-4-yloxy)-7-(2-acetylamino-ethoxy)-quinazoline 4-[(3-chloro-4-fluoro-phenyl)amino]-6-(tetrahydropyran-4-yloxy)-7-(2-methanesulphonylamino-ethoxy)-quinazoline 4-[(3-chloro-4-fluoro-phenyl)amino]-6-{1-[(piperidin-1-yl)carbonyl]-piperidin-4-yloxy}-7-methoxy-quinazoline 4-[(3-chloro-4-fluoro-phenyl)amino]-6-(1-aminocarbonylmethyl-piperidin-4-yloxy)-7-methoxy-quinazoline 4-[(3-chloro-4-fluoro-phenyl)amino]-6-(cis-4-{N-[(tetrahydropyran-4-yl)carbonyl]-N-methyl-amino}-cyclohexan-1-yloxy)-7-methoxy-quinazoline 4-[(3-chloro-4-fluoro-phenyl)amino]-6-(cis-4-{N-[(morpholin-4-yl)carbonyl]-N-methyl-amino}-cyclohexan-1-yloxy)-7-methoxy-quinazoline 4-[(3-chloro-4-fluoro-phenyl)amino]-6-(cis-4-{N-[(morpholin-4-yl)sulphonyl]-N-methyl-amino}-cyclohexan-1-yloxy)-7-methoxy-quinazoline 4-[(3-chloro-4-fluoro-phenyl)amino]-6-(trans-4-ethansulphonylamino-cyclohexan-1-yloxy)-7-methoxy-quinazoline 4-[(3-chloro-4-fluoro-phenyl)amino]-6-(1-methanesulphonyl-piperidin-4-yloxy)-7-ethoxy-quinazoline 4-[(3-chloro-4-fluoro-phenyl)amino]-6-(1-methanesulphonyl-piperidin-4-yloxy)-7-(2-methoxy-ethoxy)-quinazoline 4-[(3-chloro-4-fluoro-phenyl)amino]-6-[1-(2-methoxy-acetyl)-piperidin-4-yloxy]-7-(2-methoxy-ethoxy)-quinazoline 4-[(3-chloro-4-fluoro-phenyl)amino]-6-(cis-4-acetylamino-cyclohexan-1-yloxy)-7-methoxy-quinazoline 4-[(3-ethynyl-phenyl)amino]-6-[1-(tert.-butyloxycarbonyl)-piperidin-4-yloxy]-7-methoxy-quinazoline 4-[(3-ethynyl-phenyl)amino]-6-(tetrahydropyran-4-yloxy)-7-methoxy-quinazoline 4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline 4-[(3-chloro-4-fluoro-phenyl)amino]-6-(cis-4-{N-[(4-methyl-piperazin-1-yl)carbonyl]-N-methyl-amino}-cyclohexan-1-yloxy)-7-methoxy-quinazoline 4-[(3-chloro-4-fluoro-phenyl)amino]-6-{cis-4-[(morpholin-4-yl)carbonylamino]-cyclohexan-1-yloxy}-7-methoxy-quinazoline 4-[(3-chloro-4-fluoro-phenyl)amino]-6-{1-[2-(2-oxopyrrolidin-1-yl)ethyl]-piperidin-4-yloxy}-7-methoxy-quinazoline 4-[(3-chloro-4-fluoro-phenyl)amino]-6-{1-[(morpholin-4-yl)carbonyl]-piperidin-4-yloxy}-7-(2-methoxy-ethoxy)-quinazoline 4-[(3-ethynyl-phenyl)amino]-6-(1-acetyl-piperidin-4-yloxy)-7-methoxy-quinazoline 4-[(3-ethynyl-phenyl)amino]-6-(1-methyl-piperidin-4-yloxy)-7-methoxy-quinazoline 4-[(3-ethynyl-phenyl)amino]-6-(1-methanesulphonyl-piperidin-4-yloxy)-7-methoxy-quinazoline 4-[(3-chloro-4-fluoro-phenyl)amino]-6-(1-methyl-piperidin-4-yloxy)-7(2-methoxy-ethoxy)-quinazoline 4-[(3-chloro-4-fluoro-phenyl)amino]-6-(1-isopropyloxycarbonyl-piperidin-4-yloxy)-7-methoxy-quinazoline 4-[(3-chloro-4-fluoro-phenyl)amino]-6-(cis-4-methylamino-cyclohexan-1-yloxy)-7-methoxy-quinazoline 4-[(3-chloro-4-fluoro-phenyl)amino]-6-{cis-4-[N-(2-methoxy-acetyl)-N-methyl-amino]-cyclohexan-1-yloxy}-7-methoxy-quinazoline 4-[(3-ethynyl-phenyl)amino]-6-(piperidin-4-yloxy)-7-methoxy-quinazoline 4-[(3-ethynyl-phenyl)amino]-6-[1-(2-methoxy-acetyl)-piperidin-4-yloxy]-7-methoxy-quinazoline 4-[(3-ethynyl-phenyl)amino]-6-{1-[(morpholin-4-yl)carbonyl]-piperidin-4-yloxy}-7-methoxy-quinazoline 4-[(3-chloro-4-fluoro-phenyl)amino]-6-{1-[(cis-2,6-dimethyl-morpholin-4-yl)carbonyl]-piperidin-4-yloxy}-7-methoxy-quinazoline 4-[(3-chloro-4-fluoro-phenyl)amino]-6-{1-[(2-methyl-morpholin-4-yl)carbonyl]-piperidin-4-yloxy}-7-methoxy-quinazoline 4-[(3-chloro-4-fluoro-phenyl)amino]-6-{1-[(S,S)-(2-oxa-5-aza-bicyclo[2,2,1]hept-5-yl)carbonyl]-piperidin-4-yloxy}-7-methoxy-quinazoline 4-[(3-chloro-4-fluoro-phenyl)amino]-6-{1-[(N-methyl-N-2-methoxyethyl-amino)carbonyl]-piperidin-4-yloxy}-7-methoxy-quinazoline 4-[(3-chloro-4-fluoro-phenyl)amino]-6-(1-ethyl-piperidin-4-yloxy)-7-methoxy-quinazoline 4-[(3-chloro-4-fluoro-phenyl)amino]-6-{1-[(2-methoxyethyl)carbonyl]-piperidin-4-yloxy}-7-methoxy-quinazoline 4-[(3-chloro-4-fluoro-phenyl)amino]-6-{1-[(3-methoxypropyl-amino)-carbonyl]-piperidin-4-yloxy}-7-methoxy-quinazoline 4-[(3-chloro-4-fluoro-phenyl)amino]-6-[cis-4-(N-methanesulphonyl-N-methyl-amino)-cyclohexan-1-yloxy]-7-methoxy-quinazoline 4-[(3-chloro-4-fluoro-phenyl)amino]-6-[cis-4-(N-acetyl-N-methyl-amino)-cyclohexan-1-yloxy]-7-methoxy-quinazoline 4-[(3-chloro-4-fluoro-phenyl)amino]-6-(trans-4-methylamino-cyclohexan-1-yloxy)-7-methoxy-quinazoline 4-[(3-chloro-4-fluoro-phenyl)amino]-6-[trans-4-(N-methanesulphonyl-N-methyl-amino)-cyclohexan-1-yloxy]-7-methoxy-quinazoline 4-[(3-chloro-4-fluoro-phenyl)amino]-6-(trans-4-dimethylamino-cyclohexan-1-yloxy)-7-methoxy-quinazoline 4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline 4-[(3-chloro-4-fluoro-phenyl)amino]-6-[2-(2.2-dimethyl-6-oxo-morpholin-4-yl)-ethoxy]-7-[(S)-(tetrahydrofuran-2-yl)methoxy]-quinazoline 4-[(3-chloro-4-fluoro-phenyl)amino]-6-(1-methanesulphonyl-piperidin-4-yloxy)-7-methoxy-quinazoline 4-[(3-chloro-4-fluoro-phenyl)amino]-6-(1-cyano-piperidin-4-yloxy)-7-methoxy-quinazoline optionally in the form of the racemates, enantiomers, diastereomers thereof and optionally in the form of the pharmacologically acceptable acid addition salts, solvates or hydrates thereof. According to the invention the preferred acid addition salts of the betamimetics are selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The dopamine agonists used are preferably compounds selected from among bromocriptin, cabergoline, alpha-dihydroergocryptine, lisuride, pergolide, pramipexol, roxindol, ropinirol, talipexol, tergurid and viozan, optionally in the form of the racemates, enantiomers, diastereomers thereof and optionally in the form of the pharmacologically acceptable acid addition salts, solvates or hydrates thereof. According to the invention the preferred acid addition salts of the betamimetics are selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydrooxalate, hydrosuccinate, hydrobenzoate and hydro-p-toluenesulphonate.

H1-Antihistamines which may be used are preferably compounds selected from among epinastine, cetirizine, azelastine, fexofenadine, levocabastine, loratadine, mizolastine, ketotifen, emedastine, dimetindene, clemastine, bamipine, cexchlorpheniramine, pheniramine, doxylamine, chlorphenoxamine, dimenhydrinate, diphenhydramine, promethazine, ebastine, desloratidine and meclozine, optionally in the form of the racemates, enantiomers, diastereomers thereof and optionally in the form of the pharmacologically acceptable acid addition salts, solvates or hydrates thereof. According to the invention the preferred acid addition salts of the betamimetics are selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The PAF-antagonists used are preferably compounds selected from among 4-(2-chlorophenyl)-9-methyl-2-[3(4-morpholinyl)-3-propanon-1-yl]-6H-thieno-[3,2-f]-[1,2,4]triazolo[4,3-a][1,4]diazepine 6-(2-chlorophenyl)-8,9-dihydro-1-methyl-8-[(4-morpholinyl)carbonyl]-4H,7H-cyclo-penta-[4,5]thieno-[3,2-f][1,2,4]triazolo[4,3-a][1,4]diazepine, optionally in the form of the racemates, enantiomers, diastereomers thereof and optionally in the form of the pharmacologically acceptable acid addition salts, solvates or hydrates thereof. According to the invention the preferred acid addition salts of the betamimetics are selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The PI3-kinase-δ-inhibitors used are preferably compounds selected from among: IC87114, 2-(6-aminopurin-9-ylmethyl)-3-(2-chlorophenyl)-6.7-dimethoxy-3H-quinazolin-4-one; 2-(6-aminopurin-o-ylmethyl)-6-bromo-3-(2-chlorophenyl)-3H-quinazolin-4-one; 2-(6-aminopurin-o-ylmethyl)-3-(2-chlorophenyl)-7-fluoro-3H-quinazolin-4-one; 2-(6-aminopurin-9-ylmethyl)-6-chloro-3-(2-chlorophenyl)-3H-quinazolin-4-one; 2-(6-aminopurin-9-ylmethyl)-3-(2-chlorophenyl)-5-fluoro-3H-quinazolin-4-one; 2-(6-aminopurin-o-ylmethyl)-5-chloro-3-(2-chlorophenyl)-3H-quinazolin-4-one; 2-(6-aminopurin-9-ylmethyl)-3-(2-chlorophenyl)-5-methyl-3H-quinazolin-4-one; 2-(6-aminopurin-9-ylmethyl)-8-chloro-3-(2-chlorophenyl)-3H-quinazolin-4-one; 2-(6-aminopurin-9-ylmethyl)-3-biphenyl-2-yl-5-chloro-3H-quinazolin-4-one; 5-chloro-2-(9H-purin-6-ylsulphanylmethyl)-3-o-tolyl-3H-quinazolin-4-one; 5-chloro-3-(2-fluorophenyl)-2-(9H-purin-6-yl-sulphanylmethyl)-3H-quinazolin-4-one; 2-(6-aminopurin-9-ylmethyl)-5-chloro-3-(2-fluorophenyl)-3H-quinazolin-4-one; 3-biphenyl-2-yl-5-chloro-2-(9H-purin-6-ylsulphanylmethyl)-3H-quinazolin-4-one; 5-chloro-3-(2-methoxyphenyl)-2-(9H-purin-6-yl-sulphanylmethyl)-3H-quinazolin-4-one; 3-(2-chlorophenyl)-5-fluoro-2-(9H-purin-6-yl-sulphanylmethyl)-3H-quinazolin-4-one; 3-(2-chlorophenyl)-6.7-dimethoxy-2-(9H-purin-6-yl-sulphanylmethyl)-3H-quinazolin-4-one; 6-bromo-3-(2-chlorophenyl)-2-(9H-purin-6-yl-sulphanylmethyl)-3H-quinazolin-4-one; 3-(2-chlorophenyl)-8-trifluoromethyl-2-(9H-purin-6-ylsulphanylmethyl)-3H-quinazolin-4-one; 3-(2-chlorophenyl)-2-(9H-purin-6-ylsulphanylmethyl)-3H-benzo[g]quinazolin-4-one; 6-chloro-3-(2-chlorophenyl)-2-(9H-purin-6-yl-sulphanylmethyl)-3H-quinazolin-4-one; 8-chloro-3-(2-chlorophenyl)-2-(9H-purin-6-yl-sulphanylmethyl)-3H-quinazolin-4-one; 3-(2-chlorophenyl)-7-fluoro-2-(9H-purin-6-yl-sulphanylmethyl)-3H-quinazolin-4-one; 3-(2-chlorophenyl)-7-nitro-2-(9H-purin-6-yl-sulphanylmethyl)-3H-quinazolin-4-one; 3-(2-chlorophenyl)-6-hydroxy-2-(9H-purin-6-yl-sulphanylmethyl)-3H-quinazolin-4-one; 5-chloro-3-(2-chlorophenyl)-2-(9H-purin-6-yl-sulphanylmethyl)-3H-quinazolin-4-one; 3-(2-chlorophenyl)-5-methyl-2-(9H-purin-6-yl-sulphanylmethyl)-3H-quinazolin-4-one; 3-(2-chlorophenyl)-6.7-difluoro-2-(9H-purin-6-yl-sulphanylmethyl)-3H-quinazolin-4-one; 3-(2-chlorophenyl)-6-fluoro-2-(9H-purin-6-yl-sulphanylmethyl)-3H-quinazolin-4-one; 2-(6-aminopurin-9-ylmethyl)-3-(2-isopropylphenyl)-5-methyl-3H-quinazolin-4-one; 2-(6-aminopurin-9-ylmethyl)-5-methyl-3-o-tolyl-3H-quinazolin-4-one; 3-(2-fluorophenyl)-5-methyl-2-(9H-purin-6-yl-sulphanylmethyl)-3H-quinazolin-4-one; 2-(6-aminopurin-9-ylmethyl)-5-chloro-3-o-tolyl-3H-quinazolin-4-one; 2-(6-aminopurin-9-ylmethyl)-5-chloro-3-(2-methoxy-phenyl)-3H-quinazolin-4-one; 2-(2-amino-9H-purin-6-ylsulphanylmethyl)-3-cyclopropyl-5-methyl-3H-quinazolin-4-one; 3-cyclopropylmethyl-5-methyl-2-(9H-purin-6-ylsulphanylmethyl)-3H-quinazolin-4-one; 2-(6-aminopurin-9-ylmethyl)-3-cyclopropylmethyl-5-methyl-3H-quinazolin-4-one; 2-(2-amino-9H-purin-6-ylsulphanylmethyl)-3-cyclopropylmethyl-5-methyl-3H-quinazolin-4-one; 5-methyl-3-phenethyl-2-(9H-purin-6-ylsulphanylmethyl)-3H-quinazolin-4-one; 2-(2-amino-9H-purin-6-ylsulphanylmethyl)-5-methyl-3-phenethyl-3H-quinazolin-4-one; 3-cyclopentyl-5-methyl-2-(9H-purin-6-ylsulphanylmethyl)-3H-quinazolin-4-one; 2-(6-aminopurin-9-ylmethyl)-3-cyclopentyl-5-methyl-3H-quinazolin-4-one; 3-(2-chloropyridin-3-yl)-5-methyl-2-(9H-purin-6-ylsulphanylmethyl)-3H-quinazolin-4-one; 2-(6-aminopurin-9-ylmethyl)-3-(2-chloropyridin-3-yl)-5-methyl-3H-quinazolin-4-one; 3-methyl-4-[5-methyl-4-oxo-2-(9H-purin-6-ylsulphanylmethyl)-4H-quinazolin-3-yl]-benzoic acid; 3-cyclopropyl-5-methyl-2-(9H-purin-6-ylsulphanylmethyl)-

3H-quinazolin-4-one; 2-(6-aminopurin-9-ylmethyl)-3-cyclopropyl-5-methyl-3H-quinazolin-4-one; 5-methyl-3-(4-nitrobenzyl)-2-(9H-purin-6-ylsulphanylmethyl)-3H-quinazolin-4-one; 3-cyclohexyl-5-methyl-2-(9H-purin-6-ylsulphanylmethyl)-3H-quinazolin-4-one; 2-(6-aminopurin-9-ylmethyl)-3-cyclohexyl-5-methyl-3H-quinazolin-4-one; 2-(2-amino-9H-purin-6-ylsulphanylmethyl)-3-cyclo-hexyl-5-methyl-3H-quinazolin-4-one; 5-methyl-3-(E-2-phenylcyclopropyl)-2-(9H-purin-6-ylsulphanylmethyl)-3H-quinazolin-4-one; 3-(2-chlorophenyl)-5-fluoro-2-[(9H-purin-6-ylamino)methyl]-3H-quinazolin-4-one; 2-[(2-amino-9H-purin-6-ylamino)methyl]-3-(2-chlorophenyl)-5-fluoro-3H-quinazolin-4-one; 5-methyl-2-[(9H-purin-6-ylamino)methyl]-3-o-tolyl-3H-quinazolin-4-one; 2-[(2-amino-9H-purin-6-ylamino)methyl]-5-methyl-3-o-tolyl-3H-quinazolin-4-one; 2-[(2-fluoro-9H-purin-6-ylamino)methyl]-5-methyl-3-o-tolyl-3H-quinazolin-4-one; (2-chlorophenyl)-dimethylamino-(9H-purin-6-ylsulphanylmethyl)-3H-quinazolin-4-one; 5-(2-benzyloxyethoxy)-3-(2-chlorophenyl)-2-(9H-purin-6-ylsulphanylmethyl)-3H-quinazolin-4-one; 3-(2-chlorophenyl)-5-fluoro-4-oxo-3,4-dihydro-quinazolin-2-ylmethyl 6-aminopurine-9-carboxylate; N-[3-(2-chlorophenyl)-5-fluoro-4-oxo-3,4-dihydro-quinazolin-2-ylmethyl]-2-(9H-purin-6-ylsulphanyl)-acetamide; 2-[1-(2-fluoro-9H-purin-6-ylamino)ethyl]-5-methyl-3-o-tolyl-3H-quinazolin-4-one; 5-methyl-2-[1-(9H-purin-6-ylamino)ethyl]-3-o-tolyl-3H-quinazolin-4-one; 2-(6-dimethylaminopurin-9-ylmethyl)-5-methyl-3-o-tolyl-3H-quinazolin-4-one; 5-methyl-2-(2-methyl-6-oxo-1.6-di hydro-purin-7-ylmethyl)-3-o-tolyl-3H-quinazolin-4-one; 5-methyl-2-(2-methyl-6-oxo-1.6-dihydro-purin-9-ylmethyl)-3-o-tolyl-3H-quinazolin-4-one; 2-(amino-dimethylaminopurin-9-ylmethyl)-5-methyl-3-o-tolyl-3H-quinazolin-4-one; 2-(2-amino-9H-purin-6-ylsulphanylmethyl)-5-methyl-3-o-tolyl-3H-quinazolin-4-one; 2-(4-amino-1,3,5-triazin-2-ylsulphanylmethyl)-5-methyl-3-o-tolyl-3H-quinazolin-4-one; 5-methyl-2-(7-methyl-7H-purin-6-ylsulphanylmethyl)-3-o-tolyl-3H-quinazolin-4-one; 5-methyl-2-(2-oxo-1,2-dihydro-pyrimidin-4-ylsulphanylmethyl)-3-o-tolyl-3H-quinazolin-4-one; 5-methyl-2-purin-7-ylmethyl-3-o-tolyl-3H-quinazolin-4-one; 5-methyl-2-purin-9-ylmethyl-3-o-tolyl-3H-quinazolin-4-one; 5-methyl-2-(9-methyl-9H-purin-6-yl-sulphanylmethyl)-3-o-tolyl-3H-quinazolin-4-one; 2-(2,6-diamino-pyrimidin-4-ylsulphanylmethyl)-5-methyl-3-o-tolyl-3H-quinazolin-4-one; 5-methyl-2-(5-methyl-[1,2,4]triazolo[1.5-a]pyrimidin-7-ylsulphanylmethyl)-3-0-tolyl-3H-quinazolin-4-one; 5-methyl-2-(2-methylsulphanyl-9H-purin-6-ylsulphanylmethyl)-3-o-tolyl-3H-quinazolin-4-one; 2-(2-hydroxy-9H-purin-6-ylsulphanylmethyl)-5-methyl-3-o-tolyl-3H-quinazolin-4-one; 5-methyl-2-(1-methyl-1H-imidazol-2-ylsulphanylmethyl)-3-o-tolyl-3H-quinazolin-4-one; 5-methyl-3-0-tolyl-2-(H-[1,2,4]triazol-3-ylsulphanylmethyl)-3H-quinazolin-4-one; 2-(2-amino-6-chloro-purin-9-ylmethyl)-5-methyl-3-o-tolyl-3H-quinazolin-4-one; 2-(6-aminopurin-7-ylmethyl)-5-methyl-3-o-tolyl-3H-quinazolin-4-one; 2-(7-amino-1,2,3-triazolo[4,5-d]pyrimidin-3-ylmethyl)-5-methyl-3-o-tolyl-3H-quinazolin-4-one; 2-(7-amino-1,2,3-triazolo[4,5-d]pyrimidin-1-yl-methyl)-5-methyl-3-o-tolyl-3H-quinazolin-4-one; 2-(6-amino-9H-purin-2-ylsulphanylmethyl)-5-methyl-3-o-tolyl-3H-quinazolin-4-one; 2-(2-amino-6-ethylamino-pyrimidin-4-ylsulphanylmethyl)-5-methyl-3-o-tolyl-3H-quinazolin-4-one; 2-(3-amino-6-methylsulphanyl-1,2,4-triazol-1-ylmethyl)-5-methyl-3-o-tolyl-3H-quinazolin-4-one; 2-(5-amino-3-methylsulphanyl-1,2,4-triazol-1-ylmethyl)-5-methyl-3-o-tolyl-3H-quinazolin-4-one; 5-methyl-2-(6-methylaminopurin-9-ylmethyl)-3-o-tolyl-3H-quinazolin-4-one; 2-(6-benzylaminopurin-9-ylmethyl)-5-methyl-3-o-tolyl-3 H-quinazolin-4-one; 2-(2,6-diaminopurin-9-ylmethyl)-5-methyl-3-o-tolyl-3H-quinazolin-4-one; 5-methyl-2-(9H-purin-6-ylsulphanylmethyl)-3-o-tolyl-3H-quinazolin-4-one; 3-isobutyl-5-methyl-2-(9H-purin-6-ylsulphanylmethyl)-3H-quinazolin-4-one; N-{2-[5-methyl-4-oxo-2-(9H-purin-6-ylsulphanylmethyl)-4H-quinazolin-3-yl]-phenyl}-acetamide; 5-methyl-3-(E-2-methyl-cyclohexyl)-2-(9H-purin-6-ylsulphanylmethyl)-3H-quinazolin-4-one; 2-[5-methyl-4-oxo-2-(9H-purin-6-ylsulphanylmethyl)-4H-quinazolin-3-yl]-benzoic acid; 3-{2-[(2-dimethylaminoethyl)methylamino]phenyl}-5-methyl-2-(9H-purin-6-yl-sulphanylmethyl)-3H-quin-azolin-4-one; 3-(2-chlorophenyl)-5-methoxy-2-(9H-purin-6-ylsulphanyl-methyl)-3H-quinazolin-4-one; 3-(2-chlorophenyl)-5-(2-morpholin-4-yl-ethylamino)-2-(9H-purin-6-ylsulphanylm-ethyl)-3H-quinazolin-4-one; 3-benzyl-5-methoxy-2-(9H-purin-6-ylsulphanylmethyl)-3H-quinazolin-4-one; 2-(6-aminopurin-9-ylmethyl)-3-(2-benzyloxyphenyl)-5-methyl-3H-quinazolin-4-one; 2-(6-aminopurin-9-ylmethyl)-3-(2-hydroxyphenyl)-5-methyl-3H-quinazolin-4-one; 2-(1-(2-amino-9H-purin-6-ylamino)ethyl)-5-methyl-3-o-tolyl-3H-quinazolin-4-one; 5-methyl-2-[1-(9H-purin-6-ylamino)propyl]-3-o-tolyl-3H-quinazolin-4-one; 2-(1-(2-fluoro-9H-purin-6-ylamino)propyl)-5-methyl-3-o-tolyl-3H-quinazolin-4-one; 2-(1-(2-amino-9H-purin-6-ylamino)propyl)-5-methyl-3-o-tolyl-3H-quinazolin-4-one; 2-(2-benzyloxy-1-(9H-purin-6-ylamino)ethyl)-5-methyl-3-o-tolyl-3H-quinazolin-4-one; 2-(6-aminopurin-9-ylmethyl)-5-methyl-3-{2-(2-(1-methylpyrrolidin-2-yl)-ethoxy)-phenyl}-3H-quinazolin-4-one; 2-(6-aminopurin-9-ylmethyl)-3-(2-(3-dimethylamino-propoxy)-phenyl)-5-methyl-3H-quinazolin-4-one; 2-(6-aminopurin-9-yl methyl)-5-methyl-3-(2-prop-2-ynyloxyphenyl)-3H-quinazolin-4-one; 2-(2-(1-(6-aminopurin-9-ylmethyl)-5-methyl-4-oxo-4H-quinazolin-3-yl]-phenoxy}-acetamide; 5-chloro-3-(3,5-difluoro-phenyl)-2-[1-(9H-purin-6-ylamino)-propyl]-3H-quinazolin-4-one; 3-phenyl-2-[1-(9H-purin-6-ylamino)-propyl]-3H-quinazolin-4-one; 5-fluoro-3-phenyl-2-[1-(9H-purin-6-ylamino)-propyl]-3H-quinazolin-4-one; 3-(2,6-difluoro-phenyl)-5-methyl-2-[1-(9H-purin-6-ylamino)-propyl]-3H-quinazolin-4-one; 6-fluoro-3-phenyl-2-[1-(9H-purin-6-ylamino)-ethyl]-3H-quinazolin-4-one; 3-(3,5-difluoro-phenyl)-5-methyl-2-[1-(9H-purin-6-ylamino)-ethyl]-3H-quinazolin-4-one; 5-fluoro-3-phenyl-2-[1-(9H-purin-6-ylamino)-ethyl]-3H-quinazolin-4-one; 3-(2.3-difluoro-phenyl)-5-methyl-2-[1-(9H-purin-6-ylamino)-ethyl]-3H-quinazolin-4-one; 5-methyl-3-phenyl-2-[1-(9H-purin-6-ylamino)-ethyl]-3H-quinazolin-4-one; 3-(3-chloro-phenyl)-5-methyl-2-[1-(9H-purin-6-ylamino)-ethyl]-3H-quinazolin-4-one; 5-methyl-3-phenyl-2-[(9H-purin-6-ylamino)-methyl]-3H-quinazolin-4-one; 2-[(2-amino-9H-purin-6-ylamino)-methyl]-3-(3,5-difluoro-phenyl)-5-methyl-3H-quinazolin-4-one; 3-{2-[(2]-diethylamino-ethyl)-methyl-amino]-phenyl)-5-methyl-2-[(9H-purin-6-ylamino)-methyl]-3H-quinazolin-4-one; 5-chloro-3-(2-fluoro-phenyl)-2-[(9H-purin-6-ylamino)-methyl]-3H-quinazolin-4-one; 5-chloro-2-[(9H-purin-6-ylamino)-methyl]-3-o-tolyl-3H-quinazolin-4-one; 5-chloro-3-(2-chloro-phenyl)-2-[(9H-purin-6-ylamino)-methyl]-3H-quinazolin-4-one; 6-fluoro-3-(3-fluoro-phenyl)-2-[1-(9H-purin-6-ylamino)-ethyl]-3H-quinazolin-4-one; 2-[1-(2-amino-9H-purin-6-ylamino)-ethyl]-5-chloro-3-(3-fluoro-phenyl)-3H-quinazolin-4-one; and the pharmaceutically acceptable salts and solvates thereof.

Formulations

The compounds according to the invention may be administered by oral, transdermal, inhalative, parenteral or sublingual route. The compounds according to the invention are present as active ingredients in conventional preparations, for example in compositions consisting essentially of an inert pharmaceutical carrier and an effective dose of the active substance, such as for example tablets, coated tablets, capsules, lozenges, powders, solutions, suspensions, emulsions, syrups, suppositories, transdermal systems etc. An effective dose of the compounds according to the invention is between 0.1 and 5000, preferably between 1 and 500, more preferably between 5-300 mg/dose for oral administration, and between 0.001 and 50, preferably between 0.1 and 10 mg/dose for intravenous. subcutaneous or intramuscular administration. For inhalation, according to the invention, solutions containing 0.01 to 1.0, preferably 0.1 to 0.5% active substance are suitable. For administration by inhalation the use of powders, ethanolic or aqueous solutions is preferred. It is also possible to use the compounds according to the invention as a solution for infusion, preferably in a physiological saline or nutrient saline solution.

The compounds according to the invention may be used on their own or in conjunction with other active substances according to the invention, optionally also in conjunction with other pharmacologically active substances. Suitable formulations include, for example, tablets, capsules, suppositories, solutions, syrups, emulsions or dispersible powders. Corresponding tablets may be obtained for example by mixing the active substance(s) with known excipients, for example inert diluents, such as calcium carbonate, calcium phosphate or lactose, disintegrants such as maize starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection are prepared in the usual way, e.g. with the addition of preservatives such as p-hydroxybenzoates, or stabilisers such as alkali metal salts of ethylenediamine tetraacetic acid, and transferred into injection vials or ampoules.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

A therapeutically effective daily dose is between 1 and 2000 mg, preferably 10-500 mg per adult.

The Examples which follow illustrate the present invention without restricting its scope:

Examples of Pharmaceutical Formulations

| A) Tablets | per tablet |
|---|---|
| active substance | 100 mg |
| lactose | 140 mg |
| maize starch | 240 mg |
| polyvinylpyrrolidone | 15 mg |
| magnesium stearate | 5 mg |
| | 500 mg |

The finely ground active substance, lactose and some of the corn starch are mixed together. The mixture is screened, then moistened with a solution of polyvinylpyrrolidone in water, kneaded, granulated while wet and dried. The granulate, the rest of the corn starch and the magnesium stearate are screened and mixed together. The mixture is compressed to form tablets of a suitable shape and size.

| B) Tablets | per tablet |
|---|---|
| active substance | 80 mg |
| corn starch | 190 mg |
| lactose | 55 mg |
| microcrystalline cellulose | 35 mg |
| polyvinylpyrrolidone | 15 mg |
| sodium-carboxymethyl starch | 23 mg |
| magnesium stearate | 2 mg |
| | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodium-carboxymethyl starch and the magnesium stearate are added and mixed in and the mixture is compressed to form tablets of a suitable size.

| C) Coated tablets | per coated tablet |
|---|---|
| Active substance | 5 mg |
| Corn starch | 41.5 mg |
| Lactose | 30 mg |
| Polyvinylpyrrolidone | 3 mg |
| Magnesium stearate | 0.5 mg |
| | 80 mg |

The active substance, corn starch, lactose and polyvinylpyrrolidone are thoroughly mixed and moistened with water. The moist mass is pushed through a screen with a 1 mm mesh size, dried at about 45° C. and the granules are then passed through the same screen. After the magnesium stearate has been mixed in, convex tablet cores with a diameter of 6 mm are compressed in a tablet-making machine. The tablet cores thus produced are coated in a known manner with a covering consisting essentially of sugar and talc. The finished coated tablets are polished with wax

| D) Capsules | per capsule |
|---|---|
| Active substance | 50 mg |
| Corn starch | 268.5 mg |
| Magnesium stearate | 1.5 mg |
| | 320 mg |

The substance and corn starch are mixed and moistened with water. The moist mass is screened and dried. The dry granules are screened and mixed with magnesium stearate. The finished mixture is packed into size 1 hard gelatine capsules.

| E) Ampoule solution | |
|---|---|
| active substance | 50 mg |
| sodium chloride | 50 mg |
| water for inj. | 5 ml |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

| F) Suppositories | |
|---|---|
| Active substance | 50 mg |
| Solid fat | 1650 mg |
| | 1700 mg |

The hard fat is melted. At 40° C. the ground active substance is homogeneously dispersed. It is cooled to 38° C. and poured into slightly chilled suppository moulds.

| G) Oral suspension | |
|---|---|
| active substance | 50 mg |
| hydroxyethylcellulose | 50 mg |
| sorbic acid | 5 mg |
| sorbitol (70%) | 600 mg |
| glycerol | 200 mg |
| flavouring | 15 mg |
| water ad | 5 ml |

Distilled water is heated to 70° C. Hydroxyethyl-cellulose is dissolved therein with stirring. After the addition of sorbitol solution and glycerol the mixture is cooled to ambient temperature. At ambient temperature, sorbic acid, flavouring and substance are added. To eliminate air from the suspension it is evacuated with stirring.

The invention claimed is:

1. A compound of the formula (I)

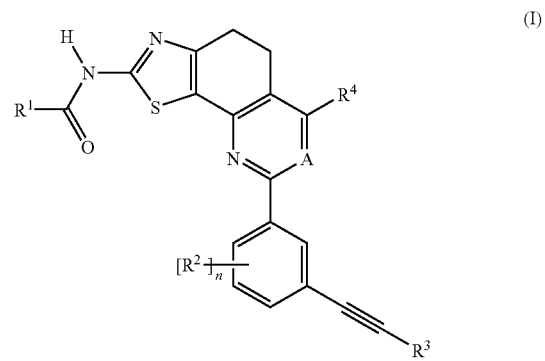

wherein

A denotes CH or N, n denotes 1, 2, 3 or 4, $R^1$ denotes hydrogen or a group, optionally substituted, consisting of $C_{1-4}$-alkyl, $OR^{1.1}$ and $NR^{1.1}R^{1.2}$;

$R^{1.1}$, $R^{1.2}$ which may be identical or different, denote H or $C_{1-4}$-alkyl; or $NR^{1.1}R^{1.2}$ denotes a 5- to 6-membered heterocycle, optionally containing a further N atom;

$R^2$ which may be identical or different, denote hydrogen or a group selected from among F, Cl, Br, I, CN, $CF_3$, $CF_2H$, $CFH_2$ and $NH_2$; or a group, optionally substituted, selected from among —O—$C_{1-4}$-alkyl, $C_{1-4}$-alkyl and $C_{2-6}$-alkenyl;

$R^4$ denotes hydrogen, OH, $NH_2$, or a group, optionally substituted, selected from among $C_{1-6}$-alkyl, $C_{2-6}$-alkenyl, $C_{3-6}$-cycloalkyl, —$N(C_{1-4}$-alkyl$)_2$ and —$NH(C_{1-4}$-alkyl);

$R^3$ denotes a group selected from among:

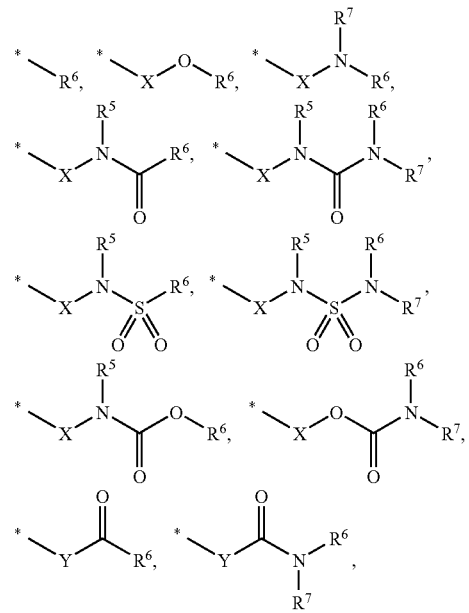

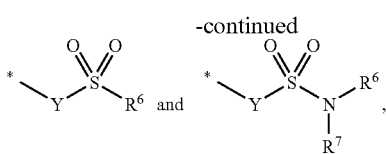

wherein
X denotes a group, optionally substituted, selected from among $C_{1-6}$-alkylene, $C_{2-5}$-alkenylene, $C_{1-5}$-alkynylene, $C_{3-7}$-cycloalkylene, $C_{5-7}$-cycloalkenylene and —$C_{1-4}$-alkylene-$C_{3-7}$-cycloalkylene;
Y denotes a bond or X;
$R^5$, $R^6$, $R^7$ which may be identical or different, denote hydrogen or a group, optionally substituted, selected from among $C_{1-6}$-alkyl, $C_{2-6}$-alkenyl, $C_{2-6}$-alkynyl, $C_{1-6}$-haloalkyl, $C_{3-8}$-cycloalkyl, $C_{3-8}$-cycloalkenyl, $C_{3-7}$-cycloalkyl-$C_{1-4}$-alkyl, aryl, heteroaryl, spiro, heterocycloalkyl, aryl-$C_{1-6}$-alkyl, heteroaryl-$C_{1-6}$-alkyl and heterocycloalkyl-$C_{1-6}$-alkyl, or
$NR^6R^7$ form

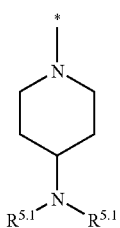

$R^{5.1}$ which may be identical or different, denote hydrogen or a group selected from among $C_{1-6}$-alkyl, $C_{3-8}$-cycloalkyl, —CO—$C_{1-3}$-alkyl and $CONH_2$;
or $R^3$ is

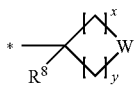

x, y which may be identical or different denote 0, 1, 2, 3, 4 or 5;
W denotes O, $NR^9$ or $CR^9R^{10}$;
$R^8$ denotes H, $OR^{8.1}$, $NR^{8.1}R^{8.2}$ or optionally substituted $C_{1-6}$-alkyl;
$R^{8.1}$, $R^{8.2}$ which may be identical or different, denote hydrogen, $COR^{8.1.1}$, $CONR^{8.1.1}R^{8.1.2}$, $SO_2NR^{8.1.1}R^{8.1.2}$ or $SO_2R^{8.1.1}$ or a group, optionally substituted, selected from among $C_{1-6}$-alkyl, $C_{3-6}$-alkenyl, $C_{3-6}$-alkynyl, $C_{3-8}$-cycloalkyl and $C_{3-7}$-cycloalkyl-$C_{1-4}$-alkyl, or
$NR^{8.1}R^{8.2}$ together form a five-, six- or seven-membered ring which may optionally contain a further heteroatom;
$R^{8.1.1}$, $R^{8.1.2}$ which may be identical or different, denote hydrogen or a group, optionally substituted, selected from among $C_{1-6}$-alkyl, $C_{3-8}$-cycloalkyl and $C_{3-7}$-cycloalkyl-$C_{1-4}$-alkyl, or
$NR^{8.1.1}R^{8.1.2}$ together form a five- or six-membered ring, which may optionally contain a further heteroatom;
$R^9$, $R^{10}$ which may be identical or different, denote a group, optionally substituted by OMe, CN, F, Cl or Br, selected from among $C_{1-6}$-alkyl, $C_{2-6}$-alkenyl, $C_{2-6}$-alkynyl, $C_{3-8}$-cycloalkyl, $C_{3-8}$-cycloalkenyl, $C_{3-7}$-cycloalkyl-$C_{1-4}$-alkyl, aryl, heteroaryl, spiro, heterocycloalkyl, aryl-$C_{7-11}$-alkyl-(aryl-$C_{1-6}$-alkyl-) and heteroaryl-$C_{6-10}$-alkyl (heteroaryl-$C_{1-6}$-alkyl); or
$R^9$, $R^{10}$, which may be identical or different, denote hydrogen, $COR^{9.1}$, $CONR^{9.1}R^{9.2}$, $SO_2R^{9.1}$ or $SO_2NR^{9.1}R^{9.2}$;
$R^{9.1}$, $R^{9.2}$ which may be identical or different, denote hydrogen or an optionally substituted group selected from among $C_{1-6}$-alkyl, $C_{2-6}$-alkenyl, $C_{2-6}$-alkynyl, $C_{1-6}$-haloalkyl, $C_{3-8}$-cycloalkyl, $C_{3-7}$-cycloalkyl-$C_{1-4}$-alkyl, aryl, heteroaryl, spiro, heterocycloalkyl, aryl-$C_{1-6}$-alkyl- and heteroaryl-$C_{1-6}$-alkyl-; or
$NR^{9.1}R^{9.2}$ together form a five- or six-membered ring, which may optionally contain a further heteroatom,
optionally in the form of pharmacologically acceptable acid addition salts thereof.

2. The compound according to claim 1,

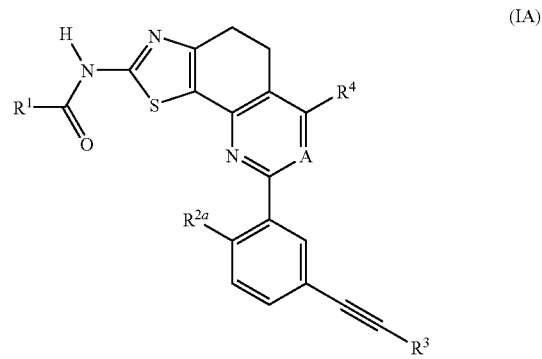

wherein
A, $R^1$, $R^3$, and $R^4$ may have the meanings stated and
$R^{2a}$ denotes a group selected from among F, Cl, Br, I, CN, $CF_3$, $CF_2H$, $CFH_2$ and $NH_2$;
or a group, optionally substituted, selected from among —O—$C_{1-4}$-alkyl, $C_{1-4}$-alkyl and $C_{2-6}$-alkenyl.

3. The compound according to claim 2, wherein
$R^3$ may have the meanings stated and
n denotes 1 or 2,
$R^1$ denotes $C_{1-4}$-alkyl or $NR^{1.1}R^{1.2}$;
$R^{1.1}$, $R^{1.2}$ which may be identical or different, denote H or $C_{1-4}$-alkyl;
$R^2$ and/or $R^{2a}$ which may be identical or different, denote hydrogen, F or Cl; and
$R^4$ denotes hydrogen.

4. The compound according to claim 3, wherein
$R^1$, $R^2$, and $R^4$ may have the meanings stated and
$R^3$ denotes a group selected from among:

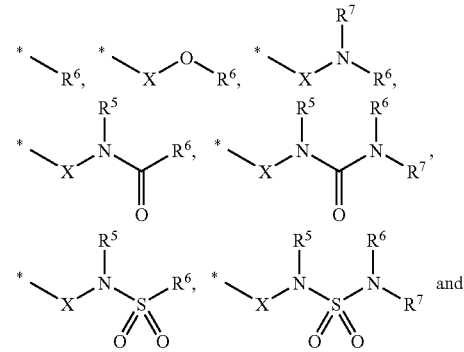

-continued

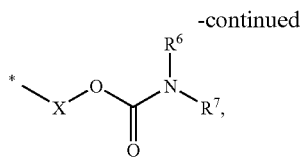

wherein

X denotes optionally substituted $C_{1-3}$-alkylene, $R^5$, $R^6$, $R^7$ which may be identical or different, denote hydrogen or a group, optionally substituted, selected from among $C_{1-6}$-alkyl, $C_{2-6}$-alkenyl, $C_{1-6}$-haloalkyl, $C_{3-8}$-cycloalkyl, $C_{3-7}$-cycloalkyl-$C_{1-4}$-alkyl, aryl, heteroaryl, heterocycloalkyl, aryl-$C_{1-5}$-alkyl, heteroaryl-$C_{1-5}$-alkyl, heterocycloalkyl-$C_{1-5}$-alkyl- and N($C_{1-3}$-alkyl)$_2$-$C_{1-4}$-alkyl- or $NR^6R^7$ form

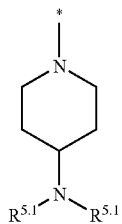

$R^{5.1}$ which may be identical or different, denote hydrogen or a group selected from among $C_{1-6}$-alkyl, $C_{3-8}$-cycloalkyl, —CO—$C_{1-3}$-alkyl and $CONH_2$.

5. The compound according to claim 3, wherein $R^1$, $R^2$, and $R^4$ may have the meanings stated and $R^3$ denotes a group:

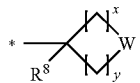

x, y which may be identical or different denote 0, 1, 2 or 3,

W denotes $NR^9$ or $CR^9R^{10}$;

$R^8$ denotes H, $OR^{8.1}$ or $NR^{8.1}R^{8.2}$, $R^{8.1}$, $R^{8.2}$ which may be identical or different, denote hydrogen, $COR^{8.1.1}$, $CONR^{8.1.1}R^{8.1.2}$, or optionally substituted $C_{1-6}$-alkyl;

$NR^{8.1}R^{8.2}$ together form a five- or six-membered ring which may optionally contain a further heteroatom;

$R^{8.1.1}$, $R^{8.1.2}$ which may be identical or different, denote hydrogen or an optionally substituted $C_{1-6}$-alkyl, $R^9$, $R^{10}$ which may be identical or different, denote a group, optionally substituted by OMe, CN, F, Cl or Br, selected from among $C_{1-6}$-alkyl, $C_{3-8}$-cycloalkyl, $C_{3-7}$-cycloalkyl-$C_{1-4}$-alkyl or $R^9$, $R^{10}$ which may be identical or different, denote hydrogen, $COR^{9.1}$, $CONR^{9.1}R^{9.2}$, $SO_2R^{9.1}$ or $SO_2NR^{9.1}R^{9.2}$;

$R^{9.1}$, $R^{9.2}$ which may be identical or different, denote hydrogen or an optionally substituted group selected from among $C_{1-6}$-alkyl and $C_{3-8}$-cycloalkyl, or $NR^{9.1}R^{9.2}$ together form a five- or six-membered ring, which may optionally contain oxygen as a further heteroatom.

6. A pharmaceutical composition comprising a pharmaceutical carrier and a pharmaceutically effective amount of a compound according to claim 1.

7. The pharmaceutical composition according to claim 6 which is orally administered.

8. A pharmaceutical composition comprising one or more compounds of formula (I) according to claim 1, and as a further active substance, one or more compounds which are selected from the categories of the betamimetics, anticholinergics, corticosteroids, other PDE4-inhibitors, LTD4-antagonists, EGFR-inhibitors, dopamine agonists, H1-antihistamines, PAF-antagonists and PI3-kinase inhibitors or double or triple combinations thereof.

9. A compound of the formula (IV),

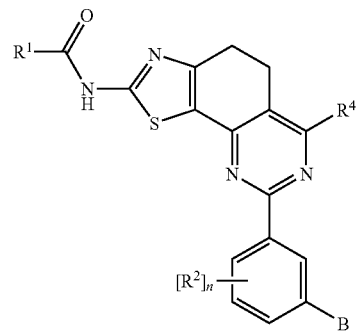

wherein A, $R^1$, $R^2$, $R^4$ and n have the meanings specified in claim 1 and B denotes a leaving group, optionally in the form of the pharmacologically acceptable acid addition salts, with the proviso that $R^1$ cannot be methyl if $R^2$=H, B=Cl and $R^4$=H.

* * * * *